(12) United States Patent
Borchardt et al.

(10) Patent No.: US 11,473,103 B2
(45) Date of Patent: Oct. 18, 2022

(54) NUCLEUS-ENCODED MALE STERILITY THROUGH MUTATION IN CYTOCHROME P450 OXIDASE

(71) Applicant: KWS SAAT SE & CO. KGAA, Einbeck (DE)

(72) Inventors: Dietrich Borchardt, Einbeck (DE); Olaf Czarnecki, Berlin (DE); Wolfgang Mechelke, Einbeck (DE)

(73) Assignee: KWS SAAT SE & CO. KGAA, Einbeck (DE)

( * ) Notice: Subject to any disclaimer, the term of this patent is extended or adjusted under 35 U.S.C. 154(b) by 252 days.

(21) Appl. No.: 16/092,613

(22) PCT Filed: Apr. 12, 2017

(86) PCT No.: PCT/EP2017/058815
§ 371 (c)(1),
(2) Date: Mar. 14, 2019

(87) PCT Pub. No.: WO2017/178541
PCT Pub. Date: Oct. 19, 2017

(65) Prior Publication Data
US 2019/0194685 A1 Jun. 27, 2019

(30) Foreign Application Priority Data
Apr. 12, 2016 (DE) .......................... 102016106656.7

(51) Int. Cl.
| | | |
|---|---|---|
| *C12N 15/82* | (2006.01) | |
| *C12N 9/00* | (2006.01) | |
| *A01H 5/06* | (2018.01) | |
| *C12N 9/02* | (2006.01) | |
| *C12N 15/113* | (2010.01) | |

(52) U.S. Cl.
CPC ....... *C12N 15/8289* (2013.01); *C12N 9/0071* (2013.01); *C12N 15/1137* (2013.01); *C12N 2310/122* (2013.01); *C12N 2310/14* (2013.01)

(58) Field of Classification Search
CPC ................................................. C12N 15/8279
See application file for complete search history.

(56) References Cited

U.S. PATENT DOCUMENTS

2006/0288440 A1 12/2006 Albertsen et al.

FOREIGN PATENT DOCUMENTS

| | | |
|---|---|---|
| DE | 10 2012 022 178 A1 | 5/2014 |
| DE | 10 2013 101 617 A1 | 8/2014 |
| EP | 0 344 029 A1 | 11/1989 |
| WO | 96/17945 A1 | 6/1996 |
| WO | 99/23232 A1 | 5/1999 |
| WO | 00/18939 A1 | 4/2000 |
| WO | 00/75359 | 12/2000 |
| WO | 01/12824 A1 | 2/2001 |
| WO | 2004/074492 A1 | 9/2004 |
| WO | 2013/138309 A1 | 9/2013 |
| WO | 2014/144155 A1 | 9/2014 |

OTHER PUBLICATIONS

Locus KMT20292 available Jul. 2015.*
Locus XP_010665532 available Nov. 2016.*
Hatlestad, Gregory J., et al. "The beet R locus encodes a new cytochrome P450 required for red betalain production." Nature genetics 44.7 (2012): 816-820. (Year: 2012).*
Morant et al (2007, The Plant Cell 9: 1473-1487) (Year: 2007).*
Vesna Djukanovic et al., "Male-sterile maize plants produced by targeted mutagenesis of the cytochrome P450-like gene (MS26) using a re-designed I-CreI homing endonuclease", The Plant Journal, (2013) 76, pp. 888-899.
A. Mark Cigan et al., "Targeted mutagenesis of a conserved anther-expressed P450 gene confers male sterility in monocots", Plant Biotechnology Journal, (2017) 15, pp. 379-389.
H. Li et al., "Cytochrome P450 Family Member CYP704B2 Catalyzes the ω-Hydroxylation of Fatty Acids and Is Required for Anther Cutin Biosynthesis and Pollen Exine Formation in Rice", The Plant Cell, Jan. 2010 22, pp. 173-190.
Database UniProt [Online] Oct. 14, 2015, "SubName: Full= Uncharacterized protein {EC0:0000313 EMBL: KMT20292.1};", XP002773258, EBI accession No. UNIPROT: A0A0J8D3D0 Database accession No. A0A0J8D3D0 Sequence.
M. Morant et al., CYP703 Is an Ancient Cytochrome P450 in Land Plants Catalyzing in-Chain Hydroxylation of Lauric Acid to Provide Building Blocks for Sporopollenin Synthesis in Pollen, The Plant Cell, May 2007 19, pp. 1473-1487.
Kim Sung Soo et al., "Sporopollenin monomer biosynthesis in *Arabidopsis*" Journal of Plant Biology, Botanical Society of Korea, (2013) 56, pp. 1-6.
International Search Report for PCT/EP2017/058815 dated Aug. 9, 2017.
Napoli et al., "white anther: A Petunia Mutant That Abolishes Pollen Flavonol Accumulation, Induces Maio Sterility, and Is Complemented by a Chalcone Synthase Transgene", Plant Physiology, 1999, vol. 120, pp. 615-622.
Jeong et al., "Tomato Male sterile 1035 is essential for pollen development and meiosis in anthers", Journal of Experimental Botany, 2014, vol. 65, No. 22, pp. 6693-6709.

(Continued)

Primary Examiner — Weihua Fan
(74) Attorney, Agent, or Firm — Troutman Pepper Hamilton Sanders LLP

(57) ABSTRACT

The invention relates to plants having a nucleus-encoded, recessive, male sterile phenotype and to the gene locus (gst) correlating therewith, including the gene which is responsible for the fertile/sterile phenotype and which is mutated in the sterile phenotype. The invention further provides methods for identifying the genotype correlating with the expression of features indicated above, and the corresponding genetic tools, such as hybridization probes and oligonucleotides. Also described is the use of the plants obtained according to the invention in hybrid breeding and in the production of products obtained from renewable raw materials, such as bioethanol, biogas and sugar-based products.

13 Claims, 15 Drawing Sheets

Figure 1:
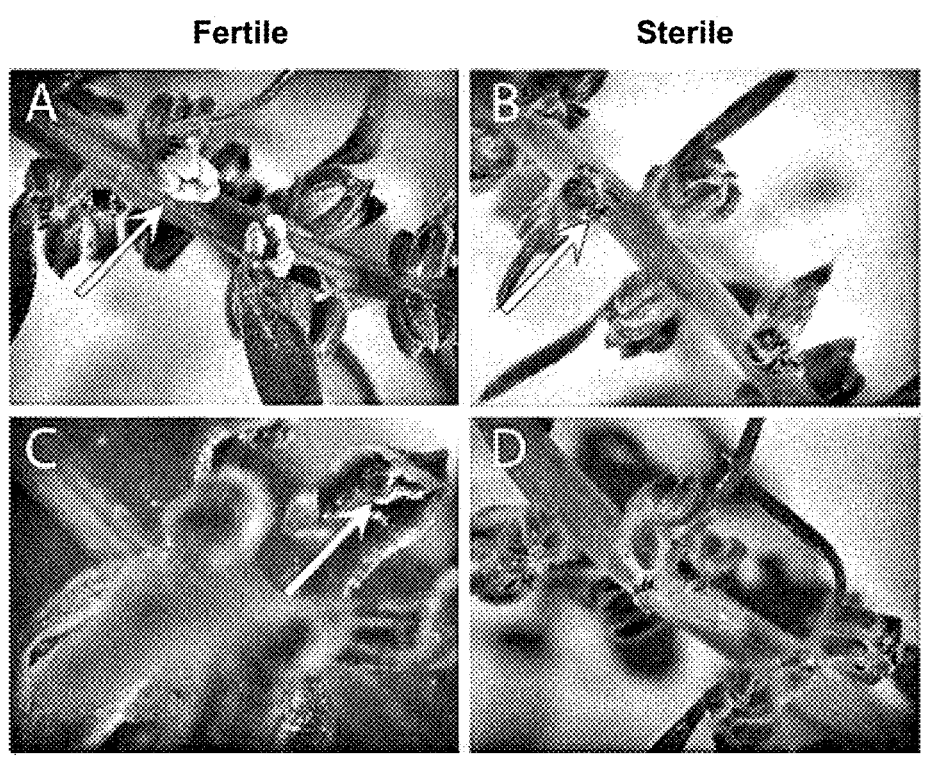

Specification includes a Sequence Listing.

(56) References Cited

OTHER PUBLICATIONS

Osakabe et al., "Genome Editing with Engineered Nucleases in Plants", Plant Cell Physiology, 2015, vol. 56, No. 3, pp. 389-400.
Henikoff et al., "TILLING. Traditional Mutagenesis Meets Functional Genomics", Plant Physiology, 2004, vol. 135, pp. 630-636.
Fischer et al., "The Cytochrome P450 Engineering Database: a navigation and prediction tool for the cytochrome P450 protein family", Bioinformatics, 2007, vol. 23, No. 15, pp. 2015-2017.
Written Opinion issued in International Application No. PCT/EP2017/058815 dated Aug. 9, 2017.

* cited by examiner

```
Consensus_Fertil  GTATATCGTT GCCACATGTG CGTTGAATTT TATCCTTTTCC ACTCCATATT CTCCCTCAAAA GTGTGTAAAA ATCCGACACA  90
Consensus_Steril  GTATATCGTT GCCACATGTG CGTTGAATTT TATCCTTTTCC ACTCCATATT CTCCCTCAAAA GTGTGTAAAA ATCCGACACA  90

Consensus_Fertil  CGAGTAGAAT GGGATTGAAG TGGGTCAAGA TCTGAAACCA GCCAGAAAAT AAGGTAAGGT TTCTCGCAGT AGCAAAAAAA 180
Consensus_Steril  CGAGTAGAAT GGGATTGAAG TGGGTCAAGA TCTGAAACCA GCCAGAAAAT AAGGTAAGGT TTCGCGCAGT AGCAAAAAAA 180

Consensus_Fertil  TAAAGTTAAG TTGAGAGAAA AATTATGAAT AGTTGTTTCT CGTGAAGAGT TGTATACAAA AAAAGTCTAA TTTCTTTTAC 270
Consensus_Steril  TAAAGTTAAG TTGAGAGAAA AATTATGAAT AGTTGTTTCT CGTGAAGAGT TGTATACAAA AAAAGTCTAA TTTCTTTTAC 270

Consensus_Fertil  ATTTATAAAG GATTGACCAA TCATCCAAAT TACCAAATAT TTAGGATATA AATCTTTCAG ATTACAAACC CACTAAATTT 360
Consensus_Steril  ATTTATAAAG GATTGACCAA TCATCCAAAT TACCAAATAT TTAGGATATA AATCTTTCAG ATTACAACCC CACTAAATTT 360

Consensus_Fertil  TACATGAGGC AATGGAGGAT TTGCATGAAT ATCGAGGAGA GAAAAAATTA GTTACAAAAC TTGCATAATT TATCCAAACC AAATCAAGTC 450
Consensus_Steril  TACATGAGGC AATGGAGGAT TTGCATGAAT ATCGAGGAGA GAAAAAATTA GTTACAAAAC TTGCATAATT TATCCAAACC AAATCAAGTC 450

Consensus_Fertil  AAGAAACAAC GAACAATATT ATCATTAGTA CTATAAGTAT ATATTATAGG CTTAGAGCAA AGCCCTAACT ACCACACTGC ACACAAATGA 540
Consensus_Steril  AAGAAACAAC GAACAATATT ATCATTAGTA CTATAAGTAT ATATTATAGG CTTAGAGCAA AGCCCTAACT ACCACACTGC ACACAAATGA 540

Consensus_Fertil  TAACTAGTAA GAGAGGAAAA TACAAATTTA AGATTCAACA TTCATGATTC ATGATTCATG AGATTCAACA TTCATGATT CATGATTCAC 630
Consensus_Steril  TAACTAGTAA GAGAGGAAAA TACAAATTTA AGATTCAACA TTCATGATTC ATGATTCATG AGATTCAACA TTCATGATT CATGATTCAC 630
```

Fig. 3

```
Consensus_Fertil  CAATATTTCA CAACATTATA TCTTGAATAGT TGGTTGAAAT TAATAATTTT CAATAATTTC AAAAGGCAAA AAGCTTCTTT GTTCGGATAA 4301
Consensus_Steril  CAATATTTCA CAACATTATA TCTTGAATAGT TGGTTGAAAT TAATAATTTT CAATAATTTC AAAAGGCAAA AAGCTTCTTT GTTCGGATAA 3775

Consensus_Fertil  ATTCACGTCA TTTTCAATTAA AATCGCCAAA TCTTCCCTTG CCATCAAGGA ACAAATTTTT CACATCAAAA CTCCTTCTTCC AAAAAGTATA 4391
Consensus_Steril  ATTCAGTCA  TTTTCAATTAA AATCGGAAAA TCTTCCCTTG CCATCAAGGA ACAAATTTTT CACATCAAAA CTCCTTCTTCC AAAAAGTATA 3865

Consensus_Fertil  CTTCTCCACT GATTATGTAA AAGAGTTTGC ATGTTCTAAT CTATTAGTAT GTATTTTTCG GATAAGAAGT TGTATTACAA GCTTAAATAA 4481
Consensus_Steril  CTTCTTCCATT GATTATGTAA AAGAGTTTGC ATGTTCTAAT CCATTAGTAT GTATTTTTCG GATAAGAAGT TGTATTACAA GCTTAAATAA 3955

Consensus_Fertil  AGATATAAAC TTAAATGAAT ATCGACCAAT CCACAAATATG TATCTTCATA TGTGTCCATC ARGCCTAAC  CTTGAGATGT AGATCATCTA 4571
Consensus_Steril  AGATATAAAC TTAGTTAAAT ATCGACCAAT CCACAAATATG TATCTTCATA TGTGTCCATC AGCGCCTAAC CTTGAGATGT AGATCATCTA 4045

Consensus_Fertil  AAGCCACATTA ACATGTCGTA CTCCTCATGT TCA-----GG GTTGTTTGAA ACCCAACTTC TCCAAAATAC TTCCCTCAGTA ATAAAGACAA 4656
Consensus_Steril  AAGCCACATTA ACATGGCGTA CTCCTCGTGT TCAAATGAGG GTTGTTTGAA ACCGAACTTC TCCAAAATAC TTCCCTCAGTA ATGAAGAGAA 4135

Consensus_Fertil  AAACTCACAT TCTGAAAAAC ATCAACATTA TGGTTCTATG GTCTAGTGGT TATGACACTG GACTCTGAAT CCAGTAACCC GAGTT 4741
Consensus_Steril  AAACTCACAT TCTGAAAAAC ATCAACATCA TGGTTCTATG GTCTAGTGGT TATGACACTG GACTCTGAAT CCAGTAACCC GAGTT 4220
```

GCAAAAGCTTCTTTGTTCGGATAAATTCACGTCATTTTCAATAAATGCAAAATCTTCCTTGCCATCAAGGA
ACAAATTTTTCACATCAAAACTCTTCTTCCAAAAAGTATACTTCTCCATTGATTATGTAAAAGAGTTTGCATGTT
CTAATCCATTAGTATGTATTTTTCGGATAAGAAGTTGTATTACAAGCTTAAATAAGATATAAACTTAGTTAAAT
ATCAACAATCCACAATATGTATCTTCATATGTGTCCATCACCGCCTAACCTTGACATGTACATCATCTAAGCA
CATTAACATGCCGTACTCCTCCTGTTCAAATCAGGGTTGTTTGAAAACCAAACTTCTCCAAAATACTTCCTCAGTA
ATGAAGACAAAAACTCACATTCTGAAAAACATCAACATGATGGTTCTATGGTCTACTGGTTATGACACTGGACTC
TGAATCCAGTAACCCGAGTT

Fig. 4 (continued)

SEQUENCE LISTING

```
<160> NUMBER OF SEQ ID NOS: 28

<210> SEQ ID NO 1
<211> LENGTH: 4328
<212> TYPE: DNA
<213> ORGANISM: Beta vulgaris
<220> FEATURE:
<221> NAME/KEY: Promotor
<222> LOCATION: (1)..(1518)
<223> OTHER INFORMATION: putativer Promotor
<220> FEATURE:
<221> NAME/KEY: Gen
<222> LOCATION: (1519)..(4275)
<220> FEATURE:
<221> NAME/KEY: 5'UTR
<222> LOCATION: (1519)..(1761)
<220> FEATURE:
<221> NAME/KEY: exon
<222> LOCATION: (1762)..(2679)
<223> OTHER INFORMATION: Exon 1
<220> FEATURE:
```

```
<221> NAME/KEY: Intron
<222> LOCATION: (2680)..(3506)
<220> FEATURE:
<221> NAME/KEY: exon
<222> LOCATION: (3507)..(4142)
<223> OTHER INFORMATION: Exon 2
<220> FEATURE:
<221> NAME/KEY: 3'UTR
<222> LOCATION: (4143)..(4275)

<400> SEQUENCE: 1
```

| | | | | | |
|---|---|---|---|---|---|
| ttattaaacc | tgattggaac | ttattgaacc | ttattagacc | tgattggaac | ttattgcacc | 60 |
| tgattggaac | ttattggaac | ttattagacc | ttattggaac | ttattgcact | tattagacct | 120 |
| tattgcaact | tatctgaact | tatctgaaca | aatctgaact | tattggacct | gaaacttaat | 180 |
| tttttaagtt | gaacagaacg | cacccttagt | atatcgttgc | cacatgtgcg | ttgaattttt | 240 |
| ccttttccta | tcctttccac | tccatattct | cctcaaaagt | gtgtaaaaat | ccgacacacg | 300 |
| agtagaatgg | gattgaagtg | ggtcaagatc | tgaaaccaat | gggtcaatgc | cacaaaataa | 360 |
| ggtaaggttt | ctcgcagtag | caaaaaaata | aagttaagtt | gagagaaaaa | ttatgaatag | 420 |
| ttgtttctcg | tgaagagttg | tatacaaaaa | aagtctaatt | tgatacattt | tcttttacat | 480 |
| ttataaagga | ttgaccaatc | atccaaatta | ccaaatattt | aggatataaa | tctttcgat | 540 |
| tacaacccat | atatgataca | ctaaatttta | catgaggcaa | tggaggattt | gcatgaatat | 600 |
| cgaggagaga | aaaaattagt | tacaaaactt | gcataattta | tccaaaccaa | atcaagtcaa | 660 |
| gaaacaacga | acaatattat | cattagtact | ataagtatat | attataggct | tagagcaaag | 720 |
| ccctaactac | cacactgcac | acaaatgata | actagtaaga | gaggaaaata | caaatttaag | 780 |
| attcaacata | gcaaattatt | catgattcat | gattcatgat | tcatgattca | tgattcacga | 840 |
| acatcaagaa | tggtatagct | gataaaggac | aatttaaaca | taagtgtaaa | gctcgcacat | 900 |
| catcaattat | attcgcatac | tactagacca | atctttactt | agtacatgtg | ttagtacatg | 960 |
| tgttacttca | tatcagatgt | attgattgtt | gccaatgaca | tatcatgttc | acttaatctt | 1020 |
| agggccattt | aattataaca | tggagaataa | tacaacttaa | aattatgtgg | tggctatcat | 1080 |
| ctcattttct | agataattaa | accttttattt | tgtatacata | tatattgtct | ttacatagca | 1140 |
| aaacaatatt | gaaggtataa | caaccttttcc | cttttctttt | actacatgtt | tatgttagag | 1200 |
| tttttcgatt | tacgattgtg | gtaaattaat | tgtaattgat | cggttgtctt | gtagtcaaga | 1260 |
| aatgacgtat | gaatcaattt | agggcatgtt | ctcttcggca | taaaacagct | gaactgaatt | 1320 |
| gaactgaact | gaaatgaata | gtgatatgtg | agagtaaaag | tattgtcaag | agctgaactg | 1380 |
| agctgaactg | aacggatctg | aactgaactg | atctaatctg | aactaatctg | aactgaactg | 1440 |
| aactgaattg | aactgaaaat | aagctaggga | aaacagaccc | ttactactat | tatataaccct | 1500 |
| cgtttaaata | ttaggaaatt | aaaaaaataa | ttatatttct | ttatactta | ttaacctatt | 1560 |
| gaggttttta | tattgactcc | caaatactat | tttatagatc | atgccatgtt | aatgagcaaa | 1620 |
| ctactttctc | acatctttat | aggagaaaaa | gtagatcact | cactagcata | tcatgaccag | 1680 |
| cgaaaccaac | caacgctaat | agttttattg | cttccattag | agataagagt | taactaataa | 1740 |
| taccatctttt | gtgaaatttt | g atg gat ttt gga act tta gca ata tat tta | | | 1791 |

```
                     Met Asp Phe Gly Thr Leu Ala Ile Tyr Leu
                      1               5                  10 ctg tgt gca ctt ttt gct acc aaa att tta tac caa tgg ctc aag tcc                      1839
Leu Cys Ala Leu Phe Ala Thr Lys Ile Leu Tyr Gln Trp Leu Lys Ser
                15                  20                  25 tac tta tac aca aca tac aaa ctc cct ccc ggc cca cca agg tgg ccc                      1887
```

```
                Tyr Leu Tyr Thr Thr Tyr Lys Leu Pro Pro Gly Pro Pro Arg Trp Pro
                                30                  35                  40 tta ttt gga aac ctc ctt caa cta ggg cca ctt ccc cac cgc gat ttc               1935
Leu Phe Gly Asn Leu Leu Gln Leu Gly Pro Leu Pro His Arg Asp Phe
        45                  50                  55 gcc tca ttt tgt gaa aaa tat ggg cct tta gtc tac ata agg ctt ggt               1983
Ala Ser Phe Cys Glu Lys Tyr Gly Pro Leu Val Tyr Ile Arg Leu Gly
        60                  65                  70 aat gtg gat gcc ata acc act aat gat cca gaa atc ata cgt gag atc               2031
Asn Val Asp Ala Ile Thr Thr Asn Asp Pro Glu Ile Ile Arg Glu Ile
75                  80                  85                  90 tta gtt cga caa gat gat gta ttt gcg tct cgt cca cat acc tta gcc               2079
Leu Val Arg Gln Asp Asp Val Phe Ala Ser Arg Pro His Thr Leu Ala
                95                  100                 105 gca acc cac ttg gct tac aat agt ggt gat gtg gcc ttg gct cca atg               2127
Ala Thr His Leu Ala Tyr Asn Ser Gly Asp Val Ala Leu Ala Pro Met
            110                 115                 120 gga cca aaa tgg aaa aga atg aga agg ata tgc atg gag cac ttg ctc               2175
Gly Pro Lys Trp Lys Arg Met Arg Arg Ile Cys Met Glu His Leu Leu
            125                 130                 135 aca act aga cga ctt gaa cta ttt gtg agt cat agg gct gat gag gca               2223
Thr Thr Arg Arg Leu Glu Leu Phe Val Ser His Arg Ala Asp Glu Ala
        140                 145                 150 cga cat ttg gtc caa gac gta tta act cgt tcc cac aaa gat aaa gtt               2271
Arg His Leu Val Gln Asp Val Leu Thr Arg Ser His Lys Asp Lys Val
155                 160                 165                 170 gtt aat ttg agg gaa gtg tta ggt gca ttt tct atg aat aac gtg act               2319
Val Asn Leu Arg Glu Val Leu Gly Ala Phe Ser Met Asn Asn Val Thr
                175                 180                 185 aga atg ttg cta ggg aag caa tac ttt ggg gcc ggg acg gcg ggc cca               2367
Arg Met Leu Leu Gly Lys Gln Tyr Phe Gly Ala Gly Thr Ala Gly Pro
            190                 195                 200 caa gag gct cta gag ttt atg cat ata aca cat gag ttg ttt tgg tta               2415
Gln Glu Ala Leu Glu Phe Met His Ile Thr His Glu Leu Phe Trp Leu
            205                 210                 215 cta ggc ttg att tac ttg ggt gat tat ttg cct ttt tgg agg tgg gtt               2463
Leu Gly Leu Ile Tyr Leu Gly Asp Tyr Leu Pro Phe Trp Arg Trp Val
        220                 225                 230 gat cca tat gga tgt gaa aag aaa atg agg gaa gtt gaa aaa agg gta               2511
Asp Pro Tyr Gly Cys Glu Lys Lys Met Arg Glu Val Glu Lys Arg Val
235                 240                 245                 250 gat gat ttc cat cgc aaa att ata gag gaa cat agg aag gag aag aaa               2559
Asp Asp Phe His Arg Lys Ile Ile Glu Glu His Arg Lys Glu Lys Lys
                255                 260                 265 agg aaa gaa gaa atg gga gtg aat gag ggt gaa atg gat ttt gta gat               2607
Arg Lys Glu Glu Met Gly Val Asn Glu Gly Glu Met Asp Phe Val Asp
            270                 275                 280 att ttg ttg gct ttg cct ggt gaa aat gga aat gag cat atg gat gat               2655
Ile Leu Leu Ala Leu Pro Gly Glu Asn Gly Asn Glu His Met Asp Asp
            285                 290                 295 gca gat att aaa gct cta att cag gtaattcatg tataatttga atgtgatcga              2709
Ala Asp Ile Lys Ala Leu Ile Gln
            300                 305 tacaaagttt gatagaaaac atatttgcat aaatatatgg ttgccctact agacccaata            2769
aaatacataa ttattgcctt actagttgaa agttgaaaca acctagctac cattttgttg            2829
tgattatcat tagccaacca aaattatttc ttgcatccat atattaatgt tgagatcaga            2889
gtcggcatat ttcaattac ttgtaacatt ttaagcaaac aaattaaaat attttttggc             2949
```

-continued

```
aagtccattt tattgaataa tacctatatc ttaaaatgaa ttcttggtca tgtacacttg    3009
cctttcaagg taccaatatt tgaccatatg taattactat taacaaattt gataaaatct    3069
aataatatgt aaatatacat tcacgcacat attagaaaca aagatcacaa atgataatgc    3129
aaaataactt atttgaacta atgttgtgaa gttaaatttg gaacaaaagg tatatttgta    3189
ttgccgaatt ttaatttata aattacttat aacaacaact caatatgtaa aactgttaag    3249
atggagtgtg gatagaatga gatgagtata cttttactag ttaccactcg aaaatgcatt    3309
tcctcctttg tttatagttg ttctaacttc tattatcata ataatttttt tggacttatt    3369
tcaatgtata tttacaacgc taattgttta atttttttaaa aatacataat gtaaacaagg   3429
atttcatggt caattataca cattataaat attatcttaa aaaacttatt aatgctcaat    3489
```
tagtatccat aatatag gat atg ata gca gca gca aca gac aca tca gct    3539
                    Asp Met Ile Ala Ala Ala Thr Asp Thr Ser Ala
                            310                 315 gta acc aac gaa tgg gcc atg gca gaa gta ata aaa cac cca cgt gtc    3587
Val Thr Asn Glu Trp Ala Met Ala Glu Val Ile Lys His Pro Arg Val
    320                    325                 330 ctc cac aag atc caa caa gag ctt aac aca ata gta gga ccc aat cga    3635
Leu His Lys Ile Gln Gln Glu Leu Asn Thr Ile Val Gly Pro Asn Arg
    335                    340                 345 atg gta aca gaa tca gat ctt ccc cac ctt aac tac cta cgt tgt gtc    3683
Met Val Thr Glu Ser Asp Leu Pro His Leu Asn Tyr Leu Arg Cys Val
350                    355                 360               365 gta cgt gaa acg ttc cga atg cat cca gca gga ccc ttt tta atc cca    3731
Val Arg Glu Thr Phe Arg Met His Pro Ala Gly Pro Phe Leu Ile Pro
               370                 375               380 cat gaa tca cta cgc cat aca aca atc aac ggc tat gat atc cca tct    3779
His Glu Ser Leu Arg His Thr Thr Ile Asn Gly Tyr Asp Ile Pro Ser
             385                 390               395 ggg aca cgt gtc ttc atc aac aca cat ggg tta gga cgt aac ctt aaa    3827
Gly Thr Arg Val Phe Ile Asn Thr His Gly Leu Gly Arg Asn Leu Lys
            400                 405               410 gtg tgg gac aac ata gag gat ttt tac cct gaa aga cat tgg ccg ttg    3875
Val Trp Asp Asn Ile Glu Asp Phe Tyr Pro Glu Arg His Trp Pro Leu
    415                    420                 425 gat gga agt aga gtt gag att agc cat gga tct gat ttt aaa ata tta    3923
Asp Gly Ser Arg Val Glu Ile Ser His Gly Ser Asp Phe Lys Ile Leu
430                    435                 440               445 cca ttt agt gct ggg aag aga aga tgt cct ggg gcc cca ctt ggg gtg    3971
Pro Phe Ser Ala Gly Lys Arg Arg Cys Pro Gly Ala Pro Leu Gly Val
               450                 455               460 gtg ttt gtg ttg atg gga ttg gct aca ctt ttt cat gca ttt gat tgg    4019
Val Phe Val Leu Met Gly Leu Ala Thr Leu Phe His Ala Phe Asp Trp
            465                 470               475 tta cca cct gat gga atg aag gca gaa gaa att gat act aag gaa gtt    4067
Leu Pro Pro Asp Gly Met Lys Ala Glu Glu Ile Asp Thr Lys Glu Val
    480                    485                 490 tat ggg atg act atg cct aaa gct caa cct tta atg gct ttg gct aaa    4115
Tyr Gly Met Thr Met Pro Lys Ala Gln Pro Leu Met Ala Leu Ala Lys
          495                  500                505 cct agg ctt gct cat tta tat ctt tga tacatgttca tattgtggtg    4162
Pro Arg Leu Ala His Leu Tyr Leu
510                  515

```
cacttataag cacaatagac aaatacaagt ttgtatcgac tctaacatgt tgtttagtat    4222
tagtatactg caactctaca agtatgtaat ttctataaac tataaacaca agtcataacg    4282
cattttgttt tgaaaaaaaa gaggttacat tgtcttacac cataaa                  4328
```

-continued

```
<210> SEQ ID NO 2
<211> LENGTH: 1930
<212> TYPE: DNA
<213> ORGANISM: Artificial Sequence
<220> FEATURE:
<223> OTHER INFORMATION: cDNA-CYPgst gene (Beta vulgaris)
<220> FEATURE:
<221> NAME/KEY: 5'UTR
<222> LOCATION: (1)..(243)
<220> FEATURE:
<221> NAME/KEY: exon
<222> LOCATION: (244)..(1161)
<223> OTHER INFORMATION: Exon 1
<220> FEATURE:
<221> NAME/KEY: exon
<222> LOCATION: (1162)..(1797)
<223> OTHER INFORMATION: Exon 2
<220> FEATURE:
<221> NAME/KEY: 3'UTR
<222> LOCATION: (1798)..(1930)

<400> SEQUENCE: 2
```

| | |
|---|---:|
| ttaaaaaaat aattatattt ctttatactt tattaaccta ttgaggtttt tatattgact | 60 |
| cccaaatact attttataga tcatgccatg ttaatgagca aactactttc tcacatcttt | 120 |
| ataggagaaa aagtagatca ctcactagca tatcatgacc agcgaaacca accaacgcta | 180 |
| atagttttat tgcttccatt agagataaga gttaactaat aataccatct ttgtgaaatt | 240 |

| | | |
|---|---|---:|
| ttg atg gat ttt gga act tta gca ata tat tta ctg tgt gca ctt ttt<br>    Met Asp Phe Gly Thr Leu Ala Ile Tyr Leu Leu Cys Ala Leu Phe<br>    1                    5                      10                  15 | | 288 |
| gct acc aaa att tta tac caa tgg ctc aag tcc tac tta tac aca aca<br>Ala Thr Lys Ile Leu Tyr Gln Trp Leu Lys Ser Tyr Leu Tyr Thr Thr<br>                  20                      25                      30 | | 336 |
| tac aaa ctc cct ccc ggc cca cca agg tgg ccc tta ttt gga aac ctc<br>Tyr Lys Leu Pro Pro Gly Pro Pro Arg Trp Pro Leu Phe Gly Asn Leu<br>                      35                      40                      45 | | 384 |
| ctt caa cta ggg cca ctt ccc cac cgc gat ttc gcc tca ttt tgt gaa<br>Leu Gln Leu Gly Pro Leu Pro His Arg Asp Phe Ala Ser Phe Cys Glu<br>           50                      55                      60 | | 432 |
| aaa tat ggg cct tta gtc tac ata agg ctt ggt aat gtg gat gcc ata<br>Lys Tyr Gly Pro Leu Val Tyr Ile Arg Leu Gly Asn Val Asp Ala Ile<br> 65                    70                      75 | | 480 |
| acc act aat gat cca gaa atc ata cgt gag atc tta gtt cga caa gat<br>Thr Thr Asn Asp Pro Glu Ile Ile Arg Glu Ile Leu Val Arg Gln Asp<br> 80                    85                      90                      95 | | 528 |
| gat gta ttt gcg tct cgt cca cat acc tta gcc gca acc cac ttg gct<br>Asp Val Phe Ala Ser Arg Pro His Thr Leu Ala Ala Thr His Leu Ala<br>                  100                      105                      110 | | 576 |
| tac aat agt ggt gat gtg gcc ttg gct cca atg gga cca aaa tgg aaa<br>Tyr Asn Ser Gly Asp Val Ala Leu Ala Pro Met Gly Pro Lys Trp Lys<br>                  115                      120                      125 | | 624 |
| aga atg aga agg ata tgc atg gag cac ttg ctc aca act aga cga ctt<br>Arg Met Arg Arg Ile Cys Met Glu His Leu Leu Thr Thr Arg Arg Leu<br>           130                      135                      140 | | 672 |
| gaa cta ttt gtg agt cat agg gct gat gag gca cga cat ttg gtc caa<br>Glu Leu Phe Val Ser His Arg Ala Asp Glu Ala Arg His Leu Val Gln<br>145                    150                      155 | | 720 |
| gac gta tta act cgt tcc cac aaa gat aaa gtt gtt aat ttg agg gaa<br>Asp Val Leu Thr Arg Ser His Lys Asp Lys Val Val Asn Leu Arg Glu<br>160                    165                      170                      175 | | 768 |
| gtg tta ggt gca ttt tct atg aat aac gtg act aga atg ttg cta ggg<br>Val Leu Gly Ala Phe Ser Met Asn Asn Val Thr Arg Met Leu Leu Gly | | 816 |

```
                        180                 185                 190
aag caa tac ttt ggg gcc ggg acg gcg ggc cca caa gag gct cta gag      864
Lys Gln Tyr Phe Gly Ala Gly Thr Ala Gly Pro Gln Glu Ala Leu Glu
            195                 200                 205 ttt atg cat ata aca cat gag ttg ttt tgg tta cta ggc ttg att tac      912
Phe Met His Ile Thr His Glu Leu Phe Trp Leu Leu Gly Leu Ile Tyr
        210                 215                 220 ttg ggt gat tat ttg cct ttt tgg agg tgg gtt gat cca tat gga tgt      960
Leu Gly Asp Tyr Leu Pro Phe Trp Arg Trp Val Asp Pro Tyr Gly Cys
    225                 230                 235 gaa aag aaa atg agg gaa gtt gaa aaa agg gta gat gat ttc cat cgc     1008
Glu Lys Lys Met Arg Glu Val Glu Lys Arg Val Asp Asp Phe His Arg
240                 245                 250                 255 aaa att ata gag gaa cat agg aag gag aag aaa agg aaa gaa gaa atg     1056
Lys Ile Ile Glu Glu His Arg Lys Glu Lys Lys Arg Lys Glu Glu Met
                260                 265                 270 gga gtg aat gag ggt gaa atg gat ttt gta gat att ttg ttg gct ttg     1104
Gly Val Asn Glu Gly Glu Met Asp Phe Val Asp Ile Leu Leu Ala Leu
            275                 280                 285 cct ggt gaa aat gga aat gag cat atg gat gat gca gat att aaa gct     1152
Pro Gly Glu Asn Gly Asn Glu His Met Asp Asp Ala Asp Ile Lys Ala
        290                 295                 300 cta att cag gat atg ata gca gca gca aca gac aca tca gct gta acc     1200
Leu Ile Gln Asp Met Ile Ala Ala Ala Thr Asp Thr Ser Ala Val Thr
    305                 310                 315 aac gaa tgg gcc atg gca gaa gta ata aaa cac cca cgt gtc ctc cac     1248
Asn Glu Trp Ala Met Ala Glu Val Ile Lys His Pro Arg Val Leu His
320                 325                 330                 335 aag atc caa caa gag ctt aac aca ata gta gga ccc aat cga atg gta     1296
Lys Ile Gln Gln Glu Leu Asn Thr Ile Val Gly Pro Asn Arg Met Val
                340                 345                 350 aca gaa tca gat ctt ccc cac ctt aac tac cta cgt tgt gtc gta cgt     1344
Thr Glu Ser Asp Leu Pro His Leu Asn Tyr Leu Arg Cys Val Val Arg
            355                 360                 365 gaa acg ttc cga atg cat cca gca gga ccc ttt tta atc cca cat gaa     1392
Glu Thr Phe Arg Met His Pro Ala Gly Pro Phe Leu Ile Pro His Glu
        370                 375                 380 tca cta cgc cat aca aca atc aac ggc tat gat atc cca tct ggg aca     1440
Ser Leu Arg His Thr Thr Ile Asn Gly Tyr Asp Ile Pro Ser Gly Thr
    385                 390                 395 cgt gtc ttc atc aac aca cat ggg tta gga cgt aac ctt aaa gtg tgg     1488
Arg Val Phe Ile Asn Thr His Gly Leu Gly Arg Asn Leu Lys Val Trp
400                 405                 410                 415 gac aac ata gag gat ttt tac cct gaa aga cat tgg ccg ttg gat gga     1536
Asp Asn Ile Glu Asp Phe Tyr Pro Glu Arg His Trp Pro Leu Asp Gly
                420                 425                 430 agt aga gtt gag att agc cat gga tct gat ttt aaa ata tta cca ttt     1584
Ser Arg Val Glu Ile Ser His Gly Ser Asp Phe Lys Ile Leu Pro Phe
            435                 440                 445 agt gct ggg aag aga aga tgt cct ggg gcc cca ctt ggg gtg gtg ttt     1632
Ser Ala Gly Lys Arg Arg Cys Pro Gly Ala Pro Leu Gly Val Val Phe
        450                 455                 460 gtg ttg atg gga ttg gct aca ctt ttt cat gca ttt gat tgg tta cca     1680
Val Leu Met Gly Leu Ala Thr Leu Phe His Ala Phe Asp Trp Leu Pro
    465                 470                 475 cct gat gga atg aag gca gaa gaa att gat act aag gaa gtt tat ggg     1728
Pro Asp Gly Met Lys Ala Glu Glu Ile Asp Thr Lys Glu Val Tyr Gly
480                 485                 490                 495 atg act atg cct aaa gct caa cct tta atg gct ttg gct aaa cct agg     1776
```

```
Met Thr Met Pro Lys Ala Gln Pro Leu Met Ala Leu Ala Lys Pro Arg
            500                 505                 510 ctt gct cat tta tat ctt tga tacatgttca tattgtggtg cacttataag      1827
Leu Ala His Leu Tyr Leu
                515 cacaatagac aaatacaagt ttgtatcgac tctaacatgt tgtttagtat tagtatactg  1887 caactctaca agtatgtaat ttctataaac tataaacaca agt                    1930

<210> SEQ ID NO 3
<211> LENGTH: 517
<212> TYPE: PRT
<213> ORGANISM: Beta vulgaris
<220> FEATURE:
<221> NAME/KEY: PEPTIDE
<222> LOCATION: (1)..(517)
<223> OTHER INFORMATION: protein CYPgst (Beta vulgaris)

<400> SEQUENCE: 3

Met Asp Phe Gly Thr Leu Ala Ile Tyr Leu Leu Cys Ala Leu Phe Ala
1               5                   10                  15

Thr Lys Ile Leu Tyr Gln Trp Leu Lys Ser Tyr Leu Tyr Thr Thr Tyr
            20                  25                  30

Lys Leu Pro Pro Gly Pro Pro Arg Trp Pro Leu Phe Gly Asn Leu Leu
        35                  40                  45

Gln Leu Gly Pro Leu Pro His Arg Asp Phe Ala Ser Phe Cys Glu Lys
    50                  55                  60

Tyr Gly Pro Leu Val Tyr Ile Arg Leu Gly Asn Val Asp Ala Ile Thr
65                  70                  75                  80

Thr Asn Asp Pro Glu Ile Ile Arg Glu Ile Leu Val Arg Gln Asp Asp
                85                  90                  95

Val Phe Ala Ser Arg Pro His Thr Leu Ala Ala Thr His Leu Ala Tyr
            100                 105                 110

Asn Ser Gly Asp Val Ala Leu Ala Pro Met Gly Pro Lys Trp Lys Arg
        115                 120                 125

Met Arg Arg Ile Cys Met Glu His Leu Leu Thr Thr Arg Arg Leu Glu
130                 135                 140

Leu Phe Val Ser His Arg Ala Asp Glu Ala Arg His Leu Val Gln Asp
145                 150                 155                 160

Val Leu Thr Arg Ser His Lys Asp Lys Val Val Asn Leu Arg Glu Val
                165                 170                 175

Leu Gly Ala Phe Ser Met Asn Asn Val Thr Arg Met Leu Leu Gly Lys
            180                 185                 190

Gln Tyr Phe Gly Ala Gly Thr Ala Gly Pro Gln Glu Ala Leu Glu Phe
        195                 200                 205

Met His Ile Thr His Glu Leu Phe Trp Leu Leu Gly Leu Ile Tyr Leu
210                 215                 220

Gly Asp Tyr Leu Pro Phe Trp Arg Trp Val Asp Pro Tyr Gly Cys Glu
225                 230                 235                 240

Lys Lys Met Arg Glu Val Glu Lys Arg Val Asp Asp Phe His Arg Lys
                245                 250                 255

Ile Ile Glu Glu His Arg Lys Glu Lys Lys Arg Lys Glu Glu Met Gly
            260                 265                 270

Val Asn Glu Gly Glu Met Asp Phe Val Asp Ile Leu Leu Ala Leu Pro
        275                 280                 285

Gly Glu Asn Gly Asn Glu His Met Asp Asp Ala Asp Ile Lys Ala Leu
290                 295                 300
```

-continued

Ile Gln Asp Met Ile Ala Ala Thr Asp Thr Ser Ala Val Thr Asn
305                 310                 315                 320

Glu Trp Ala Met Ala Glu Val Ile Lys His Pro Arg Val Leu His Lys
                325                 330                 335

Ile Gln Gln Glu Leu Asn Thr Ile Val Gly Pro Asn Arg Met Val Thr
            340                 345                 350

Glu Ser Asp Leu Pro His Leu Asn Tyr Leu Arg Cys Val Val Arg Glu
        355                 360                 365

Thr Phe Arg Met His Pro Ala Gly Pro Phe Leu Ile Pro His Glu Ser
    370                 375                 380

Leu Arg His Thr Thr Ile Asn Gly Tyr Asp Ile Pro Ser Gly Thr Arg
385                 390                 395                 400

Val Phe Ile Asn Thr His Gly Leu Gly Arg Asn Leu Lys Val Trp Asp
                405                 410                 415

Asn Ile Glu Asp Phe Tyr Pro Glu Arg His Trp Pro Leu Asp Gly Ser
            420                 425                 430

Arg Val Glu Ile Ser His Gly Ser Asp Phe Lys Ile Leu Pro Phe Ser
        435                 440                 445

Ala Gly Lys Arg Arg Cys Pro Gly Ala Pro Leu Gly Val Val Phe Val
    450                 455                 460

Leu Met Gly Leu Ala Thr Leu Phe His Ala Phe Asp Trp Leu Pro Pro
465                 470                 475                 480

Asp Gly Met Lys Ala Glu Glu Ile Asp Thr Lys Glu Val Tyr Gly Met
                485                 490                 495

Thr Met Pro Lys Ala Gln Pro Leu Met Ala Leu Ala Lys Pro Arg Leu
            500                 505                 510

Ala His Leu Tyr Leu
        515

<210> SEQ ID NO 4
<211> LENGTH: 27
<212> TYPE: DNA
<213> ORGANISM: Artificial Sequence
<220> FEATURE:
<223> OTHER INFORMATION: s1e5983d14 Forward (Fw) Primer (5' -3')

<400> SEQUENCE: 4
accaaaattt tataccaatg gctcaag                                          27

<210> SEQ ID NO 5
<211> LENGTH: 23
<212> TYPE: DNA
<213> ORGANISM: Artificial Sequence
<220> FEATURE:
<223> OTHER INFORMATION: s1e5983d14 Reverse (Rv) Primer (5' -3')

<400> SEQUENCE: 5
ggccgggagg gagtttgtat gtt                                              23

<210> SEQ ID NO 6
<211> LENGTH: 27
<212> TYPE: DNA
<213> ORGANISM: Artificial Sequence
<220> FEATURE:
<223> OTHER INFORMATION: s1e5983d17 Forward (Fw) Primer (5' -3')

<400> SEQUENCE: 6
agaaatcata cgtgagatct tagttcg                                          27

```
<210> SEQ ID NO 7
<211> LENGTH: 26
<212> TYPE: DNA
<213> ORGANISM: Artificial Sequence
<220> FEATURE:
<223> OTHER INFORMATION: s1e5983d17 Reverse (Rv) Primer (5' -3')

<400> SEQUENCE: 7
ggtatgtgga cgagacgcaa atacat                                          26

<210> SEQ ID NO 8
<211> LENGTH: 4220
<212> TYPE: DNA
<213> ORGANISM: Beta vulgaris
<220> FEATURE:
<221> NAME/KEY: Promotor
<222> LOCATION: (1)..(1353)
<223> OTHER INFORMATION: putativer Promotor
<220> FEATURE:
<221> NAME/KEY: Gen
<222> LOCATION: (1354)..(3542)
<220> FEATURE:
<221> NAME/KEY: exon
<222> LOCATION: (1354)..(1938)
<223> OTHER INFORMATION: verkrztes Exon 1
<220> FEATURE:
<221> NAME/KEY: Intron
<222> LOCATION: (1939)..(2755)
<220> FEATURE:
<221> NAME/KEY: exon
<222> LOCATION: (2756)..(3394)
<223> OTHER INFORMATION: Exon 2
<220> FEATURE:
<221> NAME/KEY: 3'UTR
<222> LOCATION: (3395)..(3542)

<400> SEQUENCE: 8
gtatatcgtt gccacatgtg cgttgaattt ttccttttcc tatcctttcc actccatatt      60
ctcctcaaaa gtgtgtaaaa atccgacaca cgagtagaat gggattgaag tgggtcaaga     120
tctgaaacca atgggtcaat gccacaaaat aaggtaaggt ttctcgcagt agcaaaaaaa     180
taaagttaag ttgagagaaa aattatgaat agttgtttct cgtgaagagt tgtatacaaa     240
aaaagtctaa tttgatacat tttcttttac atttataaag gattgaccaa tcatccaaat     300
taccaaatat ttaggatata atctttcag attacaaccc atatgtgata cactaaattt      360
tacatgaggc aatggaggat ttgcatgaat atcgaggaga gaaaaaatta gttacaaaac     420
ttgcataatt tatccaaacc aaatcaagtc aagaaacaac gaacaatatt atcattagta     480
ctataagtat atattatagg cttagagcaa agccctaact accacactgc acacaaatga     540
taactagtaa gagaggaaaa tacaaattta agattcaaca tagcaaatta ttcatgattc     600
atgattcatg attcatgatt catgattcac gaacatcaag aatggtatag ctgataaagg     660
acaatttaaa cataagtgta aagctcgcac atcatcaatt atattcgcat actactagac     720
caatctttac ttagtacatg tgttagtaca tgtgttactt catatcagat gtattgattg     780
ttgccaatga catatcatgt tcacttaatc ttagggccat ttaattataa catggagaat     840
aatacaactt aaaattatgt ggtggctatc atctcatttt ctagataatt aaaccttttat    900 tttgtataca tatatattgt ctttacatag caaaacaata ttgaaggtat aacaaccttt     960 ccctttttctt ttactacatg tttatgttag agttttttcga tttacgattg tggtaaatta   1020
attgtaattg atcggttgtc ttgtagtcaa gaaatgacgt atgaatcaat ttagggcatg    1080
ttctcttcgg cataaaacag ctgaactgaa ttgaactgaa ctgaaatgaa tagtgatatg    1140
```

| | |
|---|---|
| tgagagtaaa agtattgtca agagctgaac tgagctgaac tgaacggatc tgaactgaac | 1200 |
| tgatctaatc tgaactaatc tgaactgaac tgaactgaat tgaactgaaa ataagctagg | 1260 |
| gaaaacagac ccttactact attatataac ctcgtttaaa tattaggaaa ttaaaaaaat | 1320 |

```
aattatattt ctttatactt tattaaccta tta tac aat agt ggt gat gtg gcc   1374
                                    Tyr Asn Ser Gly Asp Val Ala
                                    1               5 ttg gct cca atg gga cca aaa tgg aaa aga atg aga agg ata tgc atg   1422
Leu Ala Pro Met Gly Pro Lys Trp Lys Arg Met Arg Arg Ile Cys Met
        10                  15                  20 gag cac ttg ctc aca act aga cga ctt gaa cta ttt gtg agt cat agg   1470
Glu His Leu Leu Thr Thr Arg Arg Leu Glu Leu Phe Val Ser His Arg
25                  30                  35 gct gat gag gca cga cat ttg gtc caa gac gta tta act cgt tcc cac   1518
Ala Asp Glu Ala Arg His Leu Val Gln Asp Val Leu Thr Arg Ser His
40                  45                  50                  55 aaa gat aaa gtt gtt aat ttg agg gaa gtg tta ggt gca ttt tct atg   1566
Lys Asp Lys Val Val Asn Leu Arg Glu Val Leu Gly Ala Phe Ser Met
                60                  65                  70 aat aac gtg act aga atg ttg cta ggg aag caa tac ttt ggg gcc ggg   1614
Asn Asn Val Thr Arg Met Leu Leu Gly Lys Gln Tyr Phe Gly Ala Gly
        75                  80                  85 acg gcg ggc cca caa gag gct cta gag ttt atg cat ata aca cat gag   1662
Thr Ala Gly Pro Gln Glu Ala Leu Glu Phe Met His Ile Thr His Glu
        90                  95                  100 ttg ttt tgg tta cta ggc ttg att tac ttg ggt gat tat ttg cct ttt   1710
Leu Phe Trp Leu Leu Gly Leu Ile Tyr Leu Gly Asp Tyr Leu Pro Phe
        105                 110                 115 tgg agg tgg gtt gat cca tat gga tgt gaa aag aaa atg agg gaa gtt   1758
Trp Arg Trp Val Asp Pro Tyr Gly Cys Glu Lys Lys Met Arg Glu Val
120                 125                 130                 135 gaa aaa agg gta gat gat ttc cat cgc aaa att ata gag gaa cat agg   1806
Glu Lys Arg Val Asp Asp Phe His Arg Lys Ile Ile Glu Glu His Arg
                140                 145                 150 aag gag aag aaa agg aaa gaa gaa atg gga gtg aat gag ggt gaa atg   1854
Lys Glu Lys Lys Arg Lys Glu Glu Met Gly Val Asn Glu Gly Glu Met
        155                 160                 165 gat ttt gta gat att ttg ttg gct ttg cct ggt gaa aat gga aat gag   1902
Asp Phe Val Asp Ile Leu Leu Ala Leu Pro Gly Glu Asn Gly Asn Glu
        170                 175                 180 cat atg gat gat gca gat att aaa gct cta att cag gtaattcatg        1948
His Met Asp Asp Ala Asp Ile Lys Ala Leu Ile Gln
        185                 190                 195
```

| | |
|---|---|
| tataatttga atgtgataca aagtttgata gaaaacatat ttgcataaat acatggttac | 2008 |
| cctactagac ccaataaaat acataattat tgccttgcta gttgaaagtt gaaacaacct | 2068 |
| agctaccatt ttgttgtgat tatcattagc caaccaaaac tatttcttgc atccatatat | 2128 |
| taatgttgag agtcgccata tttcaatta cttgtaacat tttgagcaaa caaattaaaa | 2188 |
| tattttttgg caagtccatt ttattgaatg atacctatat cttaaaatga atccttggtt | 2248 |
| atgtacactt gcctttcaag gtaccaatat ttgaccatat gtaattacta ttaacaaatt | 2308 |
| tgataaaatc taataaatg taaatatacg ttcacgcaca tattagaaac aaagatcaca | 2368 |
| aatgataatg caaataact tatttgaact aatgttgtga agttaaattt ggaacaaaag | 2428 |
| gtatatttgt attgccgaat tttaatttat aaattactta taacaacaac tcaatatgta | 2488 |
| aaactgttaa gatggagtgt ggatagaatg agatgagtat actttactag ttaccactc | 2548 |
| gaaattgcat ttcctccttt gtttatagtt gttctaactt ctattatcat aaataatttt | 2608 |

```
tggacttatt tcaatgtata tttacaacgt taattgttta attttttaaa aatacataat    2668
gtaaacaagg atttcatggt caattataca cattatagat attatcttaa aaacttact     2728 aatgctcaat tagtgtccat aatatag gat atg ata gca gca gca aca gac aca   2782
                              Asp Met Ile Ala Ala Ala Thr Asp Thr
                                              200 tca gct gta acc aac gaa tgg gcc atg gca gaa gta ata aaa cac cca      2830
Ser Ala Val Thr Asn Glu Trp Ala Met Ala Glu Val Ile Lys His Pro
205                 210                 215                 220 cgt gtc ctc cac aag atc caa caa gag ctt aac aca ata gta gga ccc      2878
Arg Val Leu His Lys Ile Gln Gln Glu Leu Asn Thr Ile Val Gly Pro
                225                 230                 235 aat cga atg gta aca gaa tca gat ctt ccc cac ctt aac tac cta cgt      2926
Asn Arg Met Val Thr Glu Ser Asp Leu Pro His Leu Asn Tyr Leu Arg
            240                 245                 250 tgt gtc gta cgc gaa acg ttt cgg atg cat cca gca gga ccc ttt tta      2974
Cys Val Val Arg Glu Thr Phe Arg Met His Pro Ala Gly Pro Phe Leu
        255                 260                 265 atc cca cat gaa tca cta cgc cat aca aca atc aac ggc tat gat atc      3022
Ile Pro His Glu Ser Leu Arg His Thr Thr Ile Asn Gly Tyr Asp Ile
    270                 275                 280 cca tct ggg aca cgt gtc ttc atc aac aca cat ggg tta gga cgt aac      3070
Pro Ser Gly Thr Arg Val Phe Ile Asn Thr His Gly Leu Gly Arg Asn
285                 290                 295                 300 ctt aaa gtg tgg gac aac ata gag gat ttt tac cct gaa aga cat tgg      3118
Leu Lys Val Trp Asp Asn Ile Glu Asp Phe Tyr Pro Glu Arg His Trp
                305                 310                 315 ccg ttg gat gga agt aga gtt gag att agc cat gga tct gat ttt aaa      3166
Pro Leu Asp Gly Ser Arg Val Glu Ile Ser His Gly Ser Asp Phe Lys
                320                 325                 330 ata tta cca ttt agt gct ggg aag aga aga tgt cct ggg gcc cca ctt      3214
Ile Leu Pro Phe Ser Ala Gly Lys Arg Arg Cys Pro Gly Ala Pro Leu
            335                 340                 345 ggg gtg gtg ttt gtg ttg atg gga ttg gct aca ctt ttt cat gca ttt      3262
Gly Val Val Phe Val Leu Met Gly Leu Ala Thr Leu Phe His Ala Phe
        350                 355                 360 gat tgg tta cca cct gat gga atg aag gca gaa gaa att gat act aag      3310
Asp Trp Leu Pro Pro Asp Gly Met Lys Ala Glu Glu Ile Asp Thr Lys
365                 370                 375                 380 gaa gtt tat ggg atg act atg cct aaa gct caa cct tta atg gct ttg      3358
Glu Val Tyr Gly Met Thr Met Pro Lys Ala Gln Pro Leu Met Ala Leu
                385                 390                 395 gct aaa cct agg ctt gct cct cat tta tat ctt tga tacatgttca           3404
Ala Lys Pro Arg Leu Ala Pro His Leu Tyr Leu
                400                 405 tattgtggtg cacttataag cacactagct caaatagaca aatacaagct tgtattgact    3464
ctaacatgtt atttaatatt agcatactgc aactctacaa ctacaagtat gtaatctcta    3524
taaattataa acataagtca taacgcatct tgttttgaaa aaaaaagcta cactttctta    3584
caccataaac tgttccgtta ctaaattctt cttggcttat tttagaatta attttcaat     3644 tttcctattt acttataaca caagataaga aaatcgacta acaatatttc acaacattat    3704
atcttgatag ttcgttgaaa ttaataattt tcaataattt caaaacgcaa aaagcttctt    3764
tgttcggata aattcacgtc atttcaata aaatcgcaaa atcttccctt gccatcaagg     3824
aacaaatttt tcacatcaaa actcttcttc caaaaagtat acttctccat tgattatgta    3884
aaagagtttg catgttctaa tccattagta tgtatttttc ggataagaag ttgtattaca    3944
```

-continued

```
agcttaaata aagatataaa cttagttaaa tatcgaccaa tccacaatat gtatcttcat    4004
atgtgtccat cagcgcctaa ccttgagatg tagatcatct aaagcacatt aacatggcgt    4064
actcctcctg ttcaaatcag ggttgtttga aaccaaactt ctccaaaata cttcctcagt    4124
aatgaagaga aaaactcaca ttctgaaaaa catcaacatc atggttctat ggtctagtgg    4184
ttatgacact ggactctgaa tccagtaacc cgagtt                              4220
```

<210> SEQ ID NO 9
<211> LENGTH: 4068
<212> TYPE: DNA
<213> ORGANISM: Zea mays
<220> FEATURE:
<221> NAME/KEY: exon
<222> LOCATION: (2001)..(2927)
<223> OTHER INFORMATION: Exon 1
<220> FEATURE:
<221> NAME/KEY: Intron
<222> LOCATION: (2928)..(3017)
<223> OTHER INFORMATION: Intron
<220> FEATURE:
<221> NAME/KEY: exon
<222> LOCATION: (3018)..(3683)
<223> OTHER INFORMATION: Exon 2

<400> SEQUENCE: 9

```
gagtgtggtg cgttggtttt gtcagatgtc acaggaagga tgcagaccta ataccgctgc      60
ttttagttgt ttgctgagtg ctttggctag cctggctatg ctgaatcagg gattgcaagc     120
tcatgcttat gcagtcaaca tgggatggat atttgactca gctgtccatg cttctttggt     180
gacaatgtat gcaaaatgtg gtaggttggc tgaggctcat cgtgttttct catgcattag     240
aaatccaagc cttgttgcca ttaattctat gatttcagca tttgcacaac atggcttggc     300
tgaagatgca ctcaaacttt ttaacagaat gcaatatgat ggccaaaggc ctaatcatgt     360
gacattcttg ggaatactga ctgcatgtgc tcgagctggt ttggttcaac aaggctataa     420
ctactttgaa tctatgagat cagtctatgg cattcaacca aaccctgacc actacacatg     480
tatggttaat ctttaggcc atgcaggctt ccttgatgaa gcattggaaa tgattaattc      540
gatgccccag aaagattatc ctgatgcatg ggcagctttg cttagctcta gtagcctcca    600
ttctaatctt gatttagcaa aactagcagc acagaggctt cttgagatag atccttatga     660
cacaacagct tacagggtcc tgacaaacat gttctcctca gcagggttga agggagatga     720
agagatggta aaagttgcac aattgtccaa catggctagt aagaggcctg ggtatagcct     780
catcatacag gataagacta cagaaaataa ctagcccaaa atgagcactt ccatttacag     840
ataactggca tgtcataact cataagacag ggatattggg ttcacagaaa acaattctag     900
cgccaagatg agatatcaat ttgttgatgt atgctagtgc agagtcagtt ttagtactta     960
agaactgaga atgaggaata tctgataagg tgactagtga tttgaagaat aaagagccag    1020
gtggtctgga tcaaattttg gttagtcttg cctcttatat cactgtttcc aggatagaat    1080
tttcagtact gcaactgatg ttgtatttga ataatggaaa atatttttc tccctgtaaa     1140 caatagtttt gtcagatgta aatcttatcc acagtagaat atgatgccat ataatgctgt    1200
tcagattcat tacaatcgtg aagtttattg cgccttttc agagactgga gagttgatga     1260
cacttctgca ataattcat ctgctactgt tgttgaacaa caagaaaatc attggttgct     1320
gcatgctttc aagaatattt tgctgcgtga tctatctatt ctcctcatca attgatagag    1380
aagagtcgct gagagaggta atctttatgc ttattcattc atttcgatga gacaaccata    1440
ccaaggtgaa ttgggtgatc cctaggtcta ggcttttctt ttagcaatag aagcttccaa    1500
```

```
gtaattcatg gaggtctaag gatgttctcc tcaagaaaaa tagggattgt ctgtgtcttt    1560
gttatagatg tggcaggtgg agtaggacta tggtaaacaa gggttttctc ttattttttgg   1620 ctgagaaatt gtagattagt ggggaaacta tcctaattat ggcaacataa tgtcagcttg    1680 cttttttgatt aatagtcatg tttcatgacc ttttttttgtt ctagtcctct tctttttttt   1740
tccttggcat tttcccagtg atctacagtt tacattgcgc aagtcatgtc aagatcatga    1800 cagttttttat atacatggtg gtagttgaga tgcttaacca tacacatcaa cacaaaaacc  1860
atgaccaatc taatactgta accaatttgc ttcaacctca gtggctcaat ttacttagta   1920
cttaagcgaa gaagcttgag acgtcccata aataggccag catttgcaat ccaactttag   1980
ctgccatctg tttctgaacc atg gat cca ttt gtt ctc tcc atc ctc tta tgc   2033
                       Met Asp Pro Phe Val Leu Ser Ile Leu Leu Cys
                        1               5                      10 tca tcg atc ttt gtt gta gtg tac tgg aga agg ctg aac agc atg agg   2081
Ser Ser Ile Phe Val Val Val Tyr Trp Arg Arg Leu Asn Ser Met Arg
            15                  20                  25 cta aga ctt cca ccg gga cct cca aca tgg cca att ttc ggc aat ctt   2129
Leu Arg Leu Pro Pro Gly Pro Pro Thr Trp Pro Ile Phe Gly Asn Leu
        30                  35                  40 ctc cag ttg agc cct ctt ccc cac aaa gac ttt gcc caa ttt tgc acc   2177
Leu Gln Leu Ser Pro Leu Pro His Lys Asp Phe Ala Gln Phe Cys Thr
    45                  50                  55 aaa tat ggc cct ctc gtc tat ctt cgc ctg gga acc atc gat gcc atc   2225
Lys Tyr Gly Pro Leu Val Tyr Leu Arg Leu Gly Thr Ile Asp Ala Ile
60                  65                  70                  75 acc act gat gac ccc gaa gtg atc cgt gaa ata ctc atc cgg caa gat   2273
Thr Thr Asp Asp Pro Glu Val Ile Arg Glu Ile Leu Ile Arg Gln Asp
                80                  85                  90 gag gtc ttt gct tcg cgg cct cgg aca ctg gct gcc gtc cat ctc gcc   2321
Glu Val Phe Ala Ser Arg Pro Arg Thr Leu Ala Ala Val His Leu Ala
            95                 100                 105 tat ggg tgt ggt gat gtg gct cta gct cca ctg gga ccc aac tgg aaa   2369
Tyr Gly Cys Gly Asp Val Ala Leu Ala Pro Leu Gly Pro Asn Trp Lys
        110                 115                 120 agg atg agg aga gtt tgc atg gag cac ttg ctg acg acc agg cgg ctc   2417
Arg Met Arg Arg Val Cys Met Glu His Leu Leu Thr Thr Arg Arg Leu
    125                 130                 135 gag tct ttc gct gct cac cga gct cag gag gcc gag cac ctc tgc cag   2465
Glu Ser Phe Ala Ala His Arg Ala Gln Glu Ala Glu His Leu Cys Gln
140                 145                 150                 155 ttt gtg tgg gct aaa tct cag tcc ggg aag ccc gtg aac ctc aga gag   2513
Phe Val Trp Ala Lys Ser Gln Ser Gly Lys Pro Val Asn Leu Arg Glu
                160                 165                 170 gtt ctc ggt gcc ttc tcg atg aac aac gtc acg cgg atg ctg ctg ggg   2561
Val Leu Gly Ala Phe Ser Met Asn Asn Val Thr Arg Met Leu Leu Gly
            175                 180                 185 aag cag tac ttt ggg atc cag tcg gca ggc ccc ggc gag gca atg gag   2609
Lys Gln Tyr Phe Gly Ile Gln Ser Ala Gly Pro Gly Glu Ala Met Glu
        190                 195                 200 ttc atg cac atc acc cac gag ctg ttc ttc ctg ctg ggc ctg atc tat   2657
Phe Met His Ile Thr His Glu Leu Phe Phe Leu Leu Gly Leu Ile Tyr
    205                 210                 215 ctc ggg gac tac ttg ccg gct tgg agg tgg gtc gac ccg tac ggg tgt   2705
Leu Gly Asp Tyr Leu Pro Ala Trp Arg Trp Val Asp Pro Tyr Gly Cys
220                 225                 230                 235 gag aag agg atg agg gag gtg gag aag aag gtg gac gac ttc cac cag   2753
Glu Lys Arg Met Arg Glu Val Glu Lys Lys Val Asp Asp Phe His Gln
```

-continued

```
                    240                 245                 250
aag atc att gat gag cac agg aga gct agg gag gcc agg aag agt cgt      2801
Lys Ile Ile Asp Glu His Arg Arg Ala Arg Glu Ala Arg Lys Ser Arg
            255                 260                 265 tcc tcc gtt gag gaa gat ggc ggc aac ggc aaa gat gag atg gac ttc      2849
Ser Ser Val Glu Glu Asp Gly Gly Asn Gly Lys Asp Glu Met Asp Phe
        270                 275                 280 gtc gat gtg ctg tta tct ttg cct ggt gag aac ggg aag gag cac atg      2897
Val Asp Val Leu Leu Ser Leu Pro Gly Glu Asn Gly Lys Glu His Met
    285                 290                 295 gac gac atg gag atc aaa gcg ttg atg cag gtgtgtgtat gtgtatgctt        2947
Asp Asp Met Glu Ile Lys Ala Leu Met Gln
300                 305 tgctattgca taccctggaa ttcaattcat tttgttgaag ctagttatta tgagtaatac    3007
ttcttggcag gac atg atc gct gct gct act gat act tca tcg gtg acg      3056
              Asp Met Ile Ala Ala Ala Thr Asp Thr Ser Ser Val Thr
                  310                 315                 320 aac gag tgg gtg atg gcg gag gta atc aag aac ccg cgc gtg ctc cgg      3104
Asn Glu Trp Val Met Ala Glu Val Ile Lys Asn Pro Arg Val Leu Arg
            325                 330                 335 cgc gtc cag gag gag ctg gac gcg gtg gtg ggg cgc gac cgg atg gtg      3152
Arg Val Gln Glu Glu Leu Asp Ala Val Val Gly Arg Asp Arg Met Val
        340                 345                 350 gcg gag tcg gac ctg gcc cac ctc ccc tac ctc cgg tgc gtg gtg cgc      3200
Ala Glu Ser Asp Leu Ala His Leu Pro Tyr Leu Arg Cys Val Val Arg
355                 360                 365                 370 gag tca ttc cgg atg cac ccg gcg ggg ccg ttc ctt atc ccg cac gag      3248
Glu Ser Phe Arg Met His Pro Ala Gly Pro Phe Leu Ile Pro His Glu
            375                 380                 385 tcg ctg aag gcg acg acc atc atg ggg tac cac gtg ccg gcg cgc acg      3296
Ser Leu Lys Ala Thr Thr Ile Met Gly Tyr His Val Pro Ala Arg Thr
        390                 395                 400 cgc gtg ttc atc aac acg cac gcg ctg ggg cgg aac ccg cgc gtg tgg      3344
Arg Val Phe Ile Asn Thr His Ala Leu Gly Arg Asn Pro Arg Val Trp
    405                 410                 415 gac tcc gtg ggc gag ttc cgg ccg gag cgg cac ctg ccg gcg gag gag      3392
Asp Ser Val Gly Glu Phe Arg Pro Glu Arg His Leu Pro Ala Glu Glu
420                 425                 430 ggg gcg cgg gtg gag atc agc cac ctg ccg gac ttc aag atc ctg ccg      3440
Gly Ala Arg Val Glu Ile Ser His Leu Pro Asp Phe Lys Ile Leu Pro
435                 440                 445                 450 ttc agc gcc ggg aag cgc aag tgc ccc ggc gcg ccg ctg ggc gtg gcg      3488
Phe Ser Ala Gly Lys Arg Lys Cys Pro Gly Ala Pro Leu Gly Val Ala
            455                 460                 465 ctg gtg ctc atg gcg ctc gcc agg ctc ttc cac tgc ttc gac tgg tcc      3536
Leu Val Leu Met Ala Leu Ala Arg Leu Phe His Cys Phe Asp Trp Ser
        470                 475                 480 ccg ccc gac ggc ctc cgc ccc gag gac gtg gac acc cgg gag gtg tac      3584
Pro Pro Asp Gly Leu Arg Pro Glu Asp Val Asp Thr Arg Glu Val Tyr
    485                 490                 495 ggc atg acc atg ccc aag gcc acg ccc ctc gtc gcc gtc gcc act ccg      3632
Gly Met Thr Met Pro Lys Ala Thr Pro Leu Val Ala Val Ala Thr Pro
500                 505                 510 cgc ctg ccg ccg cac ttg tac ggc ggc ggc ggc agc tcg gct cct          3680
Arg Leu Pro Pro His Leu Tyr Gly Gly Gly Gly Ser Ser Ala Pro
515                 520                 525                 530 tag ttcgatgaca ctttgacgca cgtgcgctgc actgccagtc tcattagtca           3733
ttatacgcat gatgtacttc cctccatata caatacaccg cataaaccaa acgatgaatg    3793
```

| aaatgtagtc gttctatggt ttcaatatga aagatataa ttgatggtta acatcatttc | 3853 |
| cctccgttta gtgataagcc atatactcta ggtatgtagt agtgtaacaa tgcgatccca | 3913 |
| gcccaggtaa cgaggtagca gagaggtgag ctagctgtag ctggcgacga agcgaagcat | 3973 |
| taaacggttg caacggcagc tagccgtggc gttcatgcac ggtatggcca aaaaaaggg | 4033 |
| accctatcca tctgccagtt ttggcgtacc aatgc | 4068 |

<210> SEQ ID NO 10
<211> LENGTH: 1593
<212> TYPE: DNA
<213> ORGANISM: Artificial Sequence
<220> FEATURE:
<223> OTHER INFORMATION: c-DNA CYPgst gene (Zea mays)

<400> SEQUENCE: 10

| atggatccat tgttctctc catcctctta tgctcatcga tctttgttgt agtgtactgg | 60 |
| agaaggctga acagcatgag gctaagactt ccaccgggac ctccaacatg gccaattttc | 120 |
| ggcaatcttc tccagttgag ccctcttccc cacaaagact ttgcccaatt ttgcaccaaa | 180 |
| tatgccctc tcgtctatct tcgcctggga accatcgatg ccatcaccac tgatgacccc | 240 |
| gaagtgatcc gtgaaatact catccggcaa gatgaggtct ttgcttcgcg gcctcggaca | 300 |
| ctggctgccg tccatctcgc ctatgggtgt ggtgatgtgg ctctagctcc actgggaccc | 360 |
| aactggaaaa ggatgaggag agtttgcatg gagcacttgc tgacgaccag gcggctcgag | 420 |
| tctttcgctg ctcaccgagc tcaggaggcc gagcacctct gccagtttgt gtgggctaaa | 480 |
| tctcagtccg ggaagcccgt gaacctcaga gaggttctcg gtgccttctc gatgaacaac | 540 |
| gtcacgcgga tgctgctggg gaagcagtac tttgggatcc agtcggcagg ccccggcgag | 600 |
| gcaatggagt tcatgcacat cacccacgag ctgttcttcc tgctgggcct gatctatctc | 660 |
| ggggactact tgccggcttg gaggtgggtc gacccgtacg ggtgtgagaa gaggatgagg | 720 |
| gaggtggaga agaaggtgga cgacttccac cagaagatca ttgatgagca caggagagct | 780 |
| agggaggcca ggaagagtcg ttcctccgtt gaggaagatg gcggcaacgg caaagatgag | 840 |
| atggacttcg tcgatgtgct gttatctttg cctggtgaga cgggaagga gcacatggac | 900 |
| gacatggaga tcaaagcgtt gatgcaggac atgatcgctg ctgctactga tacttcatcg | 960 |
| gtgacgaacg agtgggtgat ggcggaggta atcaagaacc cgcgcgtgct ccggcgcgtc | 1020 |
| caggaggagc tggacgcggt ggtggggcgc gaccggatgg tggcggagtc ggacctggcc | 1080 |
| cacctccccct acctccggtg cgtggtgcgc gagtcattcc ggatgcaccc ggcggggccc | 1140 |
| ttccttatcc cgcacgagtc gctgaaggcg acgaccatca tggggtacca cgtgccggcg | 1200 |
| cgcacgcgcg tgttcatcaa cacgcacgcg ctggggcgga acccgcgcgt gtgggactcc | 1260 |
| gtgggcgagt tccggccgga gcggcacctg ccggcggagg agggggcgcg ggtggagatc | 1320 |
| agccacctgc cggacttcaa gatcctgccg ttcagcgccg ggaagcgcaa gtccccggc | 1380 |
| gcgccgctgg gcgtggcgct ggtgctcatg gcgctcgcca ggctcttcca ctgcttcgac | 1440 |
| tggtccccgc ccgacggcct ccgccccgag gacgtggaca ccggggaggt gtacggcatg | 1500 |
| accatgccca aggccacgcc cctcgtcgcc gtcgccactc cgcgcctgcc gccgcacttg | 1560 |
| tacggcggcg gcggcggcag ctcggctcct tag | 1593 |

<210> SEQ ID NO 11
<211> LENGTH: 530
<212> TYPE: PRT

```
<213> ORGANISM: Zea mays
<220> FEATURE:
<221> NAME/KEY: PEPTIDE
<222> LOCATION: (1)..(530)
<223> OTHER INFORMATION: protein CYPgst (Zea mays)

<400> SEQUENCE: 11
```

Met Asp Pro Phe Val Leu Ser Ile Leu Leu Cys Ser Ser Ile Phe Val
1               5                   10                  15

Val Val Tyr Trp Arg Arg Leu Asn Ser Met Arg Leu Arg Leu Pro Pro
            20                  25                  30

Gly Pro Pro Thr Trp Pro Ile Phe Gly Asn Leu Leu Gln Leu Ser Pro
            35                  40                  45

Leu Pro His Lys Asp Phe Ala Gln Phe Cys Thr Lys Tyr Gly Pro Leu
        50                  55                  60

Val Tyr Leu Arg Leu Gly Thr Ile Asp Ala Ile Thr Thr Asp Asp Pro
65                  70                  75                  80

Glu Val Ile Arg Glu Ile Leu Ile Arg Gln Asp Glu Val Phe Ala Ser
                85                  90                  95

Arg Pro Arg Thr Leu Ala Ala Val His Leu Ala Tyr Gly Cys Gly Asp
            100                 105                 110

Val Ala Leu Ala Pro Leu Gly Pro Asn Trp Lys Arg Met Arg Arg Val
            115                 120                 125

Cys Met Glu His Leu Leu Thr Thr Arg Arg Leu Glu Ser Phe Ala Ala
130                 135                 140

His Arg Ala Gln Glu Ala Glu His Leu Cys Gln Phe Val Trp Ala Lys
145                 150                 155                 160

Ser Gln Ser Gly Lys Pro Val Asn Leu Arg Glu Val Leu Gly Ala Phe
                165                 170                 175

Ser Met Asn Asn Val Thr Arg Met Leu Leu Gly Lys Gln Tyr Phe Gly
            180                 185                 190

Ile Gln Ser Ala Gly Pro Gly Glu Ala Met Glu Phe Met His Ile Thr
        195                 200                 205

His Glu Leu Phe Phe Leu Leu Gly Leu Ile Tyr Leu Gly Asp Tyr Leu
    210                 215                 220

Pro Ala Trp Arg Trp Val Asp Pro Tyr Gly Cys Glu Lys Arg Met Arg
225                 230                 235                 240

Glu Val Glu Lys Lys Val Asp Asp Phe His Gln Lys Ile Ile Asp Glu
                245                 250                 255

His Arg Arg Ala Arg Glu Ala Arg Lys Ser Arg Ser Ser Val Glu Glu
            260                 265                 270

Asp Gly Gly Asn Gly Lys Asp Glu Met Asp Phe Val Asp Val Leu Leu
        275                 280                 285

Ser Leu Pro Gly Glu Asn Gly Lys Glu His Met Asp Asp Met Glu Ile
    290                 295                 300

Lys Ala Leu Met Gln Asp Met Ile Ala Ala Thr Asp Thr Ser Ser
305                 310                 315                 320

Val Thr Asn Glu Trp Val Met Ala Glu Val Ile Lys Asn Pro Arg Val
                325                 330                 335

Leu Arg Arg Val Gln Glu Glu Leu Asp Ala Val Val Gly Arg Asp Arg
            340                 345                 350

Met Val Ala Glu Ser Asp Leu Ala His Leu Pro Tyr Leu Arg Cys Val
        355                 360                 365

Val Arg Glu Ser Phe Arg Met His Pro Ala Gly Pro Phe Leu Ile Pro
    370                 375                 380

His Glu Ser Leu Lys Ala Thr Thr Ile Met Gly Tyr His Val Pro Ala
385                 390                 395                 400

Arg Thr Arg Val Phe Ile Asn Thr His Ala Leu Gly Arg Asn Pro Arg
            405                 410                 415

Val Trp Asp Ser Val Gly Glu Phe Arg Pro Glu Arg His Leu Pro Ala
        420                 425                 430

Glu Glu Gly Ala Arg Val Glu Ile Ser His Leu Pro Asp Phe Lys Ile
    435                 440                 445

Leu Pro Phe Ser Ala Gly Lys Arg Lys Cys Pro Gly Ala Pro Leu Gly
450                 455                 460

Val Ala Leu Val Leu Met Ala Leu Ala Arg Leu Phe His Cys Phe Asp
465                 470                 475                 480

Trp Ser Pro Pro Asp Gly Leu Arg Pro Glu Asp Val Asp Thr Arg Glu
            485                 490                 495

Val Tyr Gly Met Thr Met Pro Lys Ala Thr Pro Leu Val Ala Val Ala
        500                 505                 510

Thr Pro Arg Leu Pro Pro His Leu Tyr Gly Gly Gly Gly Ser Ser
    515                 520                 525

Ala Pro
    530

<210> SEQ ID NO 12
<211> LENGTH: 4880
<212> TYPE: DNA
<213> ORGANISM: Solanum tuberosum
<220> FEATURE:
<221> NAME/KEY: exon
<222> LOCATION: (1762)..(2032)
<223> OTHER INFORMATION: Exon 1
<220> FEATURE:
<221> NAME/KEY: Intron
<222> LOCATION: (2033)..(2448)
<223> OTHER INFORMATION: Intron 1
<220> FEATURE:
<221> NAME/KEY: exon
<222> LOCATION: (2449)..(3161)
<223> OTHER INFORMATION: Exon 2
<220> FEATURE:
<221> NAME/KEY: Intron
<222> LOCATION: (3162)..(4031)
<223> OTHER INFORMATION: Intron 2
<220> FEATURE:
<221> NAME/KEY: exon
<222> LOCATION: (4032)..(4694)
<223> OTHER INFORMATION: Exon 3

<400> SEQUENCE: 12
ataataaata tttttttta aaaaagagag ggttgttagt tgcaagggta taagtgagca    60
aaaaggtgga tggaaggata attttagacc aaaaagatga gtagaagggt atttttagac   120
caaaagatgg atgaaggata tttttagacc atttcctgta tttcagaggt attttttggcc  180 cttttccgta tgaaatttg aggttgtatt taagttcaat tggtcaaatt aataagtatt   240
tttaagactg tcaaaaattt agaaataaaa ctaataattc acatcaattc tacaaatatt   300 tcttttaat atatagacat tcggttcaag taaaatattt taagttttta tttaatttct   360
tgtttgtttg attatggatt gccttggatt ctatttgcgt aatggaaatg gcagctcttt   420
tcagtgtagg attggacaag ttagcttgga ttttttttca cctactctac aaaaagtgat   480
ggggcgtcca ccaaccatac gtcaacaact tgtccattc tttgtacaca ctaccatcac   540
aatctatcaa aagatttgtt ctttagtctc gtttaacata ttcttccgtt ttcatttaa   600

```
tttatttgtc ttattttttt ttataaaata aaataaatat ttttgatat aatacataaa      660 tatattcttt aatttcattt catttaacat ctctatactt taacttggga gtcgagtgat     720
tgggttggaa gtcaggtcgt gattagaggt taggagttag gtcccaactc ggaattgaga     780
ttagaggtcc agattagatc tcaggttaga gtcgggagtt gggtcttaag ttgtggtcag     840
gatttgggtc ctagttgagg tcacaagtca ggtccccgct cgagatcgaa aattaggtcc     900
cgagttgaga tagaaagttt tttgatcaag attgaggtcg tagtcaagag tcgagttctg     960
agtcgggatt gtaatcggga gtgggtcctt acaggttagg gcgggggtcg aaagtcgggt    1020
ctcaagttag gactcgtttg agggtggtga ggtttaagta ggggtgtgca tcgatcggtt    1080
cggtttatcg attttcagtt tttaaatatg ctaaattaat aaccaaatca aaaggttttt    1140
tttatcgatt ttggtcatta atgactcgat tttctattta accaattaga aaatgctcat    1200
aaaacaaata gatgacttct ctaacaaaat ttgaccgaca agacaagaca ataatgtgat    1260
tattatttta ggttttgacg ttttgtataa tgtgaagtgt gaattgaagg tttaagggca    1320
aagacagtaa ctagtaatat attgagatta atatttatgt aataagtaaa agaagtaaat    1380
tactggagta taatcttatt gagttattgt tttacccaat aacacaatat taaaaatcaa    1440
tatcgaatcg ataacccgat attttttta aaaaaaatt gttaacccaa ttgatgcatt      1500
tttttatata ttcgtaaaat gcgtaaattg cattaaatta ttcccataaa taaaaaagaa    1560
acttgttcat aaattcaaac ttattgtgca aattgaggaa gcaaaaagt gtgatttcaa     1620 gattaatact tatagttgaa acatgtcaag atgatgggct tcctaatcgc tccaaaaaaa    1680
gattataaat tagaattaaa catatttcct tattaagcct ttgtaaacta cttctttctt    1740 tttttttgaca ataattaaa g atg att gac ttg act agt ttt gtt att gtc     1791
                      Met Ile Asp Leu Thr Ser Phe Val Ile Val
                       1               5                    10 ctt ctt tgc acg tat ctt ctt aat ttg atc aat tat agt ata gtc ctt     1839
Leu Leu Cys Thr Tyr Leu Leu Asn Leu Ile Asn Tyr Ser Ile Val Leu
             15                  20                  25 ttt ggc gca tat ctt att tcc aag cta ctt cat ttt tca ttc gtc gat     1887
Phe Gly Ala Tyr Leu Ile Ser Lys Leu Leu His Phe Ser Phe Val Asp
         30                  35                  40 aag tcg aat cga gaa atc aat caa ctc cct cct ggt cca aaa caa tgg     1935
Lys Ser Asn Arg Glu Ile Asn Gln Leu Pro Pro Gly Pro Lys Gln Trp
     45                  50                  55 cct att gta ggc aac ctt ttt cag tta ggg caa tta cct cat cga gac     1983
Pro Ile Val Gly Asn Leu Phe Gln Leu Gly Gln Leu Pro His Arg Asp
 60                  65                  70 atg gcg tct ttc tgc gaa aaa tat ggc cca ttg gtc tat ctc cga cta g   2032
Met Ala Ser Phe Cys Glu Lys Tyr Gly Pro Leu Val Tyr Leu Arg Leu
75                  80                  85                  90 gtaatgttga tacaataaat tcacaaatga ccacaattta gtccttgtaa ttaataaata    2092
gtcattgttt tcgagtttca aatttataag ggaaacttca agtacacttg acttggagat    2152
tcacttatgg atgttgcaac tcgatgaaca attactattt tacaaaaaaa tgatcgaaaa    2212
gtgataagtg ataagtgata agtgaacgtt atttctcata taagttcaa tgctatacag     2272 attcggtcaa actcagtaaa ttttacctaa gtacttatc catgttaaga aaaaatcatt     2332
atatatgtac acacattaaa ttttaaaccg agttattagc actagaattt atcgttctaa    2392
cattttgaac ccataaagtt gatatcgtga ctccaccttt tgttttctct taaaag gt    2450
                                                                Gly aat gtt gat gct atc acc acc aat gat cca gaa atc ata aga gaa ata     2498
Asn Val Asp Ala Ile Thr Thr Asn Asp Pro Glu Ile Ile Arg Glu Ile
```

-continued

```
                  95                  100                 105
ctt gta caa caa gat gat gtt ttt gca tct agg cca aga act ctt gct    2546
Leu Val Gln Gln Asp Asp Val Phe Ala Ser Arg Pro Arg Thr Leu Ala
        110                 115                 120 gcc att cat cta gct tat ggt tgt ggg gat gtg gca ttg gct cct tta    2594
Ala Ile His Leu Ala Tyr Gly Cys Gly Asp Val Ala Leu Ala Pro Leu
125                 130                 135 ggt cca aaa tgg aaa aga atg aga aga ata tgt atg gaa cat tta ttg    2642
Gly Pro Lys Trp Lys Arg Met Arg Arg Ile Cys Met Glu His Leu Leu
140                 145                 150                 155 aca act aaa aga ctt gaa tca ttt gca aaa cat agg gca gat gaa gcc    2690
Thr Thr Lys Arg Leu Glu Ser Phe Ala Lys His Arg Ala Asp Glu Ala
                160                 165                 170 caa agt cta gtt aaa gat att tgg acc aaa gcc caa aaa gga caa ata    2738
Gln Ser Leu Val Lys Asp Ile Trp Thr Lys Ala Gln Lys Gly Gln Ile
            175                 180                 185 gtg aat ttg agg gaa gtt ttg ggt gga ttt tca atg aat aat gtg act    2786
Val Asn Leu Arg Glu Val Leu Gly Gly Phe Ser Met Asn Asn Val Thr
        190                 195                 200 aga atg ttg tta ggt aaa caa tat ttt ggg gca gaa tca gca ggt cca    2834
Arg Met Leu Leu Gly Lys Gln Tyr Phe Gly Ala Glu Ser Ala Gly Pro
205                 210                 215 caa gaa gca atg gaa ttt atg cat gta aca cat gag tta ttt tgg tta    2882
Gln Glu Ala Met Glu Phe Met His Val Thr His Glu Leu Phe Trp Leu
220                 225                 230                 235 ctt gga gtg ata tat tta ggt gat tat tta cct ttt tgg agg tgg att    2930
Leu Gly Val Ile Tyr Leu Gly Asp Tyr Leu Pro Phe Trp Arg Trp Ile
                240                 245                 250 gat cct tat ggt tgt gag aaa aaa atg agg gat gtt gaa aaa agg att    2978
Asp Pro Tyr Gly Cys Glu Lys Lys Met Arg Asp Val Glu Lys Arg Ile
            255                 260                 265 gat gat ttt cat atg aga ata att gaa gaa cat aga aag aag aaa ggt    3026
Asp Asp Phe His Met Arg Ile Ile Glu Glu His Arg Lys Lys Lys Gly
        270                 275                 280 aat aaa aat aat aat aat att gat gat gat gaa atg gac ttt gtg gat    3074
Asn Lys Asn Asn Asn Asn Ile Asp Asp Asp Glu Met Asp Phe Val Asp
285                 290                 295 gtt tta ttg tct cta cca gga gaa gat gaa gga gat ggt aat gga aaa    3122
Val Leu Leu Ser Leu Pro Gly Glu Asp Glu Gly Asp Gly Asn Gly Lys
300                 305                 310                 315 caa aat atg gat gat gta gag att aaa gct cta att cag gtctaatttt    3171
Gln Asn Met Asp Asp Val Glu Ile Lys Ala Leu Ile Gln
                320                 325 ttttatatat accaactttc tacctattta atatgtcaat gcatttatct caaactactt    3231
atatatatat ccaatatata tgcatttggt gagcaacaac taccacccat gggatttcta    3291
agcttgatta acagaggttg tggtgaagtg ataagtactt cttcatccct aactagaggt    3351
cttgggttcg agtcttgctg gatacaaagt cgtctttgtt aaagagtgtt accccataat    3411
gtgagacttt ccggcacgaa tcaaaatttt gttggaatct aatggggtat cgaacaccag    3471
ttgagaaaag aaagagaaga agaaattcct acaatgtggg actttcggga gcgaacccaa    3531
attttgttgg actctaatga gggtatggga cacccgtaga aaaaaaaaga aataaattca    3591
caagtttgat tgatacttaa aacataaaat ttaagttata tatactgata gagtaaaaca    3651
aattacatta ttagtccaat ttaatcggta ctaccatgtt attactctat taaattatta    3711
tatgagactt aatatagaga gttacatgtc aacttgatag tgtagacatt tttagactat    3771
tcatgcacaa aaacttaact ctaatacaat caatttcctt gcaactttta tattagagaa    3831
```

```
tatatatata tatatatata tatatatata tatagtacag tatattttaa catgtataaa    3891
caagatgcct attttatttt cagcttatta ctaatcacaa tatatatttg ctacatcaat    3951
agtataaaaa aaagctaaat atggttcttt tttctgctgt gacttattc ttttctttaa    4011 ttaaattata ggatatgata gct gca gcc aca gac act tct gct gtg acc aac   4064
              Ala Ala Ala Thr Asp Thr Ser Ala Val Thr Asn
                      330                 335 gaa tgg gca atg gct gag gta atc aga cat cca cat gtc ctc aaa aag     4112
Glu Trp Ala Met Ala Glu Val Ile Arg His Pro His Val Leu Lys Lys
340                 345                 350                 355 atc caa gaa gaa ctc gat ata gtt gtc ggg tcg ggt cgg atg gta acc     4160
Ile Gln Glu Glu Leu Asp Ile Val Val Gly Ser Gly Arg Met Val Thr
                360                 365                 370 gaa tcc gac ttg atc cat ctc aag tac ctc cgt tgt gta gta cgt gaa    4208
Glu Ser Asp Leu Ile His Leu Lys Tyr Leu Arg Cys Val Val Arg Glu
                    375                 380                 385 aca ttc cga atg cac cct gcg ggt cca ttc cta atc cca cat gaa tca    4256
Thr Phe Arg Met His Pro Ala Gly Pro Phe Leu Ile Pro His Glu Ser
            390                 395                 400 att cgc gat act atg atc aac ggc tat tac atc ccg gcc aag aca cgc    4304
Ile Arg Asp Thr Met Ile Asn Gly Tyr Tyr Ile Pro Ala Lys Thr Arg
405                 410                 415 gtg ttc atc aac aca cat ggt ctt ggc cgg aac aca aag att tgg gac    4352
Val Phe Ile Asn Thr His Gly Leu Gly Arg Asn Thr Lys Ile Trp Asp
420                 425                 430                 435 aac ata gat gag ttt agg cca gag aga cat tta cca cca aat gat gat    4400
Asn Ile Asp Glu Phe Arg Pro Glu Arg His Leu Pro Pro Asn Asp Asp
                440                 445                 450 gaa aaa aac atg atc atg act act agt agt agt aga gtt gag att agt    4448
Glu Lys Asn Met Ile Met Thr Thr Ser Ser Ser Arg Val Glu Ile Ser
                    455                 460                 465 cat ggt cca gat ttc aag att ttg cca ttt agt gct gga aaa agg aag    4496
His Gly Pro Asp Phe Lys Ile Leu Pro Phe Ser Ala Gly Lys Arg Lys
            470                 475                 480 tgt cct ggt gca cca ttg ggt gtg aaa ttg gtg ctt atg gca ttg gct    4544
Cys Pro Gly Ala Pro Leu Gly Val Lys Leu Val Leu Met Ala Leu Ala
485                 490                 495 agg ttg ttt cat tgc tat gat tgg agt cca cca aat gga gta aag cat    4592
Arg Leu Phe His Cys Tyr Asp Trp Ser Pro Pro Asn Gly Val Lys His
500                 505                 510                 515 caa gat att gac aca aat gaa gtt tat gga atg act atg cct aaa gct    4640
Gln Asp Ile Asp Thr Asn Glu Val Tyr Gly Met Thr Met Pro Lys Ala
                520                 525                 530 aag cca ttg atg gct att gct aaa cct aga ctg cct gct cac ttg tac    4688
Lys Pro Leu Met Ala Ile Ala Lys Pro Arg Leu Pro Ala His Leu Tyr
                    535                 540                 545 caa taa ttagttacta gtactcaaat caaagggaat tggtctttaa tggctttcgt     4744
Gln aacgaatcaa ataagagaaa atttctattt gtacctcgta aaaaaaagct ctcgcctcct   4804
gtaatagtat acttcaacat ttttctcacc tgtggcaatc cacacagcag acttaagtct   4864
gtctgattac atagta                                                  4880

<210> SEQ ID NO 13
<211> LENGTH: 1656
<212> TYPE: DNA
<213> ORGANISM: Artificial Sequence
<220> FEATURE:
<223> OTHER INFORMATION: cDNA CYPgst gene (Solanum tuberosum)
```

<400> SEQUENCE: 13

```
atgattgact tgactagttt tgttattgtc cttctttgca cgtatcttct taatttgatc      60
aattatagta tagtcctttt tggcgcatat cttatttcca agctacttca tttttcattc     120
gtcgataagt cgaatcgaga aatcaatcaa ctccctcctg gtccaaaaca atggcctat      180
gtaggcaacc tttttcagtt agggcaatta cctcatcgag acatggcgtc tttctgcgaa     240
aaatatggcc cattggtcta tctccgacta ggtaatgttg atgctatcac caccaatgat     300
ccagaaatca taagagaaat acttgtacaa caagatgatg tttttgcatc taggccaaga     360
actcttgctg ccattcatct agcttatggt tgtggggatg tggcattggc tcctttaggt     420
ccaaaatgga aagaatgag aagaatatgt atggaacatt tattgacaac taaaagactt     480
gaatcatttg caaacatag gcagatgaa gcccaaagtc tagttaaaga tatttggacc     540
aaagcccaaa aggacaaat agtgaatttg agggaagttt tgggtggatt ttcaatgaat     600
aatgtgacta gaatgttgtt aggtaaacaa tattttgggg cagaatcagc aggtccacaa     660
gaagcaatgg aatttatgca tgtaacacat gagttatttt ggttacttgg agtgatatat     720
ttaggtgatt atttacccttt ttggaggtgg attgatcctt atggttgtga gaaaaaaatg     780
agggatgttg aaaaaaggat tgatgatttt catatgagaa taattgaaga acatagaaag     840
aagaaaggta taaaaaataa taataatatt gatgatgatg aaatggactt tgtggatgtt     900
ttattgtctc taccaggaga agatgaagga gatggtaatg aaaacaaaa tatggatgat     960
gtagagatta agctctaat tcaggatatg atagctgcag ccacagacac ttctgctgtg    1020
accaacgaat gggcaatggc tgaggtaatc agacatccac atgtcctcaa aaagatccaa    1080
gaagaactcg atatagttgt cgggtcgggt cggatggtaa ccgaatccga cttgatccat    1140
ctcaagtacc tccgttgtgt agtacgtgaa acattccgaa tgcaccctgc gggtccattc    1200
ctaatcccac atgaatcaat tcgcgatact atgatcaacg ctattacat cccggccaag    1260
acacgcgtgt tcatcaacac acatggtctt ggccggaaca caaagatttg gacaacata    1320
gatgagttta ggccagagag acatttacca ccaaatgatg atgaaaaaaa catgatcatg    1380
actactagta gtagtagagt tgagattagt catggtccag atttcaagat tttgccattt    1440
agtgctggaa aaaggaagtg tcctggtgca ccattgggtg tgaaattggt gcttatggca    1500
ttggctaggt tgtttcattg ctatgattgg agtccaccaa atggagtaaa gcatcaagat    1560
attgacacaa atgaagttta tggaatgact atgcctaaag ctaagccatt gatggctatt    1620
gctaaaccta gactgcctgc tcacttgtac caataa                             1656
```

<210> SEQ ID NO 14
<211> LENGTH: 551
<212> TYPE: PRT
<213> ORGANISM: Solanum tuberosum
<220> FEATURE:
<221> NAME/KEY: PEPTID
<222> LOCATION: (1)..(551)
<223> OTHER INFORMATION: protein CYPgst (Solanum tuberosum)

<400> SEQUENCE: 14

Met Ile Asp Leu Thr Ser Phe Val Ile Val Leu Leu Cys Thr Tyr Leu
1               5                   10                  15

Leu Asn Leu Ile Asn Tyr Ser Ile Val Leu Phe Gly Ala Tyr Leu Ile
            20                  25                  30

Ser Lys Leu Leu His Phe Ser Phe Val Asp Lys Ser Asn Arg Glu Ile
        35                  40                  45

-continued

```
Asn Gln Leu Pro Pro Gly Pro Lys Gln Trp Pro Ile Val Gly Asn Leu
 50                  55                  60

Phe Gln Leu Gly Gln Leu Pro His Arg Asp Met Ala Ser Phe Cys Glu
 65                  70                  75                  80

Lys Tyr Gly Pro Leu Val Tyr Leu Arg Leu Gly Asn Val Asp Ala Ile
                 85                  90                  95

Thr Thr Asn Asp Pro Glu Ile Ile Arg Glu Ile Leu Val Gln Gln Asp
            100                 105                 110

Asp Val Phe Ala Ser Arg Pro Arg Thr Leu Ala Ala Ile His Leu Ala
        115                 120                 125

Tyr Gly Cys Gly Asp Val Ala Leu Ala Pro Leu Gly Pro Lys Trp Lys
130                 135                 140

Arg Met Arg Arg Ile Cys Met Glu His Leu Leu Thr Thr Lys Arg Leu
145                 150                 155                 160

Glu Ser Phe Ala Lys His Arg Ala Asp Glu Ala Gln Ser Leu Val Lys
                165                 170                 175

Asp Ile Trp Thr Lys Ala Gln Lys Gly Gln Ile Val Asn Leu Arg Glu
            180                 185                 190

Val Leu Gly Gly Phe Ser Met Asn Asn Val Thr Arg Met Leu Leu Gly
        195                 200                 205

Lys Gln Tyr Phe Gly Ala Glu Ser Ala Gly Pro Gln Glu Ala Met Glu
210                 215                 220

Phe Met His Val Thr His Glu Leu Phe Trp Leu Leu Gly Val Ile Tyr
225                 230                 235                 240

Leu Gly Asp Tyr Leu Pro Phe Trp Arg Trp Ile Asp Pro Tyr Gly Cys
                245                 250                 255

Glu Lys Lys Met Arg Asp Val Glu Lys Arg Ile Asp Asp Phe His Met
            260                 265                 270

Arg Ile Ile Glu Glu His Arg Lys Lys Gly Asn Lys Asn Asn Asn
        275                 280                 285

Asn Ile Asp Asp Asp Glu Met Asp Phe Val Asp Val Leu Leu Ser Leu
290                 295                 300

Pro Gly Glu Asp Glu Gly Asp Gly Asn Gly Lys Gln Asn Met Asp Asp
305                 310                 315                 320

Val Glu Ile Lys Ala Leu Ile Gln Asp Met Ile Ala Ala Ala Thr Asp
                325                 330                 335

Thr Ser Ala Val Thr Asn Glu Trp Ala Met Ala Glu Val Ile Arg His
            340                 345                 350

Pro His Val Leu Lys Lys Ile Gln Glu Glu Leu Asp Ile Val Val Gly
        355                 360                 365

Ser Gly Arg Met Val Thr Glu Ser Asp Leu Ile His Leu Lys Tyr Leu
370                 375                 380

Arg Cys Val Val Arg Glu Thr Phe Arg Met His Pro Ala Gly Pro Phe
385                 390                 395                 400

Leu Ile Pro His Glu Ser Ile Arg Asp Thr Met Ile Asn Gly Tyr Tyr
                405                 410                 415

Ile Pro Ala Lys Thr Arg Val Phe Ile Asn Thr His Gly Leu Gly Arg
            420                 425                 430

Asn Thr Lys Ile Trp Asp Asn Ile Asp Glu Phe Arg Pro Glu Arg His
        435                 440                 445

Leu Pro Pro Asn Asp Asp Glu Lys Asn Met Ile Met Thr Thr Ser Ser
450                 455                 460
```

```
Ser Arg Val Glu Ile Ser His Gly Pro Asp Phe Lys Ile Leu Pro Phe
465                 470                 475                 480

Ser Ala Gly Lys Arg Lys Cys Pro Gly Ala Pro Leu Gly Val Lys Leu
                485                 490                 495

Val Leu Met Ala Leu Ala Arg Leu Phe His Cys Tyr Asp Trp Ser Pro
            500                 505                 510

Pro Asn Gly Val Lys His Gln Asp Ile Asp Thr Asn Glu Val Tyr Gly
            515                 520                 525

Met Thr Met Pro Lys Ala Lys Pro Leu Met Ala Ile Ala Lys Pro Arg
530                 535                 540

Leu Pro Ala His Leu Tyr Gln
545                 550
```

<210> SEQ ID NO 15
<211> LENGTH: 525
<212> TYPE: PRT
<213> ORGANISM: Triticum aestivum
<220> FEATURE:
<221> NAME/KEY: PEPTID
<222> LOCATION: (1)..(525)
<223> OTHER INFORMATION: protein CYPgst (Trticum aestivum)

<400> SEQUENCE: 15

```
Met Asp Pro Phe Leu Leu Ser Ile Ile Leu Cys Ser Cys Ile Phe Ala
1               5                   10                  15

Ala Val Ser Trp Lys Lys Leu Asn Gly Met Arg Leu Arg Leu Pro Pro
                20                  25                  30

Gly Pro Pro Arg Trp Pro Ile Phe Gly Asn Leu Leu Gln Leu Ser Pro
                35                  40                  45

Leu Pro His Lys Asp Phe Ala Arg Phe Cys Thr Lys Tyr Gly Pro Leu
50                  55                  60

Val Tyr Leu Arg Leu Gly Thr Ile Asp Ala Ile Thr Thr Asp Asp Pro
65                  70                  75                  80

Glu Val Ile Arg Glu Ile Leu Ile Arg Gln Asp Glu Val Phe Ala Ser
                85                  90                  95

Arg Pro Arg Thr Leu Ala Ala Val His Leu Ala Tyr Gly Cys Gly Asp
                100                 105                 110

Val Ala Leu Ala Pro Leu Gly Pro Asn Trp Lys Arg Met Arg Arg Val
            115                 120                 125

Cys Met Glu His Leu Leu Thr Thr Arg Arg Leu Glu Ser Phe Ala Ala
130                 135                 140

His Arg Ala Glu Glu Ala Glu His Leu Cys Glu Phe Val Trp Ala Lys
145                 150                 155                 160

Ser Gln Ser Gly Lys Pro Val Asn Leu Arg Glu Val Leu Gly Ala Phe
                165                 170                 175

Ser Met Asn Asn Val Thr Arg Met Leu Leu Gly Lys Gln Tyr Phe Gly
                180                 185                 190

Leu Gln Ser Ala Gly Pro Gly Glu Ala Met Glu Phe Met His Ile Thr
            195                 200                 205

His Glu Leu Phe Phe Leu Leu Gly Leu Ile Tyr Leu Gly Asp Tyr Leu
210                 215                 220

Pro Ala Trp Arg Trp Leu Asp Pro Tyr Gly Cys Glu Lys Lys Met Arg
225                 230                 235                 240

Glu Val Glu Lys Lys Val Asp Asp Phe His Gln Lys Ile Ile Asp Glu
                245                 250                 255

His Arg Lys Ala Arg Asp Val Arg Lys Ser Gly Ala Ser Leu Asp Asp
```

```
                260                 265                 270
Asp Gly Asp Ser Lys Glu Gly Met Asp Phe Val Asp Leu Leu
            275                 280                 285

Ser Leu Pro Gly Glu Asn Gly Asn Glu His Met Asp Val Glu Ile
        290                 295                 300

Lys Ala Leu Met Gln Asp Met Ile Ala Ala Thr Asp Thr Ser Ser
305                 310                 315                 320

Val Thr Asn Glu Trp Val Met Ala Glu Val Ile Lys Asn Pro Arg Val
                325                 330                 335

Leu Arg Lys Ile Gln Glu Glu Leu Asp Ala Val Val Gly Thr Ser Arg
                340                 345                 350

Pro His Gly Gly Gly Gly Pro Pro Pro Asp Val Pro Pro Leu
        355                 360                 365

Arg Arg Pro Gly Val Leu Pro Asp Ala Pro Gly Gly Ala Ile Pro Asp
        370                 375                 380

Pro Ala Arg Val Thr Gln Gly Asp Asp His His Gly Leu Arg His Pro
385                 390                 395                 400

Gly Ala Asp Glu Asp Leu His Gln His Pro Arg Ala Gly Pro Glu Pro
                405                 410                 415

Ala His Leu Gly Arg Arg Arg Val Pro Pro Arg Glu Ala Pro Pro
                420                 425                 430

Gly Gly Arg Arg Ala Arg Gly Asp Gln Pro Pro Ala Gly Leu Gln Asp
        435                 440                 445

Pro Ala Leu Gln Arg Arg Gln Ala Gln Val Pro Arg Gly Ala Ala Gly
        450                 455                 460

Arg Asp Pro Gly Ala His Gly Ala Arg Gln Ala Leu Pro Leu Leu Arg
465                 470                 475                 480

Leu Val Pro Ala Arg Arg Pro Pro Arg Gly His Arg His Arg Arg
                485                 490                 495

Gly Leu Arg Asp Asp His Ala Gln Gly Gln Ala Ala His Arg Arg Arg
            500                 505                 510

Ser Thr Ala Pro Ala Ala Ala Asp Val Arg Leu Leu Ser
        515                 520                 525

<210> SEQ ID NO 16
<211> LENGTH: 518
<212> TYPE: PRT
<213> ORGANISM: Helianthus annuus
<220> FEATURE:
<221> NAME/KEY: PEPTID
<222> LOCATION: (1)..(518)
<223> OTHER INFORMATION: protein CYPgst (Helianthus annuus)

<400> SEQUENCE: 16

Met Asp Leu Gln Ser Phe Ile Ser Val Leu Ala Phe Ile Val Ala Ser
1               5                   10                  15

Arg Ile Ile Leu Leu Trp Tyr Val Lys Gln Arg Val Thr Gln Asn Thr
            20                  25                  30

Thr His Arg Leu Pro Pro Gly Pro Pro Arg Trp Pro Ile Val Gly Asn
        35                  40                  45

Leu Leu Gln Leu Gly Pro Leu Pro His Arg Asp Leu Ala Ser Phe Cys
    50                  55                  60

Glu Arg Tyr Gly Pro Leu Val Tyr Leu Arg Leu Gly Lys Val Asp Ala
65                  70                  75                  80

Ile Thr Thr Asn Asp Pro Asn Ile Ile Arg Glu Ile Leu Val Lys Gln
                85                  90                  95
```

Asp Asp Val Phe Ala Ser Arg Pro Gln Thr Leu Ala Ala Val His Leu
            100                 105                 110

Ala Tyr Asn Cys Gly Asp Val Ala Leu Ala Pro Phe Gly Pro Arg Trp
            115                 120                 125

Lys Trp Met Arg Arg Ile Cys Met Glu Gln Leu Leu Thr Thr Lys Arg
130                 135                 140

Leu Glu Ser Phe Ala Lys Gln Arg Ala Ser Glu Ala Gln His Leu Val
145                 150                 155                 160

Gln Asp Val Trp Ala Leu Ser Gln Ala Asn Gly Pro Ile Asn Leu Arg
            165                 170                 175

Glu Val Leu Gly Gly Phe Ser Met Asn Asn Val Thr Arg Met Leu Leu
            180                 185                 190

Gly Lys Gln Tyr Phe Gly Ser Gly Ser Ala Gly Pro Lys Glu Ala Thr
            195                 200                 205

Glu Phe Met His Ile Thr His Glu Leu Phe Trp Leu Leu Gly Leu Ile
            210                 215                 220

Tyr Leu Gly Asp Tyr Leu Pro Phe Trp Arg Trp Ile Asp Pro Tyr Gly
225                 230                 235                 240

Cys Glu Lys Lys Met Arg Glu Val Glu Lys Arg Val Asp Asp Phe His
            245                 250                 255

Met Lys Ile Ile Glu Glu His Arg Gln Arg Arg Lys Asn Gly Glu Gln
            260                 265                 270

Lys Asp Glu Gly Ile Met Asp Phe Val Asp Val Leu Leu Ser Leu Pro
            275                 280                 285

Gly Glu Asp Gly Lys Asp His Met Asp Asp Arg Gln Ile Lys Ala Leu
            290                 295                 300

Val Gln Asp Met Ile Ala Ala Thr Asp Thr Ser Ala Val Thr Asn
305                 310                 315                 320

Glu Trp Ala Met Ala Glu Val Ile Lys His Pro His Val Leu Arg Lys
            325                 330                 335

Ile Gln Glu Glu Leu Asp Asn Val Val Gly Pro Asp Arg Met Val Ser
            340                 345                 350

Glu Ser Asp Leu Ser Asn Leu Asn Tyr Leu Arg Cys Val Val Arg Glu
            355                 360                 365

Thr Phe Arg Met His Pro Ala Gly Pro Phe Leu Ile Pro His Glu Ser
            370                 375                 380

Leu Arg Ala Thr Glu Ile Asn Gly Tyr Tyr Ile Pro Ala Lys Thr Arg
385                 390                 395                 400

Val Phe Ile Asn Thr His Gly Leu Gly Arg Asn Thr Val Leu Trp Asp
            405                 410                 415

Asp Ile Asn Val Phe Arg Pro Glu Arg His Leu Thr Ser Asp Gly Ser
            420                 425                 430

Arg Val Glu Ile Ser His Gly Asp Asp Phe Lys Ile Leu Pro Phe Ser
            435                 440                 445

Ala Gly Lys Arg Lys Cys Pro Gly Ala Pro Leu Gly Val Thr Leu Val
            450                 455                 460

Leu Met Ala Leu Ala Arg Leu Phe His Cys Phe Asp Trp Ser Pro Pro
465                 470                 475                 480

Asp Gly Leu Lys Cys Glu Asp Ile Asp Thr Gln Glu Ile Tyr Gly Met
            485                 490                 495

Thr Met Pro Lys Ala Lys Pro Leu Met Ala Val Ala Lys Pro Arg Leu
            500                 505                 510

```
Ala Ser Tyr Met Tyr Gln
        515

<210> SEQ ID NO 17
<211> LENGTH: 530
<212> TYPE: PRT
<213> ORGANISM: Hordeum vulgare
<220> FEATURE:
<221> NAME/KEY: PEPTID
<222> LOCATION: (1)..(530)
<223> OTHER INFORMATION: protein CYPgst (Hordeum vulgare)

<400> SEQUENCE: 17

Met Asp Leu Phe Leu Phe Ser Ile Ile Leu Cys Ser Cys Ile Phe Ala
1               5                   10                  15

Ala Val Ser Trp Arg Lys Leu Ser Arg Leu Arg Leu Arg Leu Pro Pro
            20                  25                  30

Gly Pro Pro Arg Trp Pro Ile Phe Gly Asn Leu Leu Gln Leu Ser Pro
        35                  40                  45

Leu Pro His Lys Asp Phe Ala Arg Phe Cys Thr Lys Tyr Gly Pro Leu
    50                  55                  60

Val Tyr Leu Arg Leu Gly Thr Ile Asp Ala Ile Thr Thr Asp Asp Pro
65                  70                  75                  80

Glu Val Ile Arg Glu Ile Leu Val Arg Gln Asp Glu Val Phe Ala Ser
                85                  90                  95

Arg Pro Arg Thr Leu Ala Ala Val His Leu Ala Tyr Gly Cys Gly Asp
            100                 105                 110

Val Ala Leu Ala Pro Leu Gly Pro Asn Trp Lys Arg Met Arg Arg Val
        115                 120                 125

Cys Met Glu His Leu Leu Thr Thr Lys Arg Leu Glu Ser Phe Ala Ala
130                 135                 140

His Arg Ala Gln Glu Ala Glu His Leu Cys Glu Phe Val Trp Ala Lys
145                 150                 155                 160

Ser Gln Ser Gly Lys Pro Val Asn Leu Arg Glu Val Leu Gly Ala Phe
                165                 170                 175

Ser Met Asn Asn Val Thr Arg Met Leu Leu Gly Lys Gln Tyr Phe Gly
            180                 185                 190

Leu Gln Ser Ala Gly Pro Gly Glu Ala Met Glu Phe Met His Ile Thr
        195                 200                 205

His Glu Leu Phe Phe Leu Leu Gly Leu Ile Tyr Leu Gly Asp Tyr Leu
    210                 215                 220

Pro Ala Trp Arg Trp Val Asp Pro Tyr Gly Cys Glu Lys Lys Met Arg
225                 230                 235                 240

Glu Val Glu Lys Lys Val Asp Asp Phe His Gln Lys Ile Ile Asp Glu
                245                 250                 255

His Arg Lys Ala Arg Asp Ala Arg Lys Ser Ala Ala Ser Leu Asp Asp
            260                 265                 270

Gly Asp Ser Lys Glu Asp Met Asp Phe Val Asp Val Leu Leu Ser
        275                 280                 285

Leu Pro Gly Glu Asn Gly Asn Glu His Met Asp Asp Val Glu Ile Lys
    290                 295                 300

Ala Leu Met Gln Asp Met Ile Ala Ala Ala Thr Asp Thr Ser Ser Val
305                 310                 315                 320

Thr Asn Glu Trp Val Met Ala Glu Val Ile Lys Asn Pro Cys Val Leu
                325                 330                 335

Arg Lys Ile Gln Glu Glu Leu Asp Ala Val Val Gly Arg Ser Arg Met
```

```
                340                 345                 350
Val Val Glu Ser Asp Leu Pro His Leu Thr Tyr Leu Arg Cys Val Val
            355                 360                 365

Arg Glu Ser Phe Arg Met His Pro Ala Gly Pro Phe Leu Ile Pro His
        370                 375                 380

Glu Ser Leu Lys Ala Thr Thr Ile Met Gly Tyr Asp Ile Pro Ala Gln
385                 390                 395                 400

Thr Arg Ile Phe Ile Asn Thr His Ala Leu Gly Arg Asn Pro Arg Ile
                405                 410                 415

Trp Asp Asp Val Gly Glu Phe His Pro Glu Arg His Leu Pro Ala Asp
            420                 425                 430

Gly Gly Arg Val Glu Ile Ser His Leu Pro Asp Phe Lys Ile Leu Pro
        435                 440                 445

Phe Ser Ala Gly Lys Arg Lys Cys Pro Gly Ala Pro Leu Gly Val Ile
    450                 455                 460

Leu Val Leu Met Ala Leu Ala Arg Leu Phe His Cys Phe Asp Trp Ser
465                 470                 475                 480

Pro Pro Asp Gly Leu Arg Pro Glu Asp Ile Asp Thr Asp Glu Val Tyr
                485                 490                 495

Gly Met Thr Met Pro Lys Ala Lys Pro Leu Ile Ala Ala Val Gln Pro
            500                 505                 510

Arg Leu Pro Pro Gln Met Tyr Gly Ser Cys Pro Ser His Gly Met Gln
        515                 520                 525

Met Gln
    530

<210> SEQ ID NO 18
<211> LENGTH: 466
<212> TYPE: PRT
<213> ORGANISM: Brassica napus
<220> FEATURE:
<221> NAME/KEY: PEPTID
<222> LOCATION: (1)..(466)
<223> OTHER INFORMATION: protein CYPgst (Brassica napus)

<400> SEQUENCE: 18

Met Ala Ala Leu Cys Ser Lys Tyr Gly Pro Leu Val Tyr Leu Arg Leu
1               5                   10                  15

Gly Asn Ile Asp Ala Ile Thr Thr Asn Asp Pro Glu Thr Ile Arg Glu
            20                  25                  30

Ile Leu Phe Arg Gln Asp Asp Val Phe Ala Ser Arg Pro Lys Thr Leu
        35                  40                  45

Ala Ala Val His Leu Ala Tyr Gly Cys Gly Asp Val Ala Leu Ala Pro
    50                  55                  60

Met Gly Pro His Trp Lys Arg Met Arg Arg Ile Cys Met Glu His Leu
65                  70                  75                  80

Leu Thr Thr Lys Arg Leu Glu Ser Phe Thr Ser Gln Arg Ala Glu Glu
                85                  90                  95

Ala Gln Tyr Leu Ile Gln Asp Val Cys Lys Arg Ala Glu Cys Gly Lys
            100                 105                 110

Pro Ile Asn Leu Arg Glu Val Leu Gly Ala Phe Ser Met Asn Asn Val
        115                 120                 125

Thr Arg Met Leu Leu Gly Lys Gln Phe Phe Gly Pro Gly Ser Val Val
    130                 135                 140

Gly Ala Lys Glu Ala Gln Glu Phe Met His Ile Thr His Lys Leu Phe
145                 150                 155                 160
```

```
Arg Leu Leu Gly Val Ile Tyr Leu Gly Asp Tyr Leu Pro Phe Trp Arg
                165                 170                 175
Trp Val Asp Pro Tyr Gly Cys Glu Lys Glu Met Arg Asp Val Glu Lys
            180                 185                 190
Arg Val Asp Lys Phe His Thr Lys Ile Ile Glu Glu His Arg Arg Ala
        195                 200                 205
Lys Arg Glu Lys Glu Asp Lys Asn Ile Glu Gly Asp Met Asp Phe Val
    210                 215                 220
Asp Val Leu Leu Ser Leu Pro Gly Glu Asn Gly Lys Glu His Met Asp
225                 230                 235                 240
Asp Val Glu Ile Lys Ala Leu Ile Gln Asp Met Ile Ala Ala Ala Thr
                245                 250                 255
Asp Thr Ser Ala Val Thr Asn Glu Trp Ala Met Ala Glu Val Ile Lys
            260                 265                 270
Gln Pro Arg Val Met Arg Lys Ile Gln Glu Glu Leu Asp Asn Val Val
        275                 280                 285
Gly Ser Asn Arg Met Val Asn Glu Thr Asp Leu Val His Leu Asn Tyr
    290                 295                 300
Leu Arg Cys Val Val Arg Glu Thr Phe Arg Met His Pro Ala Gly Pro
305                 310                 315                 320
Phe Leu Ile Pro His Glu Ser Val Arg Pro Thr Thr Ile Asn Gly Tyr
                325                 330                 335
Tyr Ile Pro Ala Lys Thr Arg Val Phe Ile Asn Thr His Gly Leu Gly
            340                 345                 350
Arg Asn Thr Ser Val Trp Thr Thr Asp Ile Glu Glu Phe Arg Pro Glu
        355                 360                 365
Arg His Trp Pro Val Asp Gly Ser Gly Arg Val Glu Ile Ser His Gly
    370                 375                 380
Pro Asp Tyr Lys Ile Leu Pro Phe Ser Ala Gly Lys Arg Lys Cys Pro
385                 390                 395                 400
Gly Ala Pro Leu Gly Val Thr Met Val Leu Met Ala Leu Ala Arg Leu
                405                 410                 415
Phe His Cys Phe Asp Trp Thr Thr Pro Glu Asp Ile Asp Thr Val Glu
            420                 425                 430
Val Tyr Gly Met Thr Met Pro Lys Ala Lys Pro Leu Trp Ala Leu Ala
        435                 440                 445
Lys Pro Arg Leu Ala Ala His Leu Tyr Thr Ile Thr His Asp Thr Ile
    450                 455                 460
Gly His
465

<210> SEQ ID NO 19
<211> LENGTH: 530
<212> TYPE: PRT
<213> ORGANISM: Brassica oleracea
<220> FEATURE:
<221> NAME/KEY: PEPTID
<222> LOCATION: (1)..(530)
<223> OTHER INFORMATION: protein CYPgst (Brassica oleracea)

<400> SEQUENCE: 19

Met Asp Leu Phe Leu Leu Ser Ile Ile Leu Cys Ser Trp Ile Phe Val
1               5                   10                  15
Ala Val Tyr Trp Lys Lys Leu Asn Arg Thr Lys Leu Arg Leu Pro Pro
            20                  25                  30
```

-continued

Gly Pro Pro Arg Trp Pro Ile Phe Gly Asn Leu Leu Gln Leu Ser Pro
         35                  40                  45

Leu Pro His Lys Asp Phe Ala Arg Phe Cys Thr Lys Tyr Gly Pro Leu
 50                  55                  60

Val Tyr Leu Arg Leu Gly Thr Ile Asp Ala Ile Thr Thr Asp Asp Pro
 65                  70                  75                  80

Glu Val Ile Arg Glu Ile Leu Ile Arg Gln Asp Glu Val Phe Ala Ser
                 85                  90                  95

Arg Pro Arg Thr Leu Ala Ala Val His Leu Ala Tyr Gly Cys Gly Asp
                100                 105                 110

Val Ala Leu Ala Pro Leu Gly Pro Asn Trp Lys Arg Met Arg Arg Val
         115                 120                 125

Cys Met Glu His Leu Leu Thr Thr Lys Arg Leu Glu Ser Phe Ala Ala
         130                 135                 140

His Arg Ala Gln Glu Ala Glu His Leu Cys Gln Phe Val Trp Ala Lys
145                 150                 155                 160

Ser Gln Ser Glu Lys Pro Val Asn Leu Arg Glu Val Leu Gly Ala Phe
                165                 170                 175

Ser Met Asn Asn Val Thr Arg Met Leu Leu Gly Lys Gln Tyr Phe Gly
                180                 185                 190

Leu Gln Ser Ala Gly Pro Gly Glu Ala Met Glu Phe Met His Ile Thr
        195                 200                 205

His Glu Leu Phe Tyr Leu Leu Gly Leu Ile Tyr Leu Gly Asp Tyr Leu
        210                 215                 220

Pro Ala Trp Arg Trp Val Asp Pro Tyr Gly Cys Glu Lys Lys Met Arg
225                 230                 235                 240

Glu Val Glu Lys Lys Val Asp Asp Phe His Gln Lys Ile Ile Asp Glu
                245                 250                 255

His Arg Lys Ala Arg Glu Ala Arg Lys Ser Ala Ser Ser Leu Asp Asp
                260                 265                 270

Gly Asp Asp Ser Lys Glu Glu Met Asp Phe Val Asp Val Leu Leu Ser
        275                 280                 285

Leu Pro Gly Glu Asn Gly Lys Glu His Met Asp Asp Val Glu Ile Lys
        290                 295                 300

Ala Leu Met Gln Asp Met Ile Ala Ala Thr Asp Thr Ser Ser Val
305                 310                 315                 320

Thr Asn Glu Trp Val Met Ala Glu Val Ile Lys His Pro Arg Val Leu
                325                 330                 335

Arg Lys Ile Gln Glu Glu Leu Asp Ala Val Val Gly Arg Ala Arg Met
                340                 345                 350

Val Ser Glu Ser Asp Leu Pro His Leu Pro Tyr Leu Arg Cys Val Val
        355                 360                 365

Arg Glu Ser Phe Arg Met His Pro Ala Gly Pro Phe Leu Ile Pro His
        370                 375                 380

Glu Ser Leu Lys Pro Thr Thr Ile Met Gly Tyr Asp Ile Pro Ala Arg
385                 390                 395                 400

Thr Arg Ile Phe Ile Asn Thr His Ala Leu Gly Arg Asn Pro Arg Val
                405                 410                 415

Trp Asp Asp Val Gly Gln Phe Arg Pro Glu Arg His Met Pro Ala Asp
                420                 425                 430

Gly Gly Ala Arg Val Glu Ile Ser His Leu Pro Asp Phe Lys Ile Leu
        435                 440                 445

Pro Phe Ser Ala Gly Lys Arg Lys Cys Pro Gly Ala Pro Leu Gly Val

```
                 450                 455                 460
Ile Leu Val Leu Met Ala Leu Ala Arg Leu Phe His Cys Phe Asp Trp
465                 470                 475                 480

Ser Pro Pro Asp Gly Glu Ile Asp Thr Asp Glu Val Tyr Gly Met
                485                 490                 495

Thr Met Pro Lys Ala Leu Pro Leu Phe Ala Ala Arg Pro Arg Leu
                500                 505                 510

Pro Pro Glu Met Tyr His Gly Ser Ser Cys Pro Ser His Gly Lys Gln
                515                 520                 525

Thr Met
    530

<210> SEQ ID NO 20
<211> LENGTH: 466
<212> TYPE: PRT
<213> ORGANISM: Brassica rapa
<220> FEATURE:
<221> NAME/KEY: PEPTID
<222> LOCATION: (1)..(466)
<223> OTHER INFORMATION: protein CYPgst (Brassica rapa)

<400> SEQUENCE: 20

Met Ala Ala Leu Cys Ser Lys Tyr Gly Pro Leu Val Tyr Leu Arg Leu
1               5                   10                  15

Gly Asn Ile Asp Ala Ile Thr Thr Asn Asp Pro Glu Thr Ile Arg Glu
                20                  25                  30

Ile Leu Phe Arg Gln Asp Asp Val Phe Ala Ser Arg Pro Lys Thr Leu
            35                  40                  45

Ala Ala Val His Leu Ala Tyr Gly Cys Gly Asp Val Ala Leu Ala Pro
    50                  55                  60

Met Gly Pro His Trp Lys Arg Met Arg Arg Ile Cys Met Glu His Leu
65              70                  75                  80

Leu Thr Thr Lys Arg Leu Glu Ser Phe Thr Ser Gln Arg Ala Glu Glu
                85                  90                  95

Ala Gln Tyr Leu Ile Gln Asp Val Cys Lys Arg Ala Glu Cys Gly Lys
                100                 105                 110

Pro Ile Asn Leu Arg Glu Val Leu Gly Ala Phe Ser Met Asn Asn Val
            115                 120                 125

Thr Arg Met Leu Leu Gly Lys Gln Phe Phe Gly Pro Gly Ser Val Val
    130                 135                 140

Gly Ala Lys Glu Ala Gln Glu Phe Met His Ile Thr His Lys Leu Phe
145                 150                 155                 160

Arg Leu Leu Gly Val Ile Tyr Leu Gly Asp Tyr Leu Pro Phe Trp Arg
                165                 170                 175

Trp Val Asp Pro Tyr Gly Cys Glu Lys Glu Met Arg Asp Val Glu Lys
                180                 185                 190

Arg Val Asp Lys Phe His Thr Lys Ile Ile Glu Glu His Arg Arg Ala
            195                 200                 205

Lys Arg Glu Lys Glu Asp Lys Asn Ile Glu Gly Asp Met Asp Phe Val
    210                 215                 220

Asp Val Leu Leu Ser Leu Pro Gly Glu Asn Gly Lys Glu His Met Asp
225                 230                 235                 240

Asp Val Glu Ile Lys Ala Leu Ile Gln Asp Met Ile Ala Ala Ala Thr
                245                 250                 255

Asp Thr Ser Ala Val Thr Asn Glu Trp Ala Met Ala Glu Val Ile Lys
                260                 265                 270
```

```
Gln Pro Arg Val Met Arg Lys Ile Gln Glu Glu Leu Asp Asn Val Val
            275                 280                 285

Gly Ser Asn Arg Met Val Asn Glu Thr Asp Leu Val His Leu Asn Tyr
        290                 295                 300

Leu Arg Cys Val Val Arg Glu Thr Phe Arg Met His Pro Ala Gly Pro
305                 310                 315                 320

Phe Leu Ile Pro His Glu Ser Val Arg Pro Thr Thr Ile Asn Gly Tyr
                325                 330                 335

Tyr Ile Pro Ala Lys Thr Arg Val Phe Ile Asn Thr His Gly Leu Gly
                340                 345                 350

Arg Asn Thr Ser Val Trp Thr Thr Asp Ile Glu Glu Phe Arg Pro Glu
            355                 360                 365

Arg His Trp Pro Val Asp Gly Ser Gly Arg Val Glu Ile Ser His Gly
        370                 375                 380

Pro Asp Tyr Lys Ile Leu Pro Phe Ser Ala Gly Lys Arg Lys Cys Pro
385                 390                 395                 400

Gly Ala Pro Leu Gly Val Thr Met Val Leu Met Ala Leu Ala Arg Leu
                405                 410                 415

Phe His Cys Phe Asp Trp Thr Thr Pro Glu Asp Ile Asp Thr Val Glu
                420                 425                 430

Val Tyr Gly Met Thr Met Pro Lys Ala Lys Pro Leu Trp Ala Leu Ala
            435                 440                 445

Lys Pro Arg Leu Ala Ala His Leu Tyr Thr Ile Thr His Asp Thr Ile
    450                 455                 460

Gly His
465

<210> SEQ ID NO 21
<211> LENGTH: 523
<212> TYPE: PRT
<213> ORGANISM: Glycine max
<220> FEATURE:
<221> NAME/KEY: PEPTID
<222> LOCATION: (1)..(523)
<223> OTHER INFORMATION: protein CYPgst (Glycine max)

<400> SEQUENCE: 21

Met Asp Leu Thr Thr Phe Ile Ser Thr Leu Phe Leu Gly Thr Leu Ala
1               5                   10                  15

Ser Arg Ile Ile Arg His Trp Leu Ile Gly Arg Ser Leu Ser Ser His
            20                  25                  30

Lys Asn Lys Leu Pro Pro Gly Pro Pro Arg Trp Pro Ile Val Gly Asn
        35                  40                  45

Leu Leu Gln Leu Gly Gln Leu Pro His Arg Asp Leu Ala Ser Leu Cys
    50                  55                  60

Asp Lys Tyr Gly Pro Leu Val Tyr Leu Lys Leu Gly Lys Ile Asp Ala
65                  70                  75                  80

Ile Thr Thr Asn Asp Pro Asp Ile Ile Arg Glu Ile Leu Leu Ser Gln
                85                  90                  95

Asp Asp Val Phe Ala Ser Arg Pro His Thr Phe Ala Ala Val His Leu
                100                 105                 110

Ala Tyr Gly Cys Gly Asp Val Ala Leu Ala Pro Leu Gly Pro His Trp
            115                 120                 125

Lys Arg Met Arg Arg Ile Cys Met Glu His Leu Leu Thr Thr Lys Arg
        130                 135                 140
```

```
Leu Glu Ser Phe Ser Asn His Arg Leu Asp Glu Ala Gln His Leu Val
145                 150                 155                 160

Lys Asp Val Met Ala Trp Ala Gln Asp Lys Lys Pro Ile Asn Leu Arg
                165                 170                 175

Glu Val Leu Gly Ala Phe Ser Met Asn Asn Val Thr Arg Met Leu Leu
            180                 185                 190

Gly Lys Gln Tyr Phe Gly Ser Glu Ser Ser Gly Pro Gln Glu Ala Met
        195                 200                 205

Glu Phe Met His Ile Thr His Glu Leu Phe Trp Leu Leu Gly Val Ile
    210                 215                 220

Tyr Leu Gly Asp Tyr Leu Pro Ile Trp Arg Trp Val Asp Pro Tyr Gly
225                 230                 235                 240

Cys Glu Lys Lys Met Arg Glu Val Glu Lys Arg Val Asp Asp Phe His
                245                 250                 255

Ser Asn Ile Ile Glu Glu His Arg Lys Ala Arg Lys Asp Arg Lys Gly
                260                 265                 270

Lys Arg Lys Glu Gly Asp Gly Asp Met Asp Phe Val Asp Val Leu Leu
            275                 280                 285

Ser Leu Pro Gly Glu Asp Gly Lys Glu His Met Asp Asp Val Glu Ile
        290                 295                 300

Lys Ala Leu Ile Gln Asp Met Ile Ala Ala Thr Asp Thr Ser Ala
305                 310                 315                 320

Val Thr Asn Glu Trp Ala Met Ala Glu Val Met Lys His Pro His Val
                325                 330                 335

Leu His Lys Ile Gln Glu Glu Leu Asp Thr Ile Val Gly Pro Asn Arg
                340                 345                 350

Met Val Leu Glu Ser Asp Leu Pro His Leu Asn Tyr Leu Arg Cys Val
            355                 360                 365

Val Arg Glu Thr Phe Arg Met His Pro Ala Gly Pro Phe Leu Ile Pro
    370                 375                 380

His Glu Ser Leu Arg Ala Thr Thr Ile Asn Gly Tyr His Ile Pro Ala
385                 390                 395                 400

Lys Thr Arg Val Phe Ile Asn Thr His Gly Leu Gly Arg Asn Thr Lys
                405                 410                 415

Ile Trp Asp Asn Val Asp Glu Phe Arg Pro Glu Arg His Trp Pro Ser
            420                 425                 430

Asn Gly Asn Gly Thr Arg Val Glu Ile Ser His Gly Val Asp Phe Lys
        435                 440                 445

Ile Leu Pro Phe Ser Ala Gly Lys Arg Lys Cys Pro Gly Ala Pro Leu
    450                 455                 460

Gly Val Thr Leu Val Leu Met Ala Leu Ala Arg Leu Phe His Cys Phe
465                 470                 475                 480

Asp Trp Glu Pro Pro Lys Gly Leu Ser Cys Gly Asp Val Asp Thr Arg
                485                 490                 495

Glu Val Tyr Gly Met Thr Met Pro Lys Ala Glu Pro Leu Ile Ala Ile
            500                 505                 510

Ala Lys Pro Arg Leu Ala Lys His Leu Tyr Asp
        515                 520
```

<210> SEQ ID NO 22
<211> LENGTH: 537
<212> TYPE: PRT
<213> ORGANISM: Gossypium raimondii
<220> FEATURE:
<221> NAME/KEY: PEPTID
<222> LOCATION: (1)..(537)
<223> OTHER INFORMATION: protein CYPgst (Gossypium raimondii)

<400> SEQUENCE: 22

```
Met Ile Pro Tyr Lys Pro Ile Phe Phe Pro Leu Asp Asn Met Glu Leu
1               5                   10                  15

Phe Thr Phe Ala Leu Ala Leu Leu Val Gly Ala Leu Val Val Asn Ala
            20                  25                  30

Leu Trp Arg Trp Arg Leu Asp Trp Lys Ser Leu Phe Lys Thr Arg Lys
        35                  40                  45

Leu Pro Pro Gly Pro Pro Arg Trp Pro Ile Val Gly Asn Leu Leu Gln
    50                  55                  60

Leu Ser Ser Leu Pro His Arg Asp Leu Ala Ser Leu Cys Asp Lys Tyr
65                  70                  75                  80

Gly Pro Leu Val Tyr Leu Arg Leu Gly Lys Val Asp Ala Ile Thr Thr
                85                  90                  95

Asn Asp Pro Asp Ile Ile Arg Glu Ile Leu Leu Arg Gln Asp Glu Val
            100                 105                 110

Phe Ala Ser Arg Pro Arg Thr Leu Ala Ala Val His Leu Ala Tyr Gly
        115                 120                 125

Cys Gly Asp Val Ala Leu Ala Pro Leu Gly Pro His Trp Lys Arg Met
    130                 135                 140

Arg Arg Ile Cys Met Glu His Leu Leu Thr Thr Lys Arg Leu Glu Ser
145                 150                 155                 160

Phe Ala Lys His Arg Ala Asp Glu Ala Gln His Leu Val Arg Asp Val
                165                 170                 175

Ser Ala Arg Ala Glu Asn Gly Gln Leu Val Asn Leu Arg Glu Val Leu
            180                 185                 190

Gly Ala Phe Ser Met Asn Asn Val Thr Arg Met Leu Leu Gly Arg Gln
        195                 200                 205

Tyr Phe Gly Ala Val Ser Ala Gly Pro Ser Glu Ala Met Glu Phe Met
    210                 215                 220

His Ile Thr His Glu Leu Phe Trp Leu Leu Gly Val Ile Tyr Leu Gly
225                 230                 235                 240

Asp Tyr Leu Pro Ile Trp Arg Trp Val Asp Pro Tyr Gly Cys Glu Lys
                245                 250                 255

Arg Met Arg Glu Val Glu Lys Arg Val Asp Asp Phe His Glu Arg Ile
            260                 265                 270

Ile Glu Glu His Arg Arg Ala Arg Glu Leu Lys Asn Lys Gly Tyr Gly
        275                 280                 285

Lys Asp Asp Asp Tyr Gly Glu Glu Met Asp Phe Val Asp Val Leu Leu
    290                 295                 300

Ser Leu Pro Gly Glu Gly Asn Pro His Met Asp Asp Thr Asp Ile
305                 310                 315                 320

Lys Ala Leu Ile Gln Asp Met Ile Ala Ala Thr Asp Thr Ser Ala
                325                 330                 335

Val Thr Asn Glu Trp Thr Met Ala Glu Val Ile Lys His Pro Arg Val
            340                 345                 350

Leu Arg Lys Ile Gln Asp Glu Leu Asp Ser Val Gly Pro Asn Arg
        355                 360                 365

Met Val Asn Glu Ser Asp Leu Pro His Leu Asn Tyr Leu Arg Cys Val
    370                 375                 380

Val Arg Glu Thr Phe Arg Met His Pro Ala Gly Pro Phe Leu Ile Pro
385                 390                 395                 400
```

-continued

```
His Glu Ser Leu Arg Ala Thr Thr Ile Asn Gly Phe Tyr Ile Pro Ala
                405                 410                 415

Lys Thr Arg Val Phe Ile Asn Thr His Gly Leu Gly Arg Asn Thr Lys
            420                 425                 430

Leu Trp Asp Asp Val Glu Ser Phe Arg Pro Glu Arg His Trp Leu Ala
        435                 440                 445

Asp Gly Ala Arg Val Glu Ile Ser His Gly Ala Asp Phe Lys Ile Leu
    450                 455                 460

Pro Phe Ser Ala Gly Lys Arg Lys Cys Pro Gly Ala Pro Leu Gly Val
465                 470                 475                 480

Thr Leu Val Leu Met Ala Leu Ala Arg Leu Phe His Cys Phe Asp Trp
                485                 490                 495

Ala Pro Gln Asn Gly Met Arg Pro Glu Asp Ile Asn Thr Met Glu Val
            500                 505                 510

Tyr Gly Met Thr Met Pro Lys Ala Glu Pro Leu Met Ala Met Ala Lys
        515                 520                 525

Pro Arg Leu Ala Asp His Val Met Phe
    530                 535

<210> SEQ ID NO 23
<211> LENGTH: 526
<212> TYPE: PRT
<213> ORGANISM: Sorghum bicolor
<220> FEATURE:
<221> NAME/KEY: PEPTID
<222> LOCATION: (1)..(526)
<223> OTHER INFORMATION: protein CYPgst (Sorghum bicolor)

<400> SEQUENCE: 23

Met Asp Pro Phe Val Leu Ser Ile Leu Ile Cys Ser Trp Ile Phe Val
1               5                   10                  15

Val Val Tyr Trp Arg Arg Leu Asn Ser Met Arg Leu Arg Leu Pro Pro
            20                  25                  30

Gly Pro Pro Thr Trp Pro Ile Phe Gly Asn Leu Leu Gln Leu Ser Pro
        35                  40                  45

Leu Pro His Lys Asp Phe Ala Arg Phe Cys Thr Lys Tyr Gly Pro Leu
    50                  55                  60

Val Tyr Leu Arg Leu Gly Thr Ile Asp Ala Ile Thr Thr Asp Asp Pro
65                  70                  75                  80

Glu Val Ile Arg Glu Ile Leu Ile Arg Gln Asp Glu Val Phe Ala Ser
                85                  90                  95

Arg Pro Arg Thr Leu Ala Ala Val His Leu Ala Tyr Gly Cys Gly Asp
            100                 105                 110

Val Ala Leu Ala Pro Leu Gly Pro Asn Trp Lys Arg Met Arg Arg Val
        115                 120                 125

Cys Met Glu His Leu Leu Thr Thr Lys Arg Leu Glu Ser Phe Ala Ala
130                 135                 140

His Arg Ala Gln Glu Ala Glu His Leu Cys Gln Phe Val Trp Ala Lys
145                 150                 155                 160

Ser His Ser Gly Lys Pro Val Asn Leu Arg Glu Val Leu Gly Ala Phe
                165                 170                 175

Ser Met Asn Asn Val Thr Arg Met Leu Leu Gly Lys Gln Tyr Phe Gly
            180                 185                 190

Ile Gln Ser Ala Gly Pro Gly Glu Ala Met Glu Phe Met His Ile Thr
        195                 200                 205
```

His Glu Leu Phe Phe Leu Leu Gly Leu Ile Tyr Leu Gly Asp Tyr Leu
    210                 215                 220

Pro Ala Trp Arg Trp Val Asp Pro Tyr Gly Cys Glu Lys Lys Met Arg
225                 230                 235                 240

Asp Val Glu Lys Lys Val Asp Asp Phe His Gln Lys Ile Ile Asp Glu
                245                 250                 255

His Arg Arg Ala Arg Glu Ala Lys Lys Thr Arg Arg Ser Ser Leu Asp
            260                 265                 270

Asp Asp Asp Gly Lys Glu Asp Met Asp Phe Val Asp Val Leu Leu Ser
        275                 280                 285

Leu Pro Gly Glu Asn Gly Lys Glu His Met Asp Met Glu Ile Lys
290                 295                 300

Ala Leu Met Gln Asp Met Ile Ala Ala Ala Thr Asp Thr Ser Ser Val
305                 310                 315                 320

Thr Asn Glu Trp Val Met Ala Glu Val Ile Lys Asn Pro Arg Val Leu
                325                 330                 335

Arg Arg Val Gln Glu Glu Leu Asp Ala Val Ile Gly Arg Asp Arg Met
            340                 345                 350

Val Ala Glu Ser Asp Leu Thr His Leu Pro Tyr Leu Arg Cys Val Val
        355                 360                 365

Arg Glu Ser Phe Arg Met His Pro Ala Gly Pro Phe Leu Ile Pro His
370                 375                 380

Glu Ser Leu Lys Pro Thr Thr Ile Met Gly Tyr His Val Pro Ala Arg
385                 390                 395                 400

Thr Arg Val Phe Ile Asn Thr His Ala Leu Gly Arg Asn Pro Arg Val
                405                 410                 415

Trp Asp Asp Val Asp Ala Phe Arg Pro Glu Arg His Leu Pro Ala Glu
            420                 425                 430

Glu Gly Ala Arg Val Glu Ile Ser His Leu Pro Asp Phe Lys Ile Leu
        435                 440                 445

Pro Phe Ser Ala Gly Lys Arg Lys Cys Pro Gly Ala Pro Leu Gly Val
450                 455                 460

Ala Leu Val Leu Met Ala Leu Ala Arg Leu Phe His Cys Phe Asp Trp
465                 470                 475                 480

Ser Pro Pro Asp Gly Leu Arg Pro Glu Asp Val Asp Thr Gln Glu Val
                485                 490                 495

Tyr Gly Met Thr Met Pro Lys Ala Thr Pro Leu Val Ala Val Ala Thr
            500                 505                 510

Pro Arg Leu Pro Pro His Leu Tyr Gly Gly Ser Ala Ser
        515                 520                 525

<210> SEQ ID NO 24
<211> LENGTH: 41
<212> TYPE: DNA
<213> ORGANISM: Artificial Sequence
<220> FEATURE:
<223> OTHER INFORMATION: sxn2151s01-Markersequenz zum Anzeigen des
      gst-Locus in Beta vulgaris

<400> SEQUENCE: 24
aacactcatg taataagatg ggtgagtgag tagcaaaaaa a                          41

<210> SEQ ID NO 25
<211> LENGTH: 41
<212> TYPE: DNA
<213> ORGANISM: Artificial Sequence
<220> FEATURE:

<223> OTHER INFORMATION: sxn2151s01-Markersequenz zum Anzeigen des
      KWS2320- Referenzgenotyps

<400> SEQUENCE: 25
aacactcatg taataagatg agtgagtgag tagcaaaaaa a                          41

<210> SEQ ID NO 26
<211> LENGTH: 41
<212> TYPE: DNA
<213> ORGANISM: Artificial Sequence
<220> FEATURE:
<223> OTHER INFORMATION: sle3305s02-Markersequenz zum Anzeigen des
      gst-Locus in Beta vulgaris

<400> SEQUENCE: 26
aaagtctaga gtaaattgag gttgcagtgg agtgggaagt c                          41

<210> SEQ ID NO 27
<211> LENGTH: 41
<212> TYPE: DNA
<213> ORGANISM: Artificial Sequence
<220> FEATURE:
<223> OTHER INFORMATION: sle3305s02-Markersequenz zum Anzeigen des
      KWS2320- Referenzgenotyps

<400> SEQUENCE: 27
aaagtctaga gtaaattgag attgcagtgg agtgggaagt c                          41

<210> SEQ ID NO 28
<211> LENGTH: 4741
<212> TYPE: DNA
<213> ORGANISM: Beta vulgaris

<400> SEQUENCE: 28
gtatatcgtt gccacatgtg cgttgaattt ttccttttcc tatcctttcc actccatatt      60
ctcctcaaaa gtgtgtaaaa atccgacaca cgagtagaat gggattgaag tgggtcaaga     120
tctgaaacca atgggtcaat gccacaaaat aaggtaaggt ttctcgcagt agcaaaaaaa     180
taaagttaag ttgagagaaa aattatgaat agttgtttct cgtgaagagt tgtatacaaa     240
aaaagtctaa tttgatacat tttcttttac atttataaag gattgaccaa tcatccaaat     300
taccaaatat ttaggatata aatctttcag attacaaccc atatatgata cactaaattt     360
tacatgaggc aatggaggat ttgcatgaat atcgaggaga gaaaaaatta gttacaaaac     420
ttgcataatt tatccaaacc aaatcaagtc aagaaacaac gaacaatatt atcattagta     480
ctataagtat atattatagg cttagagcaa agccctaact accacactgc acacaaatga     540
taactagtaa gagaggaaaa tacaaattta agattcaaca tagcaaatta ttcatgattc     600
atgattcatg attcatgatt catgattcac gaacatcaag aatggtatag ctgataaagg     660
acaatttaaa cataagtgta aagctcgcac atcatcaatt atattcgcat actactagac     720
caatctttac ttagtacatg tgttagtaca tgtgttactt catatcagat gtattgattg     780
ttgccaatga catatcatgt tcacttaatc ttagggccat ttaattataa catggagaat     840
aatacaactt aaaattatgt ggtggctatc atctcatttt ctagataatt aaacctttat     900
tttgtataca tatatattgt ctttacatag caaaacaata ttgaaggtat aacaacctttt    960 cccttttctt ttactacatg tttatgttag agttttcga tttacgattg tggtaaatta    1020
attgtaattg atcggttgtc ttgtagtcaa gaaatgacgt atgaatcaat ttagggcatg    1080
ttctcttcgg cataaaacag ctgaactgaa ttgaactgaa ctgaaatgaa tagtgatatg    1140

```
tgagagtaaa agtattgtca agagctgaac tgagctgaac tgaacggatc tgaactgaac    1200
tgatctaatc tgaactaatc tgaactgaac tgaactgaat tgaactgaaa ataagctagg    1260
gaaaacagac ccttactact attatataac ctcgttaaa tattaggaaa ttaaaaaaat    1320
aattatattt ctttatactt tattaaccta ttgaggtttt tatattgact cccaaatact    1380
attttataga tcatgccatg ttaatgagca aactactttc tcacatcttt ataggagaaa    1440
aagtagatca ctcactagca tatcatgacc agcgaaacca accaacgcta atagttttat    1500
tgcttccatt agagataaga gttaactaat aataccatct ttgtgaaatt ttgatggatt    1560
ttggaacttt agcaatatat ttactgtgtg cactttttgc taccaaaatt ttataccaat    1620
ggctcaagtc ctacttatac acaacataca aactccctcc cggcccacca aggtggccct    1680
tatttggaaa cctccttcaa ctagggccac ttccccaccg cgatttcgcc tcattttgtg    1740
aaaaatatgg gcctttagtc tacataaggc ttggtaatgt ggatgccata accactaatg    1800
atccagaaat catacgtgag atcttagttc gacaagatga tgtatttgcg tctcgtccac    1860
ataccttagc cgcaacccac ttggcttaca atagtggtga tgtggccttg gctccaatgg    1920
gaccaaaatg gaaagaatg agaaggatat gcatggagca cttgctcaca actagacgac    1980
ttgaactatt tgtgagtcat agggctgatg aggcacgaca tttggtccaa gacgtattaa    2040
ctcgttccca caagataaa gttgttaatt tgagggaagt gttaggtgca ttttctatga    2100
ataacgtgac tagaatgttg ctagggaagc aatactttgg ggccgggacg gcgggcccac    2160
aagaggctct agagtttatg catataacac atgagttgtt ttggttacta ggcttgattt    2220
acttgggtga ttatttgcct ttttggaggt gggttgatcc atatgatgt gaaaagaaaa    2280
tgagggaagt tgaaaaaagg gtagatgatt ccatcgcaa aattatagag gaacatagga    2340
aggagaagaa aaggaaagaa gaaatgggag tgaatgaggg tgaaatggat tttgtagata    2400
ttttgttggc tttgcctggt gaaaatggaa atgagcatat ggatgatgca gatattaaag    2460
ctctaattca ggtaattcat gtataatttg aatgtgatcg atacaaagtt tgatagaaaa    2520
catatttgca taaatatatg gttgccctac tagacccaat aaaatacata attattgcct    2580
tactagttga aagttgaaac aacctagcta ccattttgtt gtgattatca ttagccaacc    2640
aaaattattt cttgcatcca tatattaatg ttgagatcag agtcggcata tttacaatta    2700
cttgtaacat tttaagcaaa caaattaaaa tattttttgg caagtccatt ttattgaata    2760
atacctatat cttaaaatga attcttggtc atgtacactt gcctttcaag gtaccaatat    2820
ttgaccatat gtaattacta ttaacaaatt tgataaaatc taataatatg taaatataca    2880
ttcacgcaca tattagaaac aaagatcaca aatgataatg caaaataact tatttgaact    2940
aatgttgtga agttaaattt ggaacaaaag gtatatttgt attgccgaat tttaatttat    3000
aaattactta taacaacaac tcaatatgta aaactgttaa gatggagtgt ggatagaatg    3060
agatgagtat acttttacta gttaccactc gaaaatgcat ttcctccttt gtttatagtt    3120
gttctaactt ctattatcat aaataatttt ttggacttat ttcaatgtat atttacaacg    3180
ctaattgttt aatttttaa aaatacataa tgtaaacaag gatttcatgg tcaattatac    3240
acattataaa tattatctta aaaaacttat taatgctcaa ttagtatcca taatatagga    3300
tatgatagca gcagcaacag acacatcagc tgtaaccaac gaatgggcca tggcagaagt    3360
aataaaacac ccacgtgtcc tccacaagat ccaacaagag cttaacacaa tagtaggacc    3420
caatcgaatg gtaacagaat cagatcttcc ccaccttaac tacctacgtt gtgtcgtacg    3480
tgaaacgttc cgaatgcatc cagcaggacc ctttttaatc ccacatgaat cactacgcca    3540
```

```
tacaacaatc aacggctatg atatcccatc tgggacacgt gtcttcatca acacacatgg    3600
gttaggacgt aaccttaaag tgtgggacaa catagaggat ttttaccctg aaagacattg    3660
gccgttggat ggaagtagag ttgagattag ccatggatct gattttaaaa tattaccatt    3720
tagtgctggg aagagaagat gtcctggggc cccacttggg gtggtgtttg tgttgatggg    3780
attggctaca cttttcatg catttgattg gttaccacct gatggaatga aggcagaaga     3840
aattgatact aaggaagttt atgggatgac tatgcctaaa gctcaacctt taatggcttt    3900
ggctaaacct aggcttgctc atttatatct ttgatacatg ttcatattgt ggtgcactta    3960
taagcacaat agacaaatac aagtttgtat cgactctaac atgttgttta gtattagtat    4020
actgcaactc tacaagtatg taatttctat aaactataaa cacaagtcat aacgcatttt    4080
gttttgaaaa aaaagaggtt acattgtctt acaccataaa ttgtttcctt gctacatttt    4140
tcttggttta tttagaacta attttcaat tttcctattt acttataata caagataaga     4200
aaaccgacta acaatatttc acaacattat atcttgatag ttcgttgaaa ttaataattt    4260
tcaataattt caaaacgcaa aaagcttctt tgttcggata aattcacgtc attttcaata    4320
aaatcgcgaa atcttccctt gccatcaagg aacaaatttt tcacatcaaa actcttcttc    4380
caaaaagtat acttctccac tgattatgta aaagagtttg catgttctaa tctattagta    4440
tgtatttttc ggataagaag ttgtattaca agcttaaata aagatataaa cttaattgaa    4500
tatcgaccaa tccacaatat gtatcttcat atgtgtccat caacgcctaa ccttgagatg    4560
tagatcatct aaagcacatt aacatgtcgt actcctcatg ttcagggttg tttgaaaccc    4620
aacttctcca aaatacttcc tcagtaataa agacaaaaac tcacattctg aaaaacatca    4680
acattatggt tctatggtct agtggttatg acactggact ctgaatccag taacccgagt    4740
t                                                                    4741
```

NUCLEUS-ENCODED MALE STERILITY THROUGH MUTATION IN CYTOCHROME P450 OXIDASE

CROSS-REFERENCE TO RELATED APPLICATIONS

This application is a U.S. National Phase of International Patent Application No. PCT/EP2017/058815, filed Apr. 12, 2017, which claims priority to German Patent Application No. 102016106656.7, filed on Apr. 12, 2016, both of which applications are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jul. 10, 2019, is named Seqlist245761_000072_ST25.txt, and is 122,743 bytes in size.

FIELD OF THE INVENTION

The present invention relates to the field of simplifying labor-intensive breeding programs by means of molecular biology methods, marker technologies and genetic engineering. In particular, plants are provided that exhibit a homozygous nucleus-encoded male sterile phenotype through spontaneous mutation of a gene region in the nucleus genome, distinguished in that the mutation is obtained through a recessive trait expression, in contrast to CMS (cytoplasmic male sterility), such that there is no need to obtain both sterile and fertile genotypes in a breeding program. In this regard, the present invention provides plants, in particular sugar beets or potatoes, in which a mutation resulting in the aforementioned trait expression is detected by means of marker technologies in a cytochrome P450 oxidase (CYPgst) gene and the corresponding method for identifying this mutation. Furthermore, a CYPgst protein, a DNA molecule containing the mutated gene resulting in the aforementioned trait expression, a recombinant DNA molecule that provides the wild type gene, a promoter for specific expressions of this gene, or a heterologous gene in flowers and/or fruits of plants and/or a nucleotide sequence that encodes inhibitors of the CYPgst gene, and corresponding vectors and host cells, are provided.

Furthermore, the present invention relates to plants modified through genetic engineering that have a recessive, nucleus-encoded male sterile phenotype through inhibition of the expression of the CYPgst gene, the respective inhibitors, and methods for inhibiting the gene and methods for restoring fertility. The invention also relates to the use of the plants in hybrid breeding, resistance breeding and/or seed production. Furthermore, the invention comprises seeds or descendants, organs, plant parts, tissues or cells of the plants according to the invention, as well as the use thereof.

BACKGROUND OF THE INVENTION

Crossbreeding is carried out in sugar beets (*Beta vulgaris*, subspecies *vulgaris*) as well as in all other cultivated plants for a controlled generation of genetic variation. Anthers carrying pollen are manually removed from still closed flowers of the seed parent. Pollination then also takes place manually by applying the pollen from the pollen donor to the stigma of the seed parent. Alternatively, pollination can also be obtained after removing the anthers on the flowers of the seed parent by placing the pollen donor in the spatial proximity of the seed parent for flowering and pollen delivery. In any case, this involves extremely labor-intensive protocols, which are very prone to error, because if only part of the anthers in a flower are removed, self pollination may occur, for example.

The production of (commercial) hybrid seeds currently takes place frequently through crossbreeding seed parent components in genotypes exhibiting CMS (cytoplasmic male sterility) and subsequent backcrossing in order to increase the genetic portion of seed parent components. The resulting male sterile seed parent components can subsequently be planted on a large scale, and pollination takes place though pollen donors growing close by (topcross method). Because the CMS dominant gene is inherited from the female, the use of CMS lines requires that fertile maintainer lines (thus not O-types embedded in CMS) must be kept available at the same time, which ensure pollination of the CMS lines. This requires a great deal of planning and production effort, as well a complex logistics. By way of example, commercial sugar beets are presently bred as triple hybrids, in order to produce seeds of a sufficiently high quality. The production of hybrids in breeding programs is likewise expensive and labor intensive, and is presently implemented by erecting dividing walls.

There are expressions of lines or genotypes in numerous types of plants that exhibit a naturally occurring nucleus-encoded male sterility (ms: male sterility). This is normally caused by spontaneous mutation of a gene in the nuclear genome, and this mutation is obtained through a recessive trait expression. The use of genotypes with nucleus-encoded male sterile phenotypes is appropriate for simplifying breeding processes and/or using these processes for generating hybrid seeds. The male sterile phenotypes thereby have the advantage that the anthers do not have to be removed manually for the crossbreeding, and fertile and sterile genotypes to not need to be obtained at the same time, because the heterozygous genotypes divide in turn in each reproductive cycle into fertile and sterile individuals through self-fertilization.

The object of the present invention is therefore to provide means and methods for using the nucleus-encoded male sterility in crop plants, in particular sugar beets and potatoes. This object is achieved in accordance with the invention through the embodiments characterized in the claims and the description.

SUMMARY OF THE INVENTION

The present invention relates to the field of simplifying labor-intensive breeding programs, marker technology and genetic engineering. The invention results in plants that exhibit a nucleus-encoded, recessive, male sterile phenotype through mutation in a DNA segment comprising a cytochrome P450 oxidase (CYPgst). The CYPgst gene and the mutation are identified using marker technologies and molecular biology methods. Because the mutation remains intact through the recessive trait expression, and heterozygous genotypes are then divided into fertile and sterile genotypes through self-fertilization in each reproductive cycle, there is no need to obtain fertile maintainer lines at the same time. In addition, the findings can be used for generating transgenic plants with a nucleus-encoded, recessive, male sterile phenotype, and to restore fertility.

The present invention therefore relates to embodiments listed in the following under paragraphs [1] to [36], and which are illustrated in the examples.

[1] A plant, in particular a crop plant, exhibiting a recessive, nucleus-encoded male sterile phenotype, characterized in that the phenotype correlates to a mutation, comprised by the endogenous cytochrome P450 oxidase (CYPgst) gene, or to the absence, or lower content in comparison with a corresponding (male fertile) wild type plant, or activity of a functional CYPgst protein encoded by the wild type CYPgst gene, characterized in that the non-mutated CYPgst gene is a) the gene BvCYPgst from *Beta vulgaris*, which preferably comprises a nucleotide sequence in SEQ ID No. 1 or 2, or encodes the amino acid sequence in SEQ ID No. 3 or its homolog, analog or ortholog, b) the gene StCYPgst from *Solanum tuberosum*, preferably comprising the nucleotide sequence in SEQ ID No. 12 or 13, or encodes the amino acid sequence in SEQ ID No. 14, or its homolog, analog, or ortholog, or c) the gene ZmCYPgst from *Zea mays*, preferably comprising the nucleotide sequence in SEQ ID Nos. 9 or 10, or encoding the amino acid sequence in SEQ ID No. 11, or its homolog, analog, or ortholog.

[2] The plant according to paragraph [1], which is heterozygous for the mutation and male fertile, or homozygous for the mutation and male sterile, wherein the formation of functional pollen is suppressed, preferably entirely suppressed, in the sterile plants.

[3] The plant according to paragraph [1] or [2], wherein the CYPgst gene is expressed at least in closed flowers and fruits.

[4] The plant according to any of the paragraphs [1] to [3], wherein the mutation prevents transcription and/or translation of a functional protein, preferably wherein the mutation concerns a deletion, addition, insertion, or substitution in the encoding nucleotide sequence of the CYPgst gene, a splicing signal, or in a regulatory sequence, preferably the promoter sequence, of the CYPgst gene. In a preferred embodiment, the nucleic acid molecule has a mutation that can also be found in the nucleotide sequence in SEQ ID No. 8 in comparison with the wild type gene in SEQ ID No. 1. In particular, the mutation can be a deletion between nucleotide positions 1560 and 2095 of SEQ ID No. 1 or corresponding positions in SEQ ID Nos. 12 or 9. The deletion can comprise at least 20, 30 or 50 consecutive base pairs, preferably at least 100, 150, 200 or 250 consecutive base pairs, and particularly preferably at least 300, 400 or 500 consecutive base pairs. In a particularly preferred embodiment, the nucleic acid molecule comprises a nucleotide sequence according to SEQ ID No. 8. In another preferred embodiment, the nucleic acid molecule has a point mutation in the nucleotide sequence of SEQ ID No. 1 according to Table 1, preferably between nucleotide positions 1560 and 2095 of SEQ ID No. 1.

[5] The plant according to paragraph [4], wherein in *Beta vulgaris*, preferably *Beta vulgaris*, subspecies *vulgaris*, the deletion can be detected through the absence of one or both marker loci sle5983d14 (amplification product of the primer with SEQ ID Nos. 4 and 5) and sle5983d17 (amplification product of the primer with SEQ ID Nos. 6 and 7) and through the presence of a ubiquitous marker.

[6] The plant according any of the paragraphs [1] through [5], wherein the gene is located in *Beta vulgaris*, preferably *Beta vulgaris*, subspecies *vulgaris*, in a segment on chromosome 1 between marker loci sxn2151s01 and sle3305s02, wherein the sxn2151s01 marker sequence shown in SEQ ID No. 24 and the sle3305s02 marker sequence shown in SEQ ID No. 26 display the presence of the gst locus, and the sxn2151s01 marker sequence shown in SEQ ID No. 25 and the sle3305s02 marker sequence shown in SEQ ID No. 27 display the reference sequence.

[7] The plant according to paragraph [6], wherein the sequence is approx. 50 to 5,000 kbp, 100 to 1,000 kbp, more preferably 100 to 500 kbp, and particularly preferably 200 to 250 kbp.

[8] The plant according to any of the paragraphs [1] to [7], wherein the non-mutated gene is the functional gene BvCYPgst from *Beta vulgaris*, preferably *Beta vulgaris*, subspecies *vulgaris*, or a functional homologous, analogous, or orthologous gene of another cultivated or crop plant.

[9] The plant according to paragraph [8], wherein the homologous, analogous, or orthologous gene is a *Zea mays* gene, which preferably comprises a nucleotide sequence in SEQ ID Nos. 9 or 10, or encodes the amino acid sequence in SEQ ID No. 11, a *Solanum tuberosum* gene, which preferably comprises a nucleotide sequence displayed in SEQ ID No. 12 or 13, or encodes the amino acid sequence in SEQ ID No. 14, a *Triticum aestivum* gene, which preferably encodes the amino acid sequence in SEQ ID No. 15, a *Helianthus annuus* gene, which preferably encodes the amino acid sequence in SEQ ID No. 16, a *Hordeum vulgare* gene, which preferably encodes the amino acid sequence in SEQ ID No. 17, a *Brassica napus* gene, which preferably encodes the amino acid sequence in SEQ ID No. 18, a *Brassica oleracea* gene, which preferably encodes the amino acid sequence in SEQ ID No. 19, a *Brassica rapa* gene, which preferably encodes the amino acid sequence in SEQ ID No. 20, a *Glycine max* gene, which preferably encodes the amino acid sequence in SEQ ID No. 21, a *Gossypium* gene, which preferably encodes the amino acid sequence in SEQ ID No. 22, or a *Sorghum bicolor* gene, which preferably encodes the amino acid sequence in SEQ ID No. 23.

[10] The plant according to any of the paragraphs [1] to [9], wherein the non-mutated gene (wild type gene) has a nucleotide sequence selected from the group comprising:
(a) a nucleotide sequence with the nucleotide sequence in SEQ ID No. 1 or SEQ ID No. 2, or a functional fragment thereof (see, e.g., FIGS. 4A and 4B);
(b) a nucleotide sequence that encodes the amino acid sequence in SEQ ID No. 3;
(c) a nucleotide sequence capable of hybridization on a nucleotide sequence complementary to a nucleotide sequence according to (a) or (b) under stringent conditions;
(d) a nucleotide sequence that encodes an amino acid sequence, which has deviations from the amino acid sequence according to SEQ ID No. 3 in the form of amino acid deletions, substitutions, additions, and/or insertions in the amino acid sequence and is preferably identical to at least 60% of the entire amino acid sequence;
(e) a nucleotide sequence that encodes a protein with the same enzymatic activity as the protein encoded by the nucleotide sequence according to any of the nucleotide sequences (a) to (d); and
(f) a nucleotide sequence that comprises at least 200 or 400, preferably at least 600 or 800, particularly preferably at least 1,000 consecutive nucleotides from the promoter of the nucleic acid sequence from SEQ ID No. 1 of nucleotide positions 1 to 1518, preferably nucleotide positions 518 to 1518, particularly preferably nucleotide positions 1318-1518, or a sequence that is hybridized at this region, wherein the nucleotide sequence is capable of controlling the expression of the gene, or a heterologous nucleic acid molecule operatively linked to the nucleotide sequence, specifically in closed flowers or fruit.

A nucleotide sequence according to (c), (d) or (e) is a nucleotide sequence, for example, that displays the nucleotide sequence in SEQ ID No. 12 or SEQ ID No. 13, or a functional fragment thereof, or encodes the amino acid sequence in SEQ ID No. 14. Furthermore, a nucleotide sequence according to (c), (d) or (e) is a nucleotide sequence, for example, that displays the nucleotide sequence in SEQ ID No. 9 or SEQ ID No. 10, or a functional fragment thereof, or encodes the amino acid sequence in SEQ ID No. 11. Furthermore, a nucleotide sequence according to (c), (d) or (e) is a nucleotide sequence, for example, that encodes an amino acid sequence selected from the group composed of SEQ ID Nos. 15-23.

[11] A plant according to any of the paragraphs [1] to [10], wherein the plant is an inbred plant or a hybrid plant.

[12] A plant according any of the paragraphs [1] to [11], that is a plant from the genus Zea, Solanum, Triticum, Triticale, Helianthus, Secale, Hordeum, Brassica, Brachypodium, Glycine, Gossypium, Sorghum, Saccharum, Setaria, Aegilops, Oryza, Daucus, Eucalyptus, Erythranthe, Genlisea, Musa, Avena, Nicotiana, Coffea, Vitis, Cucumis, Morus, Crucihimalaya, Cardamine, Lepidium, Capsella, Olimarabidopsis, Arabis, Raphanus, Eruca, Citrus, Jatropha, Populus, or Beta, preferably a plant of the type Zea mays, Solanum tuberosum, Triticum aestivum, Triticum durum, Triticum spelta, Helianthus annuus, Secale cereal, Hordeum vulgare, Hordeum bulbosum, Brassica napus, Brassica oleracea, Brassica rapa, Brassica juncacea, Brassica nigra, Glycine max, Gossypium sp., Sorghum bicolor, Triticale, Saccharum officinarum, Setaria italica, Oryza sativa, Oryza minuta, Oryza australiensis, Oryza alta, Brachypodium distachyon, Hordeum marinum, Aegilops tauschii, Daucus glochidiatus, Daucus pusillus, Daucus muricatus, Daucus carota, Eucalyptus grandis, Erythranthe guttate, Genlisea aurea, Musa sp., Avena sp., Nicotiana sylvestris, Nicotiana tabacum, Nicotiana tomentosiformis, Solanum lycopersicum, Coffea canephora, Vitis vinifera, Cucumis sativus, Morus notabilis, Crucihimalaya himalaica, Crucihimalaya wallichii, Cardamine flexuosa, Lepidium virginicum, Capsella bursa-pastoris, Olimarabidopsis pumila, Arabis hirsute, Raphanus sativus, Eruca vesicaria sativa, Citrus× sinensis, Jatropha curcas, Populus trichocarpa or Beta vulgaris.

[13] A nucleic acid molecule or recombinant DNA molecule, comprising a nucleotide sequence as defined in paragraph [10].

[14] The recombinant DNA molecule according to paragraph [13], which (i) comprises a promoter with a nucleotide sequence as defined in paragraph [10] (f), which is operatively linked to a heterologous nucleic acid molecule, or (ii) comprises an encoding nucleotide sequence as defined in paragraph [10] (a)-(e), which is operatively linked to a heterologous promoter, preferably capable of controlling the expression of the nucleotide sequence specifically in closed flowers or fruit.

[15] A recombinant DNA molecule comprising a nucleotide sequence that encodes an shRNA (small hairpin RNA), siRNA (small interfering RNA), negative sense RNA, positive sense RNA or double strand RNA, which leads to inhibition of the expression of the functional (non-mutated) CYPgst gene after expression in a plant cell or after introduction into a plant cell. In a preferred embodiment, the nucleotide sequence has at least 15, 16, 17, 18, 19, or 20, preferably at least 21, 22, 23, 24, or 25, particularly preferably at least 30, 35, 40, 45, or 50, and very particularly preferably at least 100, 200, 300, 500, or 1,000, consecutive nucleotides of the SEQ ID No. 1, 2, 9, 10, 12, or 13 in positive or negative sense orientation, or from at least one exon 1 of SEQ ID No. 1 from nucleotide position 1762-2679 and the exon 2 of SEQ ID No. 1 from nucleotide position 3507-4142. Exon 1 of SEQ ID No. 12 extends from nucleotide position 1762-2032, exon 2 of SEQ ID No. 12 extends from nucleotide position 2449-2161, and exon 3 of SEQ ID No. 12 extends from nucleotide position 4032-4694. Exon 1 of SEQ ID No. 9 extends from nucleotide position 2001-2927, and exon 2 of SEQ ID No. 9 extends from nucleotide position 3018-3683. In another preferred embodiment, the nucleotide sequence has at least 15, 16, 17, 18, 19, or 20, preferably at least 21, 22, 23, 24, or 25, particularly preferably at least 30, 35, 40, 45, or 50, and very particularly preferably at least 100, 200, 300, 500, or 1,000 consecutive nucleotides, which are capable of specific hybridization on a nucleotide sequence as defined in paragraph [10].

[16] A nucleic acid molecule that comprises a nucleotide sequence as defined in paragraph [10], with a mutation in the form of a deletion, addition, insertion, or substitution, wherein this mutation results in no synthesis of functional CYPgst proteins. The mutation is preferably in the encoding nucleotide sequence of the CYPgst gene, located in a splicing signal, or in a regulatory sequence of the CYPgst gene, preferably in the promoter of the CYPgst gene. In a preferred embodiment, the nucleic acid molecule has a mutation that can also be found in the nucleotide sequence according to SEQ ID No. 8. In particular, the mutation can be a deletion between nucleotide positions 1560 and 2095 of SEQ ID No. 1 or corresponding positions in SEQ ID Nos. 12 or 9. The deletion can have a length of at least 20, 30 or 50 consecutive base pairs and particularly preferably at least 100, 150, 200, or 250 consecutive base pairs, and particularly preferably at least 300, 400, or 500 consecutive base pairs. In a particularly preferred embodiment, the nucleic acid molecule comprises a nucleotide sequence according to SEQ ID No. 8. In another preferred embodiment, the nucleic acid molecule has a point mutation in the nucleotide sequence of SEQ ID No. 1 according to Table 1, preferably between nucleotide positions 1560 and 2095 of SEQ ID No. 1.

[17] A nucleic acid molecule of at least 15, 16, 17, 18, 19, or 20, preferably at least 21, 22, 23, 24, or 25, particularly preferably at least 30, 35, 40, 45, or 50, and very particularly preferably at least 100, 200, 300, 500, or 1,000 consecutive nucleotides in SEQ ID Nos. 1, 2, 9, 10, 12, or 13 in positive and/or negative sense orientation, or at least one exon of SEQ ID Nos. 1, 9, or 12 in positive and/or negative sense orientation. Exon 1 in SEQ ID No. 1 extends from nucleotide position 1762-2679, and exon 2 in SEQ ID No. 1 extends from nucleotide position 3507-4142. Exon 1 in SEQ ID No. 12 extends from nucleotide position 1762-2032, exon 2 in SEQ ID No. 12 extends from nucleotide position 2449-3161, and exon 3 of SEQ ID No. 12 extends from nucleotide position 4032-4694. Exon 1 in SEQ ID No. 9 extends from nucleotide position 2001-2927, and exon 2 in SEQ ID No. 9 extends from nucleotide position 3018-3683. In a special embodiment, the nucleic acid molecule extends over at least one intron in SEQ ID No. 1, SEQ ID No. 9, or SEQ ID No. 12, i.e. the nucleic acid molecule successively comprises i) at least one nucleotide from the 3' end of exon 1 in SEQ ID No. 1 (preferably the last nucleotide of exon 1 of SEQ ID No. 1 in the 5'-3' direction; corresponding to the nucleotide at position 583 in SEQ ID No. 2) and at least one nucleotide from the 5' end of exon 2 in SEQ ID No. 1 (preferably the first nucleotide of exon 2 in SEQ ID No. 1 in the 5'-3' direction; corresponding to the nucleotide at position 584 in SEQ ID No. 2), ii) at least one nucleotide from the 3' end of exon 1 in SEQ ID No. 12 (preferably the last nucleotide of exon 1 in SEQ ID No. 12 in the 5'-3' direction; corresponding to the nucleotide at position 271 in SEQ ID No. 13), and at least one nucleotide from the 5' end of exon 2 in SEQ ID No. 12 (preferably the first nucleotide of exon 2 in SEQ ID No. 12 in the 5'-3' direction; corresponding to the nucleotide at position 272 in SEQ ID No. 13), iii) at least one nucleotide from the 3' end of exon 2 in SEQ ID No. 12 (preferably the last nucleotide of exon 2 in SEQ ID No. 12 in the 5'-3' direction; corresponding to a nucleotide at position 984 in SEQ ID No. 13) and at least one nucleotide of exon 3 in SEQ ID No. 12 in the 5'-3' direction; corresponding to the nucleotide at position 985 in SEQ ID No. 13), or iv) at least one nucleotide from the 3' end of exon 1 in SEQ ID No. 9 (preferably the last nucleotide of exon 1 in SEQ ID No. 9 in the 5'-3' direction; corresponding to the nucleotide at position 927 in SEQ ID No. 10), and at least one nucleotide from the 5' end of exon 2 in SEQ ID No. 9 (preferably the first nucleotide of exon 2 in SEQ ID No. 9 in the 5'-3' direction; corresponding to the nucleotide at position 928 in SEQ ID No. 10). In another preferred embodiment, the nucleotide sequence has at least 15, 16, 17, 18, 19, or 20, preferably at least 21, 22, 23, 24, or 25, particularly preferably at least 30, 35, 40, 45, or 50, and very particularly preferably at least 100, 200, 300, 500, or 1,000 consecutive nucleotides, which is capable of specific hybridization on a nucleotide sequence as defined in [10] or [16].

[18] An oligonucleotide, preferably with a length of no more than 50 nucleotides, comprising a nucleic acid molecule according to paragraph [17] or a nucleic acid molecule that is capable of specific hybridization on a nucleotide sequence according to SEQ ID No. 8, and/or preferably has one of the following nucleotide sequences:
(i) SEQ ID Nos. 4, 6, or a complement thereof, or
(ii) SEQ ID Nos. 5, 7, or a complement thereof.

[19] A vector, preferably a plant vector, comprising a DNA molecule, or a nucleic acid molecule according to any of the paragraphs [13] to [16], or a nucleic acid molecule according to paragraph [17].

[20] The vector according to paragraph [19], wherein the DNA molecule, or nucleic acid molecule in the form of a transgene, is capable of expressing a functional CYPgst and is preferably genetically coupled to another transgene, which prevents transfer of the DNA molecule or nucleic acid molecule via pollen, preferably wherein the vector, or the transgene also has an expression cassette that marks the seeds, preferably with a fluorescent marking.

[21] A host cell, preferably a plant cell containing a recombinant DNA molecule, or nucleic acid molecule according to any of the paragraphs [13] to [16], or a vector according to paragraph [19] or [20].

[22] A CYPgst protein encoded by a nucleotide sequence as defined in paragraph [10], or a functional and/or immunologically active fragment thereof. The CYPgst protein is preferably a) the amino acid sequence selected from the group composed of SEQ ID No. 3, SEQ ID No. 11, and SEQ ID Nos. 14-23, orb) an amino acid sequence that is identical to the amino acid sequence according to SEQ ID No. 3 for at least 80%, 82%, 84%, 86%, or 88%, preferably at least 90%, 91%, 92%, 93%, 94%, or 95%, particularly preferably for at least 96%, 97%, 98%, 99% or 99.5%, preferably over the entire length thereof.

[23] An antibody that binds specifically to the CYPgst protein or fragment according to paragraph [22].

[24] A kit comprising a DNA molecule or nucleic acid molecule according to any of the paragraphs [13] to [16], a nucleic acid according to paragraph [17], an oligonucleotide according to paragraph [18], a vector according to paragraph [19] or [20], a CYPgst protein or fragment thereof according to paragraph [22], and/or an antibody according to paragraph [23], and potentially reagents for nucleic acid based or immunological detection processes.

[25] A method for producing a plant, in particular a crop plant, that displays a recessive, nucleus-encoded, homozygous male sterile phenotype, characterized in that the expression of the CYPgst gene is inhibited.

[26] The method according to paragraph [25], characterized in that the method comprises a step for introducing the recombinant DNA molecule according to paragraph [15], the nucleic acid molecule according to paragraph [16] or [17], or the vector according to paragraph [19] or [20], e.g. by means of agrobacterium transformation, T-DNA tagging, homologous recombination, mutagenesis, such as TILLING, and targeted mutagenesis, e.g. through the use of zinc finger nucleases, TALE (Transcription Activator-Like Effector) nucleases, and the CRISPR/Cas system, resulting in inhibition of the gene expression, e.g. through RNAi or co-suppression or due to the mutation that has been introduced.

[27] A method for restoration of the fertility of a plant according to any of the paragraphs [1] to [12] or a plant that can be obtained through a method according to paragraph [25] or [26], comprising the introduction of a functional CYPgst gene into the plant.

[28] The method according to paragraph [27], wherein the CYPgst gene is introduced by means of a recombinant DNA according to paragraph [13] or [14], or a vector according to paragraph [19] or [20], or through crossbreeding a plant carrying the CYPgst wild type gene or a functional CYPgst gene, preferably in the homozygous state. Optionally, a selection for the presence of the CYPgst wild type gene or the functional CYPgst gene can take place in following generation.

[29] A plant containing plant cells according to paragraph [21] and/or that can be obtained through a method according to any of the paragraphs [25] to [28].

[30] An organ, plant part, tissue or cell of the plant according to any of the paragraphs [1] to [12] or [19].

[31] Seeds or descendants of the plant according to any of the paragraphs [1] to [12] or [29], wherein the seeds or the descendants that have a mutation defined in any of the paragraphs [1] to [12] and/or a recombinant DNA molecule or nucleic acid molecule according to any of the paragraphs [13] to [16] or a vector according to paragraph [19] or [20].

[32] A method for identifying a plant according to any of the paragraphs [1] to [12] or [29] by detecting a mutation in the CYPgst gene, or a marker coupled to the mutation.

[33] Use of a DNA molecule or nucleic acid molecule according to any of the paragraphs [13] to [16], a nucleic acid molecule according to paragraph [17], an oligonucleotide according to paragraph [18], a vector according to paragraph [19] or [20], a CYPgst protein or fragment thereof according to paragraph [22], an antibody according to paragraph [23], and/or kits according to paragraph [24] for producing a plant according to any of the paragraphs [1] to [12] or [29], in production of a recessive, nucleus-encoded, male sterile plant, in production of a plant with restored fertility, in production of a hybrid plant, in resistance programs, or for seed production.

[34] Use of the DNA molecule according to paragraph [14] or the promoter defined in paragraph [14] for specific expression of heterologous nucleic acid molecules in flowers and/or fruit from plants.

[35] Use of a plant according to any of the paragraphs [1] to [12] or [29], organ, plant part, tissue or cell according to paragraph [30], seeds or descendants according to paragraph [31], or a plant that can be identified according to the method according to paragraph [32], or obtained through a use according to paragraph [33] or [34], or the tissues, cells, descendants or seeds in the production of food, active substances, medicinal products, or precursors thereof, diagnostic products, cosmetics, fine chemicals, sugar, syrup, bioethanol or biogas.

[36] Food, feed or active substances contained in a plant according to any of the paragraphs [1] to [12] or [29], organ, plant part, tissue, or cell according to paragraph [30], seeds or descendants according to paragraph [31], or a plant that is identified by the method according to paragraph [32], or that can be obtained through the use according to paragraph [33] or [34], or the tissues, cells, descendants or seeds thereof.

[37] Use of a plant according to any of the paragraphs [1] to [12] or [29] for breeding or the production of a descendant plant, wherein the nucleus-encoded male sterile phenotype is used for recurrent selection.

First, some of the terms used in this application shall be explained in greater detail:

The expression "chromosome segment," and variations of the term, such as "chromosomal segment" or "segment of chromosome," are used equivalently, if not indicated otherwise, and refer to a specific chromosomal DNA segment of a specific chromosome, comprising at least one gene.

The "CYPgst gene" or the "wild type gene from CYPgst" encoded for the "CYPgst protein," which plays a role in the formation of vital pollen, in that a mutation in CYPgst results in male sterile plants by suppressing the formation of functional pollen. This has been demonstrated experimentally in the sugar beet (*Beta vulgaris*, subspecies *vulgaris*). A similarity to the CYP703 gene from *Arabidopsis thaliana* could be established through homology comparisons, which fulfills an essential function according to the current prior art (Morant et al., The Plant Cell, 19 (2007), 1473-1487) in the synthesis of sporopollenin, and preferably catalyzes the conversion of medium chain saturated fatty acids into the corresponding simple hydroxylated fatty acids, with a preferred hydroxylation of lauric acid at the C-7 position. The elimination of the CYP703 gene in *Arabidopsis thaliana* results in a partial male sterility. The quantity of pollen was actually reduced, but functional pollen could still be produced. For this reason, the gene from *Beta vulgaris*, subspecies *vulgaris* appears to assume another function, as an elimination thereof results in a male sterility of the plant. Without committing to a theory, it appears to be plausible that the CYPgst gene should be assigned to a different classification of the CYP gene, or in cultivated plants, in particular crop plants such as the sugar beet, has a different function or significance than in the lower model plant *Arabidopsis thaliana*; see the discussion in example 1. The person skilled in the art can derive other CYPgst proteins from data bases using appropriate search profiles and computer programs for screening for homologous sequences or sequence comparisons. A possible assessment of whether the identified gene fulfills the same function as the CYPgst gene in *Beta vulgaris*, subspecies *vulgaris*, can be assessed through restoring the function of CYPgst in a male sterile sugar beet plant through heterologous expression of the identified gene, i.e. through restoration of the fertility through the transgene.

Without committing to a specific theory, there is also the possibility that the CYPgst gene from *Beta vulgaris*, subspecies *vulgaris* and the CYP703 gene from *Arabidopsis thaliana* belong to the same CYP family, and thus fulfill the same or at least a similar function in the synthesis of sporopollenin, but that in cultivated plants, which have been optimized over years of targeted selection and crossbreeding with regard to yield, pest resistance, tolerance of abiotic stress factors, etc., as well as the content of plant substances, the ability to compensate for the lack of sporopollenin is lost, and that therefore the absence of sporopollenin results in suppression of pollen formation, leaving the plant male sterile.

The term "gst locus" refers, according to the invention, to a genomic DNA in a plant, in particular a crop plant, in which a mutation correlates to a recessive inherited, nucleus-encoded male sterility, wherein the mutation comprises cytochrome P450 oxidase (CYPgst) gene and results in the mutation being contained in the gst locus in a plant affected in this manner, and in particular with the mutation of homozygous plants, the content or the activity of a functional CYPgst protein is lower in comparison with a corresponding (male fertile) plant containing the wild type locus (wild type plant), or is entirely absent. Typically, transcription and/or translation of a functional CYPgst protein is prevented by the mutation in the CYPgst gene.

The term "closely flanking" is understood to mean that two loci (e.g. two marker (marker loci)) are separated from one another on a gene map by less than 15 cM, less than 12 cM, less than 10 cM, less than 8 cM, less than 7 cM, less than 6 cM, less than 5 cM, less than 4 cM, less than 3 cM, less than 2 cM, less than 1 cM, less than 0.5 cM, less than 0.2 cM, less than 0.1 cM, less than 0.05 cM.

The term "hybridizing" or "hybridization" refers to a process in which a single-strand nucleic acid molecule attaches to a complementary nucleic acid strand to the greatest possible extent, i.e. base pairs interact therewith. Standard methods for hybridization are described by way of example in Sambrook et al., Molecular Cloning; A Laboratory Manual 3$^{rd}$ ed., Cold Spring Harbor Laboratory Press, Cold Spring Harbor, N.Y., 2001. It is preferably understood thereby that at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule engage in a base pairing with the complementary nucleic acid strand to the greatest possible extent. The possibility of such an attachment depends on the stringency of hybridization conditions. The term "stringency" relates to the hybridization conditions. High stringency exists when a base pairing is hindered, and low stringency exists when a base pairing is facilitated. The stringency of the hybridization conditions depends on the salt concentration, or the ionic strength, for example, and temperature. In general, the stringency can be increased by increasing the temperature and/or lowering the salt content. "Stringent hybridization conditions" refer to those conditions in which hybridization predominantly takes place only between homologous nucleic acid molecules and homologous genes. The term "hybridization conditions" relates not only to the prevailing conditions during the actual attachment of the nucleic acids, but also to the conditions prevalent during the subsequent growth steps. Stringent hybridization conditions are conditions, for example, under which predominantly only those nucleic acid molecules hybridize that are identical to at least 70%, preferably at least 75%, at least 80%, at least 85%, at least 90% or at least 95%. Stringent hybridization conditions are, e.g.: hybridization in 4×SSC at 65° C., and subsequent multiple washings in 0.1×SSC at 65° C. for at total of approx. 1 hour. The term "stringent hybridization conditions" used here can also mean: hybridization at 68° C. in 0.25 M sodium phosphate, pH 7.2, 7% SDS, 1 mM EDTA and 1% BSA for 16 hours and subsequent washing twice with 2×SSC and 0.1% SDS at 68° C. Hybridization preferably takes place under stringent conditions.

"Complementary" nucleotide sequence, in reference to a nucleic acid in the form of a double strand DNA, means that the first DNA strand is complementary to the second DNA strand with respect to the base pair regulation of the nucleotides that correspond to the bases of the first strand.

The term "(molecular) marker" is a nucleotide sequence used as a reference or orientation point. A marker for detecting a recombination should be suitable for monitoring differences or polymorphisms within a plant population. With markers, these differences occur at the DNA level, and comprise polynucleotide sequence differences, e.g. SSRs (simple sequence repeats), RFLPs (restriction fragment length polymorphisms), FLPs (fragment length polymorphisms) or SNPs (single nucleotide polymorphisms). The markers can be derived from genomic or expressed nucleic acids, e.g. spliced RNA, cDNA or ESTs, and can also relate to nucleic acids that are used as probe or primer pairs, and as such are suitable for amplifying a sequence fragment using PCR-based methods. Markers relating to genetic polymorphisms between portions of a population can be detected by means of established methods from the prior art (An Introduction to Genetic Analysis, $7^{th}$ edition, Griffiths, Miller, Suzuki, et al., 2000). These include, e.g.: DNA sequencing, PCR-based, sequence specific amplification, detection of RFLPs, detection of polynucleotide polymorphisms by means of allele-specific hybridization (ASH), and detections of SSRs, SNPs or RFLPs. Moreover, methods for detecting ESTs (expressed sequence tags) and RAPD (randomly amplified polymorphic DNA) are also known. Depending on the context, the term "marker" can also mean a specific chromosome position in the genome of a species where a specific marker (e.g. SNP) can be located. Markers are also used in this invention for detecting deletions.

The term "crop plant" encompasses both uncultivated plants as well as cultivated plants. Plants are referred to as crop plants that are used in any form by humans, directly or indirectly; e.g. as food, stimulants, or medication, as well as wood supplies or as feed for livestock.

A "cultivated plant," in contrast to wild plants, is a plant that is planted, cultivated and protected by humans, which can be used as a crop plant or decorative plant. The genetic basis for the existence of cultivated plants comprises point mutations, somatic mutations, chromosomal mutations and polyploidization. These mutations provide the basis for selection. They form the natural or artificially extended (increase in mutation rate, crossbreeding, treatment with colchicine, genetic engineering methods) starting material for human-controlled evolution. Cultivated plants include food plants, industrial plants (e.g. fiber plants) feed plants and decorative plants. The important features of these cultivated plants are an increase in the size of the plants, in particular the organs that are used, loss of bitter substances, pest resistance, and/or higher nutrient content.

"Operatively linked" means interconnected in a shared nucleic acid molecule, such that the interconnected elements are positioned and oriented in relation to one another in a manner allowing for transcription of the nucleic acid molecule to take place. A DNA that is operatively linked to a promoter is subject to the transcriptional control of this promoter.

A "plant" as set forth in the invention can be any of the dicotyledon or monocotyledon plant species. Plants in agriculture, horticulture or for generating bioenergy (bioethanol, biogas, etc.) are preferred. The plants used in the present invention are preferably distinguished by their storage organs comprising tubers, roots, seeds, grain, fruit, etc. These include, by way of example, *Zea mays, Solanum tuberosum, Triticum aestivum, Triticum durum, Triticum spelta, Helianthus annuus, Secale cereal, Hordeum vulgare, Hordeum bulbosum, Brassica napus, Brassica oleracea, Brassica rapa, Brassica juncacea, Brassica nigra, Glycine max, Gossypium sp., Sorghum bicolor, Triticale, Saccharum officinarum, Setaria italica, Oryza sativa, Oryza minuta, Oryza australiensis, Oryza alta, Brachypodium distachyon, Hordeum marinum, Aegilops tauschii, Daucus glochidiatus, Daucus pusillus, Daucus muricatus, Daucus carota, Eucalyptus grandis, Erythranthe guttate, Genlisea aurea, Musa sp., Avena sp., Nicotiana sylvestris, Nicotiana tabacum, Nicotiana tomentosiformis, Solanum lycopersicum, Coffea canephora, Vitis vinifera, Cucumis sativus, Morus notabilis, Crucihimalaya himalaica, Crucihimalaya wallichii, Cardamine flexuosa, Lepidium virginicum, Capsella bursa-pastoris, Olimarabidopsis Arabis hirsute, Raphanus sativus, Eruca vesicaria sativa, Citrus sinensis, Jatropha curcas, Populus trichocarpa* or *Beta vulgaris*. A plant according to the invention is preferably a plant of the genus *Beta*, in particular the species sugar beet (*Beta vulgaris*), as well as the subspecies, *Beta vulgaris*, subspecies *vulgaris*.

Plant "organs" refer, by way of example, to leaves, plant stems, trunks, roots, vegetative buds, meristems, sprouts, anthers, ovum, seeds or fruit, in particular grains. The term "plant part" or "plant parts" includes but is not limited to, the plant stem, or stalk, leaves, flowers, fluorescence, roots, fruit and seeds, as well as pollen. Plant "parts" also refers to a combination of numerous organs, e.g. a flower or a seed, or a part of an organ, e.g. a cross section of the plant stem. Plant "tissues" are, for example, callus tissues, storage tissues, meristematic tissues, leaf tissues, sprout tissues, root tissues, plant center tissues, or reproductive tissues, as well as the meristem tissues, the base tissues (the so-called parenchyma), vascular tissues, consolidation tissues and covering tissues (the so-called epidermis). The tissues are not limited to those listed here. Plant "cells" are understood to be isolated cells with a cell wall, for example, or aggregates thereof, or protoplasts.

In the context of the present invention, the term "regulatory sequence" refers to a nucleotide sequence that affects the specificity and/or the expression strength, e.g. in that the regulatory sequence imparts a specific tissue specificity. Such a regulatory sequence can be located upstream of the transcription initiation point of a minimal promoter, but also downstream thereof, as is the case for example, in a transcribed but not translated leader sequence or inside an intron.

A "promoter" is a non-translated DNA segment, typically upstream of an encoded region that contains the binding site for the RNA polymerase, and initiates the DNA transcription. A promoter also contains other elements that function as regulators for the gene expression (e.g. cis-regulatory elements). A "nuclear or minimal promoter" is a promoter that contains at least the base elements needed for initiating the transcription (e.g. TATA box and/or initiator).

A "transgenic plant" is a plant in which genomes of at least one polynucleotide are integrated, preferably a heterologous polynucleotide. The polynucleotide is preferably integrated in a stable manner, i.e. the integrated polynucleotide remains stable in the plant, is expressed, and can also be inherited by the descendants in a stable manner. The stable introduction of a polynucleotide in the genome of a plant also includes the integration thereof in the genome of a plant from the preceding generation, wherein the polynucleotide can be stably passed on to later generations. The term "heterologous" means that the introduced polynucleotide comes, by way of example, from a cell or an organism with a different genetic background in the same species or some other species, or is homologous to the prokaryotic or eukaryotic host cell, but is then located in a different genetic environment, and thus differs from a potentially naturally occurring corresponding polynucleotide. A heterologous polynucleotide can also exist in addition to a corresponding endogenic gene.

Designs and embodiments of the present invention shall be described below by way of example with reference to the attached drawings and sequences:

FIG. 1: A, C) flowers from fertile sugar beets (*Beta vulgaris*, subspecies *vulgaris*) and B, D) flowers from male sterile sugar beets, the phenotypes of which can be traced back to Donor C311 [2043_K5]. A, B) are closed flowers, the sepals and petals of which have been removed manually. The light (yellow), vital anthers of the fertile genotype (A) can be clearly seen. In contrast, the anthers of the sterile genotypes are clearly dark (brown). The anthers of fertile genotypes open during the flowering stage and release pollen (C), while the anthers of the sterile genotypes do not continue to develop and contain no pollen.

Figure 2:
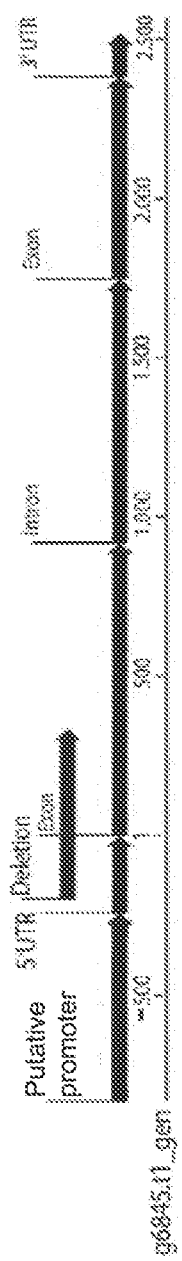

FIG. 2: The gene model annotated in RefBeet 1.2, type BvCYPgst (g6845.t1) in the reference genotype KWS2320. The protein, with a length of 517 amino acids is encoded by exons with a total length of 1554 bp. Genotypes expressed in a male sterile phenotype display a deletion of 533 bp, the portion comprising the 5' UTR and the first exon of the gene. A correct transcription of the mRNA and translation of a functional protein is thus impossible.

Figure 3:
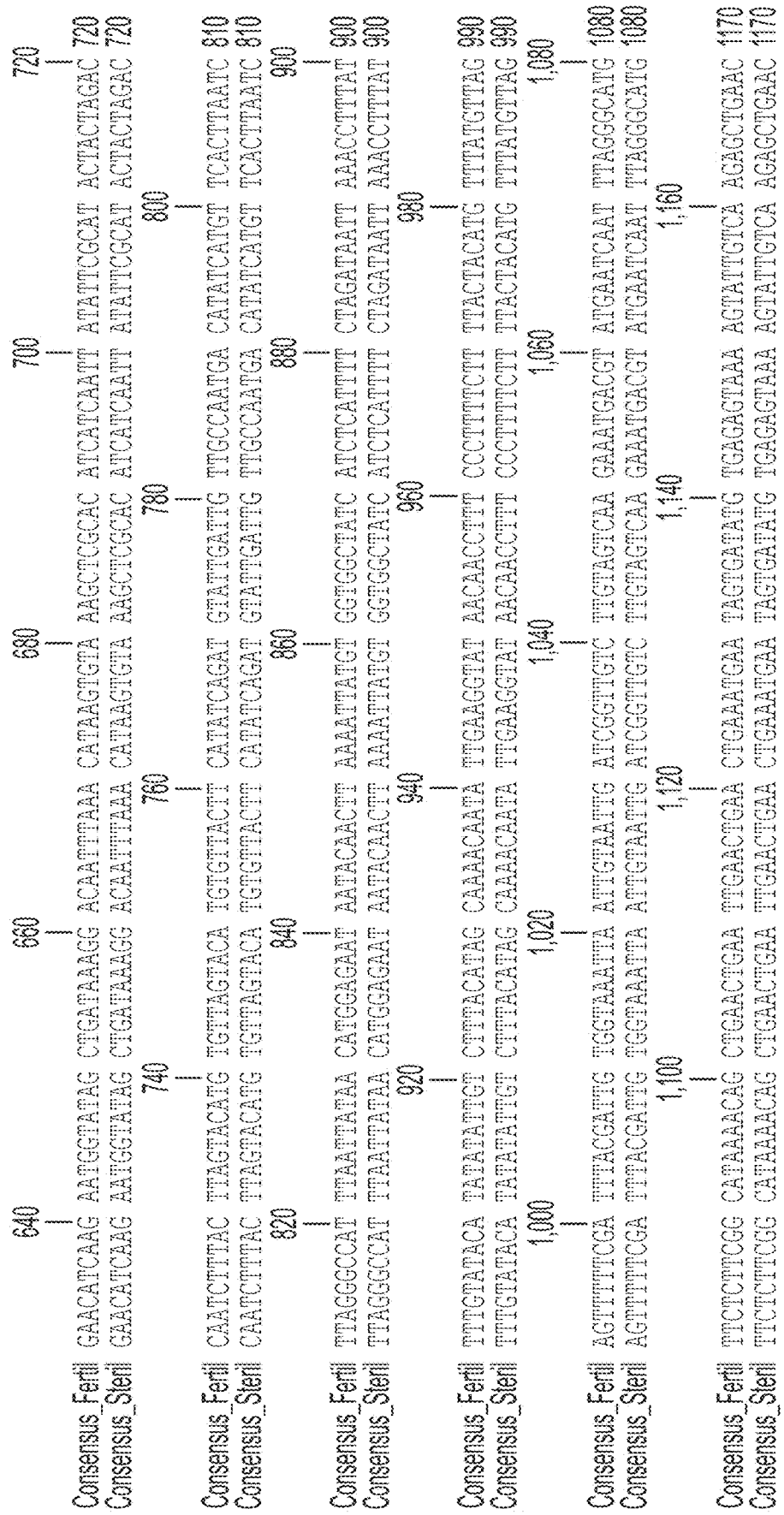
Figure 3:
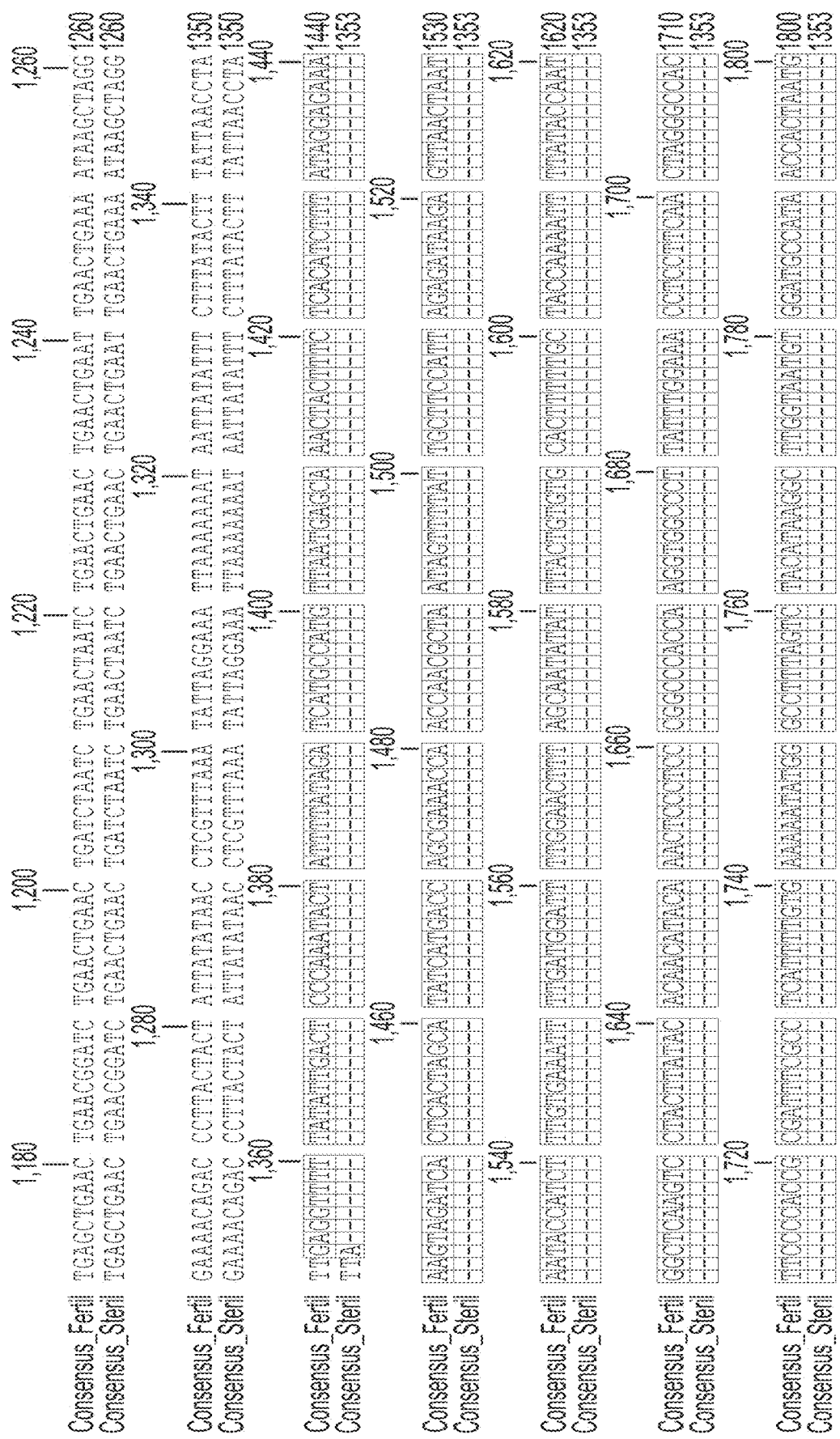
Figure 3:
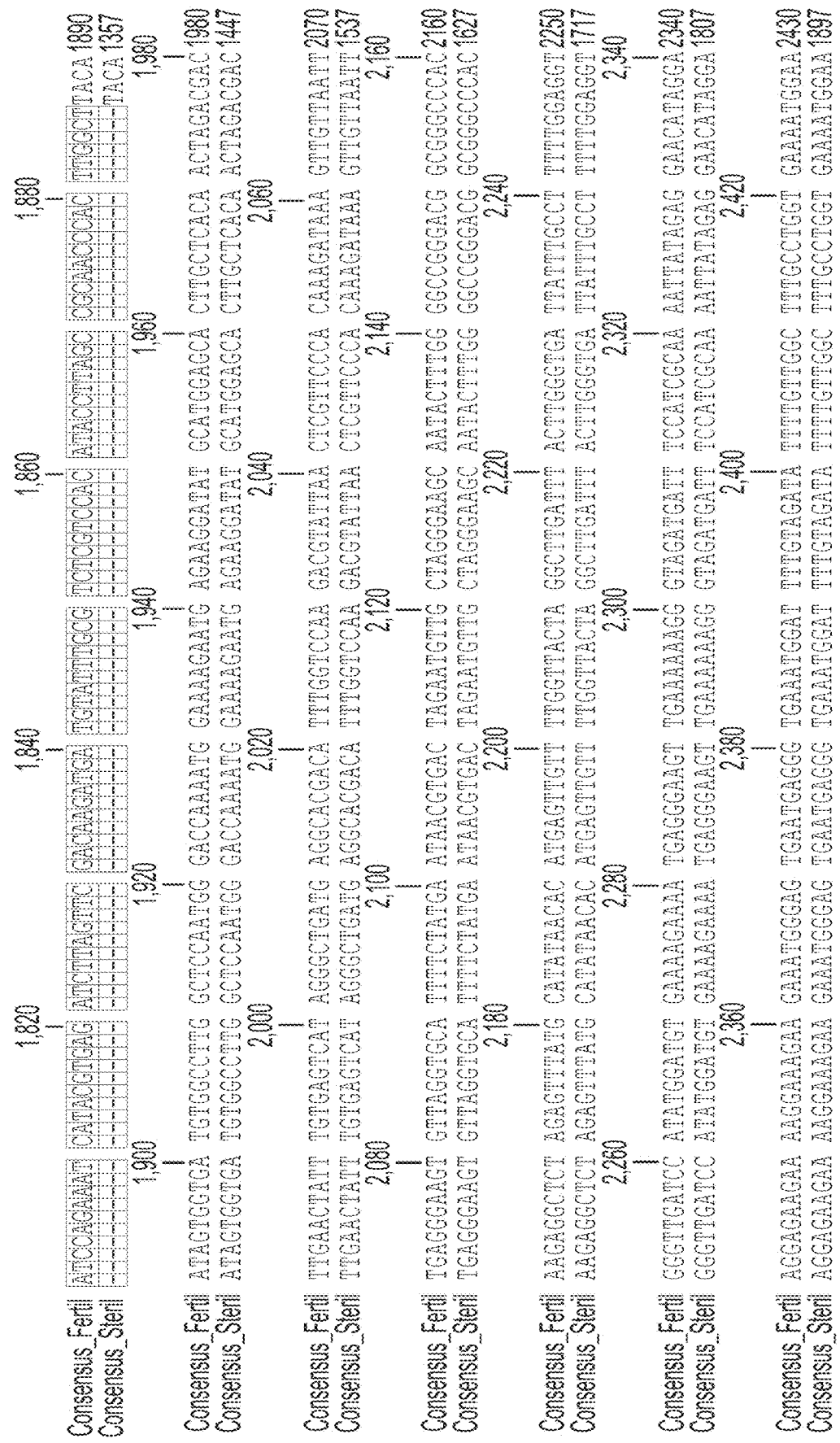
Figure 3:
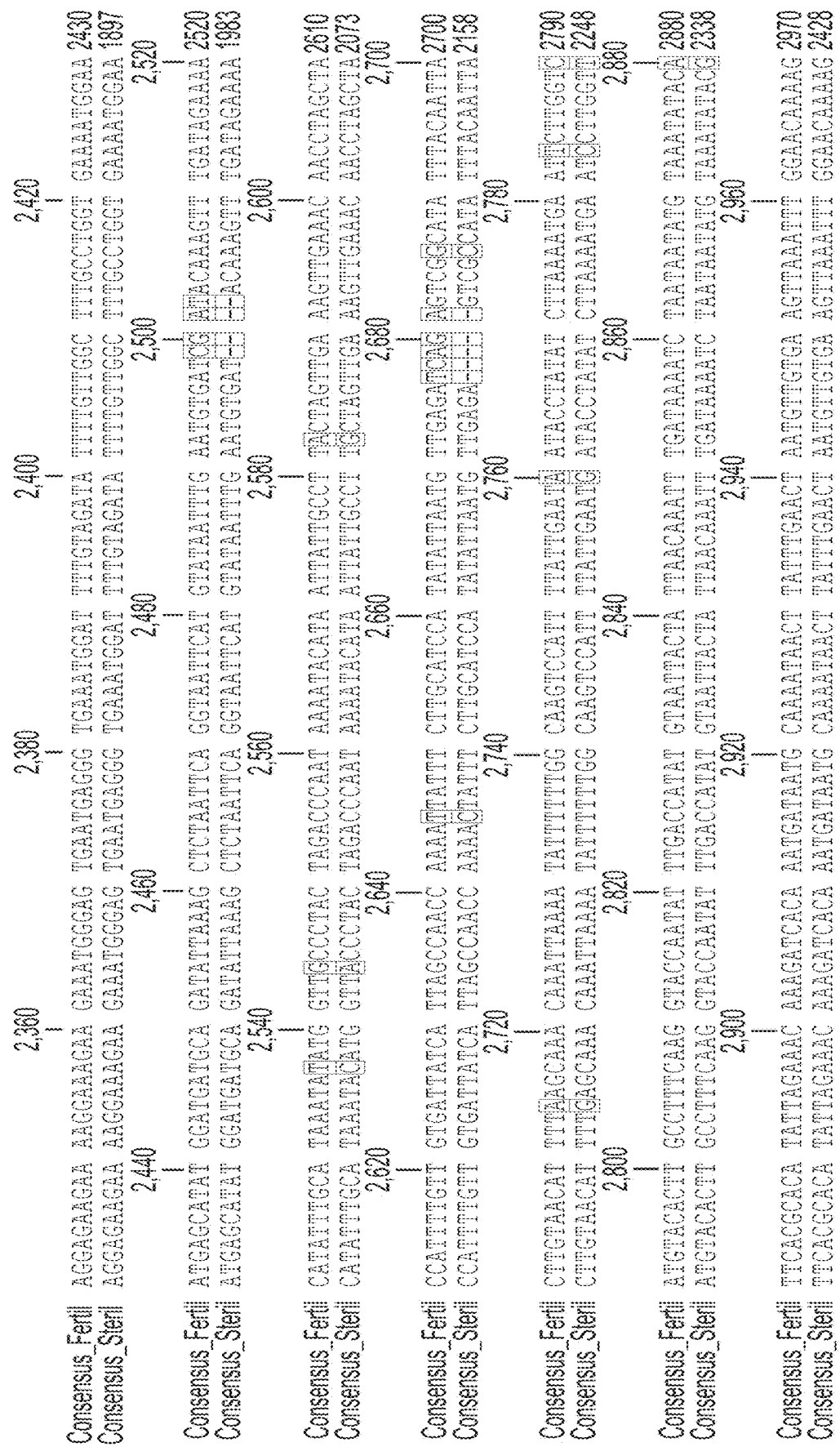
Figure 3:
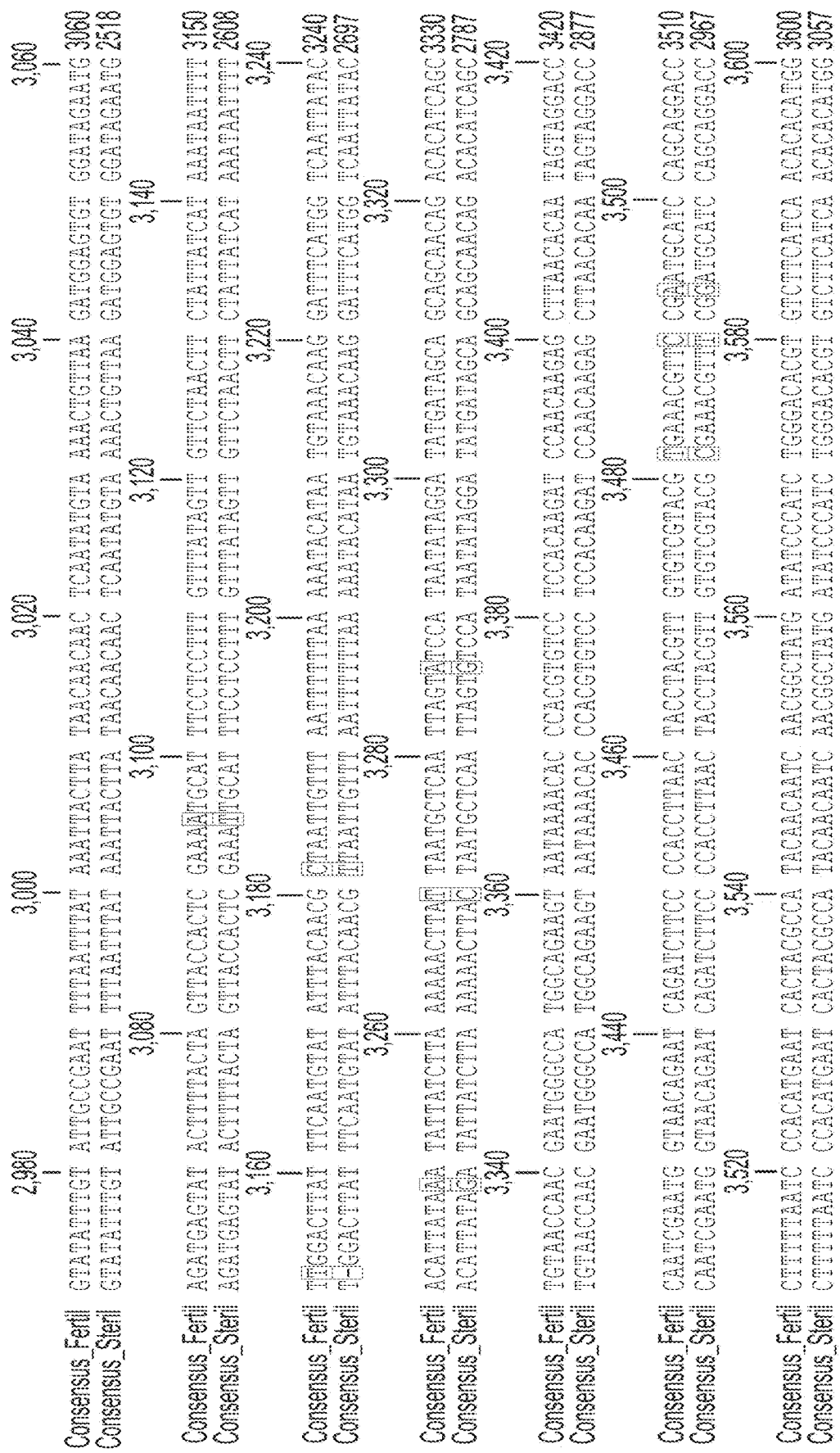
Figure 3:
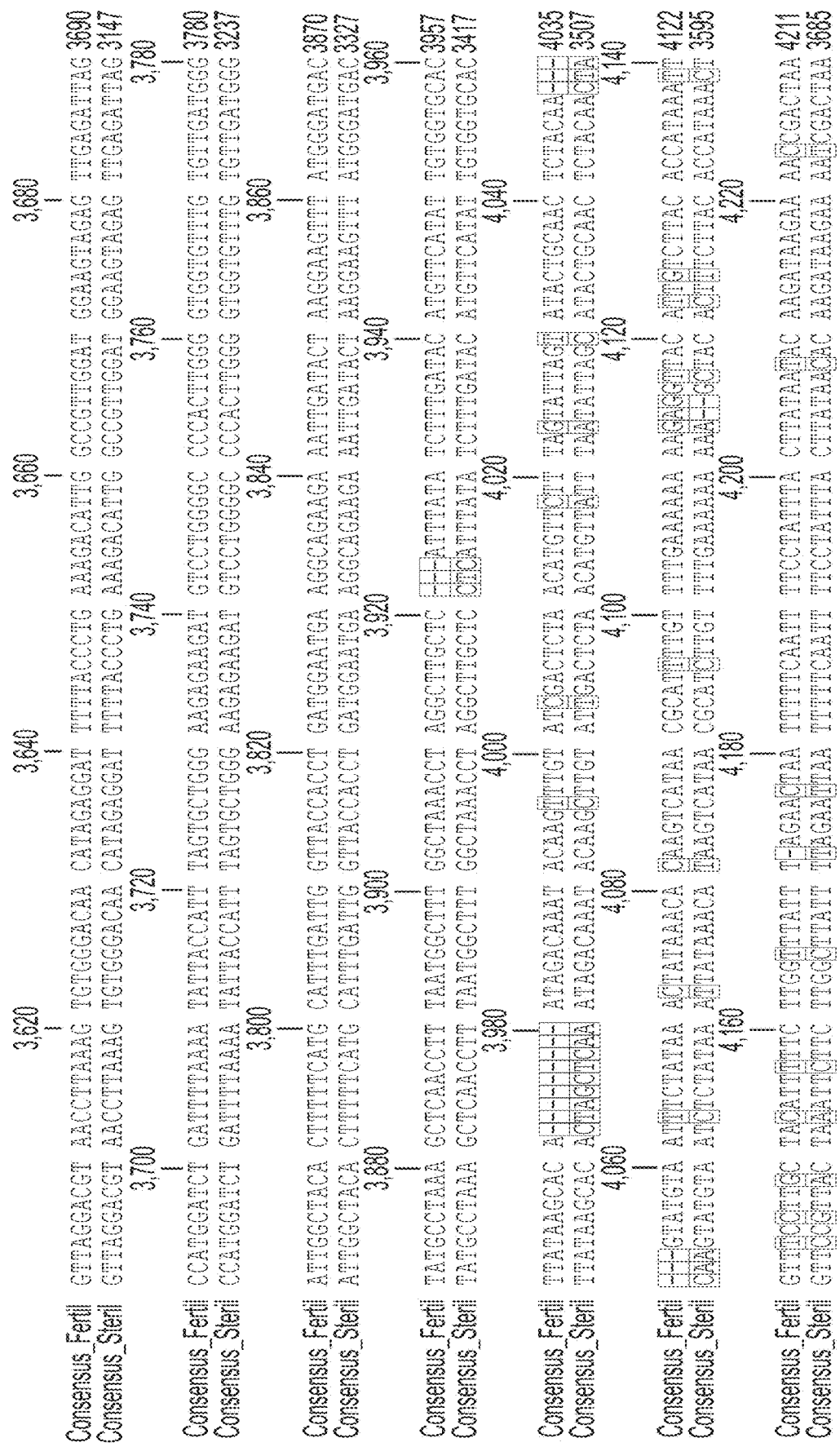

FIG. 3: Alignment of a 4721 bp genomic DNA fragment that encodes the sugar beet gene model of BvCYPgst (g6845.t1), from sterile (SEQ ID NO: 8) and fertile genotypes (SEQ ID NO: 28). The sequence of the sterile genotypes has a 533 bp deletion.

Figure 4:
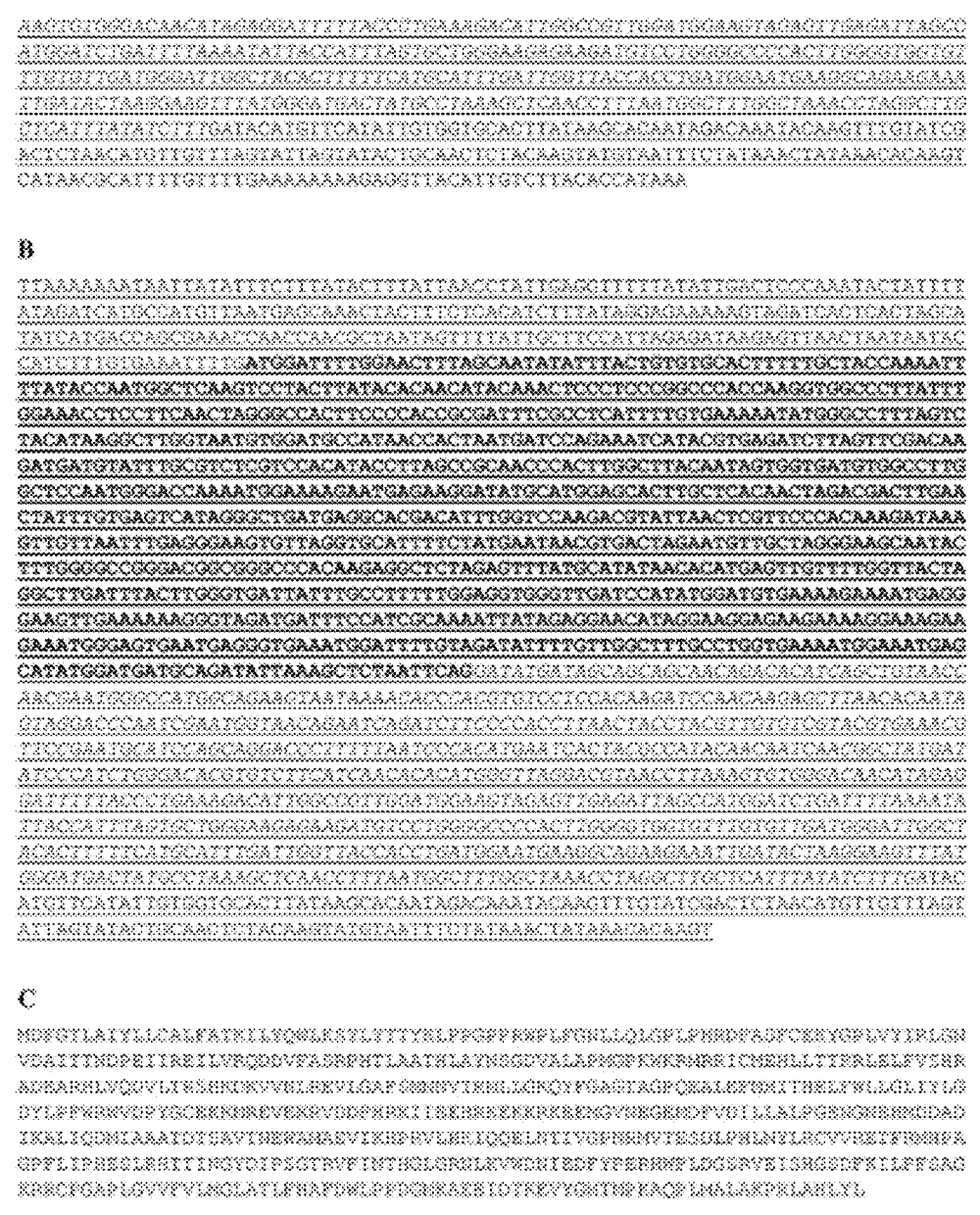
Figure 4:
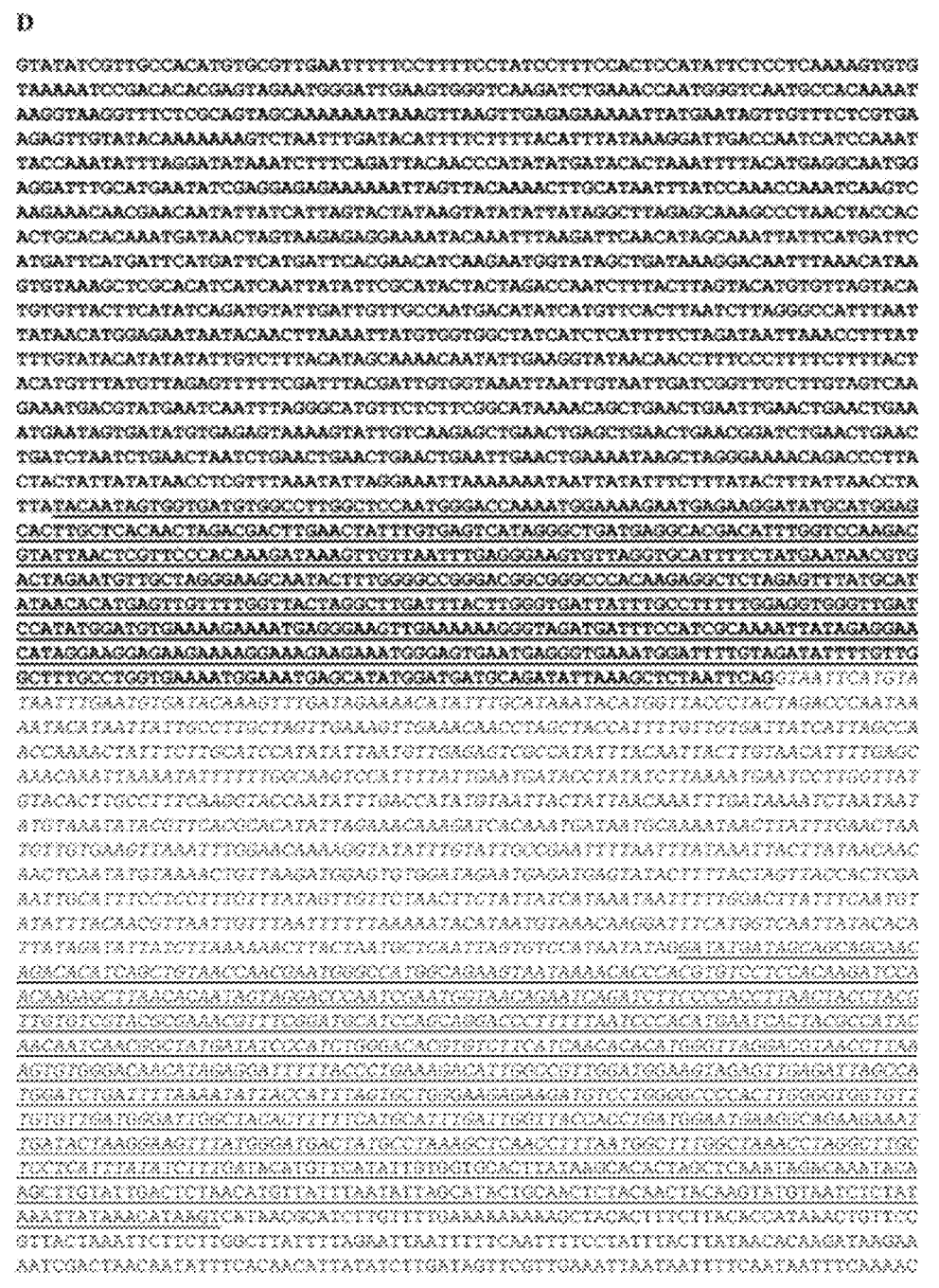

FIG. 4: A sequence analysis of the 4721 bp genomic DNA fragment that encodes the sugar beet gene BvCYPgst (g6845.t1), from sterile and fertile genotypes. A) shows the genomic DNA sequence of the CYPgst gene in *Beta vulgaris*, subspecies *vulgaris*, including the putative promoter region, as well as 5'UTR and 3'UTR. The putative promoter region is depicted in "bold," the 5'UTR and 3'UTR are underlined, exon 1 is in "bold" and underlined, exon 2 is in italics and underlined, and the intron is in italics. This sequence corresponds to the sequence in SEQ ID No. 1. The functional regions of the gene are located as follows: putative promoter 1 . . . 518; 5'UTR 1519 . . . 1761; transcribed region 1519 . . . 4275; exon 1762 . . . 2679; intron 2680 . . . 3506; exon 3507 . . . 4142; 3'UTR 4143 . . . 4275. B) shows the cDNA sequence of the CYPgst gene in *Beta vulgaris*, subspecies *vulgaris*, including the 5'UTR and 3'UTR. The 5'UTR and the 3'UTR are underlined, exon 1 is in "bold" and underlined, and exon 2 is in italics and underlined. This sequence corresponds to the sequence in SEQ ID No. 2. The functional regions of the cDNA are located as follows: 5'UTR 1 . . . 243; exon 244 . . . 1161; exon 1162 . . . 1787; 3'UTR 1798 . . . 1930. C) shows the amino acid sequence of the CYPgst gene in *Beta vulgaris*, subspecies *vulgaris*. This sequence corresponds to the sequence in SEQ ID No. 3. D) shows the genomic DNA sequence of the mutated CYPgst gene in *Beta vulgaris*, subspecies *vulgaris*, including the putative promoter region and 3'UTR. The putative promoter region is in "bold," the 3'UTR is underlined, the truncated exon 1 is in "bold" and underlined, exon 2 is in italics and underlined, and the intron is in italics. This sequence corresponds to the sequence in SEQ ID No. 8. The functional regions of the mutated CYPgst gene are located as follows: putative promoter 1 . . . 1353; transcribed region 1354 . . . 3542; truncated exon 1354 . . . 1938; intron 1939 . . . 2755; exon 2756 . . . 3394; 3'UTR 3395 . . . 3542.

Figure 5:
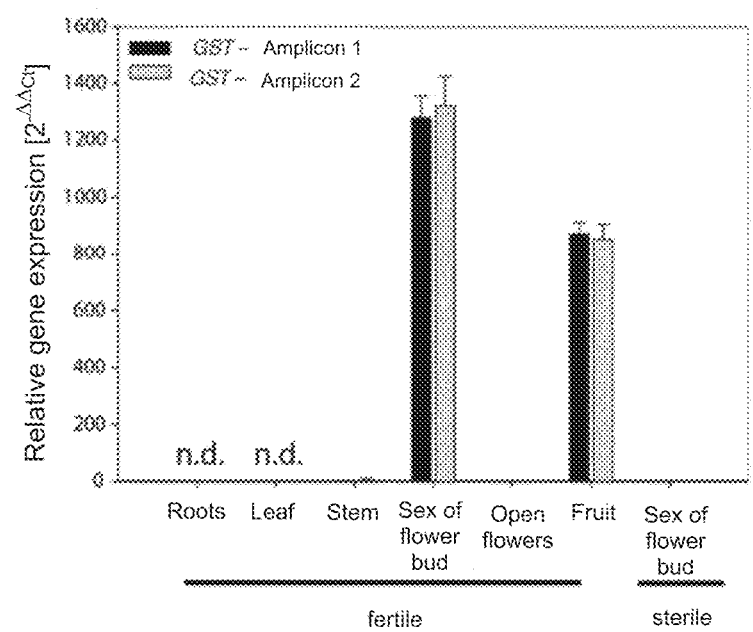

FIG. 5: An expression analysis of the gene BvCYPgst (GST, g6845.t1) by means of qRT-PCR. RNA is obtained from various tissues of fertile plants and the expression of the GST gene is depicted in comparison with the expression of the gene g4645.t1, where n.d. means no expression was detected. GST was most strongly expressed in the experiment shown here in closed flowers. In comparison, no expression of the GST gene could be detected in closed flowers of the sterile genotypes.

DETAILED DESCRIPTION OF THE INVENTION

The present invention produces a plant through mutation in a DNA segment of the nuclear genome that comprises a cytochrome P450 oxidase (CYPgst) gene exhibiting a nucleus-encoded male sterile phenotype. This is distinguished in that the mutation is obtained through a recessive trait expression, and the plant can thus be used to simplify labor intensive breeding programs. The identification of the gene responsible for this trait expression occurs in the sugar beet (*Beta vulgaris*, subspecies *vulgaris*), as explained in Examples 1 and 2 and FIGS. 1 to 5. The relevant gene is classified as a member of the cytochrome P450 oxidases (CYP) due to its structural features determined by sequence analysis, and provided with the suffix "gst" representative of the phenotype observed in its mutants for the nucleus-genetic male sterility. Because the gene in sugar beets is identified, the prefix "Bv" is also used when concrete reference is made to the gene described in the examples.

In general, the present invention relates to a plant, in particular a cultivated or crop plant that displays a recessive, nucleus-encoded male sterile phenotype, characterized in that the phenotype correlates with a mutation comprised in the endogenic cytochrome P450 oxidase (CYPgst) gene, or with the absence, or lower content or activity of a functional CYPgst protein in comparison with a corresponding (male fertile) wild type plant, which is encoded by the CYPgst wild type gene, characterized in that the non-mutated CYPgst gene is the gene BvCYPgst in *Beta vulgaris*, which comprises one of the nucleotide sequences in SEQ ID No. 1 or 2, or encodes the amino acid sequence in SEQ ID No. 3, or a homolog, analog, or ortholog thereof. As described above, and explained in the examples, other CYPgst proteins, or the encoding genes thereof, i.e. homologs, analogs, and orthologs can be identified in plants through classic bioinformatics approaches (data base searches and computer programs for screening for homologous sequences), wherein it can be assumed that a mutation of the same phenotype is triggered, as has been observed in sugar beets. A plant in the present invention is thus also characterized in that the non-mutated CYPgst gene is the gene StCYPgst in *Solanum tuberosum*, which preferably comprises a nucleotide sequence in SEQ ID No. 12 or 13, or encodes the amino acid sequence in SEQ ID No. 14, or a homolog, analog, or ortholog thereof; or that the non-mutated CYPgst gene is the gene ZmCYPgst in *Zea mays*, which preferably comprises the nucleotide sequence in SEQ ID No. 9 or 10, or encodes the amino acid sequence in SEQ ID No. 11, or a homolog, analog, or ortholog thereof.

The term "homolog(s)" therein means that the relevant genes (from two different types of plants) substantially have the same function and a common ancestor, and that their nucleic acids or encoded amino acid sequences are substantially identical. There are many genes, however, that are homologous to one another, without the protein sequences resulting in a useful pairing alignment. In contrast thereto, the term "analogous" genes or proteins (likewise) indicates that they have identical or similar functions, but are not obtained from the same structure, i.e. they do not have a common ancestor. In this case, their nucleic acids or encoded amino acid sequences are often not significantly identical, or at best, are only only in certain functional domains.

In the context of genome sequencing for annotation, "homolog" is more specifically defined. The terms "ortholog" and "paralog" are included therein. Orthologs are genes that bind via speciation. Paralogs are genes that bind via duplication.

A gene is fundamentally a homolog, analog, or ortholog as set forth in the present invention when it is capable of complementing the male sterile phenotype as it occurs in the reference gene CYPgst in sugar beets (BvCYPgst), and/or a targeted mutation is triggered in the relevant gene, or changes occur in the biological activity of the genetic products of a male sterile phenotype in the plant encoded by the homolog or analog from which the gene was obtained. Accordingly, the relevant homolog or analog to the CYPgst gene of the present invention illustrated in the example can preferably characterized in that it is capable of complementing the male sterile phenotype observed in the CYPgst mutants of the sugar beet, i.e. it can restore the fertile phenotype. Additionally or alternatively, the CYPgst homolog or analog can preferably be characterized in that a male sterile phenotype is obtained through inhibition of the expression thereof or the biological activity of the genetic product encoded by the homolog or analog. The male sterile phenotype preferably has the properties described by way of example for the CYPgst mutants in sugar beets, in particular those properties described in the examples; see the embodiments described above.

Corresponding techniques and methods for complementary genetics are known to the person skilled in the art from the prior art; see e.g. Napoli et al., Plant Physiology 120 (1999), 615-622, which describes a mutation in inbred strains of petunias, which also have a male sterile phenotype that can be eliminated through transgenic complementation with a functional chalcone synthase A cDNA, such that it could be determined that the chalcone synthase gene A is substantially responsible for the male sterile phenotype, or the phenotype for male sterility is caused through a mutation in this gene.

In Jeong et al., J. Exp. Bot. 65 (2014), 6693-6709, the male sterility in so-called ms10$^{35}$ tomato mutants is complemented and eliminated through complementation and by means of transgenic expression of various candidate genes. Methods for producing male sterility in transgenic plants through inhibition of a target gene, in this case CYPgst, are likewise known to the person skilled in the art; see e.g., international patent application WO 1996/017945 and the following embodiments.

Thus, in one embodiment of the present invention, a plant displaying a recessive, nucleus-encoded, male sterile phenotype is characterized in that the phenotype is caused by a mutation comprising the endogenic cytochrome P450 oxidase (CYPgst) gene. The plant according to the invention can also be characterized, however, by the absence, or low content in comparison with a corresponding male fertile wild type plant, or activity of a functional CYPgst protein encoded by the wild type gene from CYPgst. A genomic sequence of the mutated gene, which can no longer be translated, is shown in SEQ ID No. 8, but is only intended as an example, not limiting to the invention in this regard. In particular, the invention relates to a plant belonging to the cultivated and crop plants.

A deactivation of the CYP703 gene in *Arabidopsis thaliana* (CYP703A2) to obtain a reduced pollen formation and thus resulting in partial male sterility is described in the prior art (Morant et al., The Plant Cell, 19 (2007), 1473-1487). This can be attributed to the fact that the sporopollenin, forming the main component of the exposed layer of pollen, is absent or structurally altered. Although it seems plausible that the CYPgst gene assumes another function, because a mutation results in nucleus-encoded, recessive, male sterility, and pollen is not formed, the possibility that the CYPgst gene and the CYP703 gene from *Arabidopsis thaliana* belong to the same gene family and thus fulfill the same or at least similar function in the synthesis of sporopollenin should not be dismissed. Without committing to a specific theory, it seems plausible that the ability to compensate for the lack of sporopollenin has been lost in cultivated plants, which have been optimized over years of targeted selection and crossbreeding with regard to yield, pest resistance, tolerance of abiotic stress factors, and the content of plant substances, and that the absence of sporopollenin results in suppression of pollen formation, such that the plant is male sterile.

Because it is explained in Morant et al. (2007) that the CYP703A2 gene, or corresponding knockout lines of *Arabidopsis*, only exhibit partial male sterility, and such a phenotype is not suitable for hybridization, the CYP703A2 gene in *Arabidopsis thaliana*, or the mutants described in Morant et al., particularly those with the sequences shown in FIG. 1, are excluded from the present invention in one embodiment. Accordingly, in a preferred embodiment of the plants of the present invention, cultivated and/or crop plants of the type *Arabidopsis thaliana* are preferably excluded.

Plants have two or more copies of their genetic information in each cell in the form of eukaryotes. Each gene is normally represented by two alleles, which may be identical in the homozygous state, or different in the heterozygous state. The phenotype of the plant according to the invention is caused by a mutation in the nuclear genome, and this is obtained through a recessive trait expression. Accordingly, the plant is male fertile in one embodiment of the invention, when the mutation is heterozygous, and male sterile when the mutation is homozygous.

The formation of functional pollen is suppressed, preferably fully suppressed, in a sterile plant, wherein in conjunction with the present invention, the term "suppressed" means that in a plant that is homozygous for the mutation of the CYPgst gene and is male sterile, 95%, preferably 96%, more preferably 97%, particularly preferably 98%, and particularly preferably 99% of pollen formation does not take place, while "fully suppressed" means that more than 99%, preferably 100% of pollen formation is suppressed. In this context, "suppressed" preferably means that in a crossbreeding experiments with such a plant serving as the male parent and a corresponding wild type plant, substantially no seed production takes place and/or no descendants are generated.

In the case of *Beta vulgaris*, subspecies *vulgaris*, this is clear in FIG. 1. The light (yellow) vital anthers of the fertile genotype (A) can be seen in closed flowers that have had the sepals and petals manually removed. In contrast thereto, the anthers of the sterile genotypes are clearly dark (brown) (B). When flowering, the anthers of the fertile genotypes open and release pollen (C), while the anthers in sterile genotypes fail to mature, and do not release pollen (D).

In *Arabidopsis thaliana*, the CYP703 protein catalyzes the conversion of medium chain saturated fatty acids into the corresponding simple hydroxylated fatty acids, with a preferred hydroxylation of lauric acid at the C7 position. Without committing to a specific theory, it seems plausible that the CYPgst protein does not fulfill the same function as the CYP703 protein from *Arabidopsis thaliana*, but a similar one, because a deactivation of both genes has an effect on the pollen formation. Thus, a function in the synthesis of sporopollenin, the main component of the exposed layer vital pollen, can be attributed to CYPgst.

In one embodiment, the CYPgst protein therefore plays a role in the synthesis of the sporopollenin, and catalyzes the conversion of medium chain saturated fatty acids to form corresponding simple hydroxylated fatty acids, preferably with hydroxylation of lauric acid at the C7 position.

Transcription analysis (Example 2) in fertile genotypes of *Beta vulgaris* subspecies *vulgaris* shows that the CYPgst gene is expressed in closed flowers and fruit, and no expression is detected in roots and leaves (FIG. 5). Accordingly, one embodiment of the plant according to the invention is a plant described above, wherein the CYPgst gene is expressed at least in closed flowers and fruit, preferably specifically in closed flowers and fruit.

In one embodiment, the mutation prevents transcription and/or translation of a functional protein in the plant according to the invention, wherein the mutation is preferably a deletion, addition, insertion or substitution in the encoding nucleotide sequence of the CYPgst gene, a splicing signal, or a regulatory sequence, preferably the promoter sequence, of the CYPgst gene.

In a preferred embodiment, the deletion is a deletion of at least 500-600 bp, relating to the encoding region or the promoter region of the CYPgst gene. The deletion can also have a length of at least 20, 30, or 50 consecutive base pairs, at least 100, 150, 200, or 250 consecutive base pairs, or preferably at least 300, 400, or 500 consecutive base pairs. The addition is preferably an insertion of a nucleotide or numerous nucleotides in the genome sequence, preferably in the encoding gene sequence resulting in a reading frame shift. The substitution is preferably a point mutation in the genome sequence, preferably in the encoding sequence, that generates stop codons or splicing errors.

Through a comparative sequencing of genomic DNA fragments, comprising the CYPgst gene and the putative promoter region from both male sterile and male fertile *Beta vulgaris* subspecies *vulgaris* plants, it has been demonstrated that a deletion of 533 bp is responsible for the male sterile phenotype (see Example 2 and FIG. 3) and that the deletion lies between the nucleotide positions 1560 and 2095 in SEQ ID No. 1.

In another preferred embodiment, this is a deletion of 533 bp, comprising parts of the 5'UTR and the first exon of the CYPgst gene in *Beta vulgaris*, subspecies *vulgaris*; see FIG. 3. The functional gene BvCYPgst comprises two exons with a total length of 1554 bp. A gene model annotated in RefBeet 1.2 is shown in FIG. 2, and the genomic DNA sequence of CYPgst with the deletion resulting in a truncated exon 1 is given in SEQ ID No. 8. Possible point mutations that can result in a premature transcription interruption of the CYPgst gene in *Beta vulgaris*, subspecies *vulgaris*, or could cause a disrupted splicing, are listed in Table 1, wherein these preferably lie between the nucleotide positions 1560 and 2095 of SEQ ID No. 1.

As is shown in Example 1 of the present invention, closely flanking markers in the CYPgst gene could be identified through fine mapping, thus providing the position of the CYPgst gene in the genome of *Beta vulgaris*, subspecies *vulgaris*. This in turn provides the basis for developing male markers with which the deletion in the CYPgst gene could be detected.

Accordingly, in one embodiment of the present invention, the plant is characterized in that the deletion in sugar beets (*Beta vulgaris*, subspecies *vulgaris*) can be detected through the absence of one or both marker loci sle5983d14 (amplification product of the primer with SEQ ID Nos. 4 and 5) and sle5983d17 (amplification product of the primer with SEQ ID Nos. 6 and 7) and through the presence of a ubiquitous marker. The ubiquitous marker confirms the satisfactory quality of the DNA extraction.

Moreover, in another embodiment, the gene from *Beta vulgaris*, subspecies *vulgaris* (sugar beet) is located in a segment on chromosome 1 between marker loci sxn2151s01 and sle3305s02. In a preferred embodiment, these marker loci are at 33.42 or 35.15 cM on chromosome 1 (based on the genetic map ZR INT 1202) and based on the physical genome map (Physmapv2), this region has a physical size of 215.4 kbp, and lies between positions 3185718 bp and 3401120 bp. KASP markers (KASP™, SNP genotyping chemical from LGC Limited) have been developed, with which the SNP or the corresponding reference sequence that is to be detected can be identified. The sxn2151s01 marker sequence shown in SEQ ID No. 24 and the sle3305s02 marker sequence shown in SEQ ID No. 26 indicate the presence of the gst locus; the sxn2151s01 marker sequence shown in SEQ ID No. 25 and the sle3305s02 marker sequence shown in SEQ ID No. 27 indicate the reference sequence, wherein the marker sequences each differ at nucleotide position 21, and there is a "G" at this position in the genotype carrying the gst locus, and there is an "A" at this position in the reference genotype KWS2320.

In a preferred embodiment, the segment is approx. 50 to 5,000 kbp, preferably 100 to 1,000 kbp, more preferably 100 to 500 kbp, and particularly preferably 200 to 250 kbp. Wherein the segment has other protein encoding genes, preferably 21 genes.

In one embodiment of the present invention, the non-mutated gene is the functional gene BvCYPgst from *Beta vulgaris*, preferably *Beta vulgaris*, subspecies *vulgaris*, or a functional homologous, analogous, or orthologous gene of another crop plant or cultivated plant.

The person skilled in the art can derive other CYPgst proteins from the relevant literature, as well as data bases, using appropriate search profiles and computer programs to screen for homologous sequences, or for sequence comparisons. Moreover, the person skilled in the art can discover other CYPgst protein encoding DNA sequences using conventional molecular biology techniques, and make use thereof in the framework of the present invention. Appropriate hybridization probes, for example, can thus be derived from the sequence of the CYPgst gene, and used for screening genomic and/or cDNA data bases for the desired organism. The person skilled in the art can reference conventional hybridization, cloning and sequencing methods, listed by way of example in Sambrook et al., Molecular Cloning; A Laboratory Manual, 3$^{rd}$ ed., Cold Spring Harbor Laboratory Press, Cold Spring Harbor, N.Y., 2001. The person skilled in the art can also synthesize and use oligonucleotide primers for amplifying CYPgst sequences based on known sequences.

In particular, the homologous, analogous, or orthologous gene in a preferred embodiment is a gene from *Zea mays*; preferably comprising a nucleotide sequence displayed in SEQ ID No. 9 or 10; or encoding the amino acid sequence displayed in SEQ ID Na 11, or which preferably comprises one of the nucleotide sequences from *Solanum tuberosum* in SEQ ID No. 12 or 13, or encodes the amino acid sequence in SEQ ID No. 14; or from *Triticum aestivum*, which preferably encodes the amino acid sequence in SEQ ID No. 15; or from *Helianthus annuus*, which preferably encodes the amino acid sequence in SEQ ID No. 16; or from *Hordeum vulgare*, which preferably encodes the amino acid sequence in SEQ ID No. 17; or from *Brassica napus*, which preferably encodes the amino acid sequence in SEQ ID No. 18; or from *Brassica oleracea*, which preferably encodes the amino acid sequence in SEQ ID No. 19; or from *Brassica rapa*, which preferably encodes the amino acid sequence in SEQ ID No. 20; or from *Glycine max*, which preferably encodes the amino acid sequence in SEQ ID No. 21; or from *Gossypium*, which preferably encodes the amino acid sequence in SEQ ID No. 22; or from *Sorghum bicolor*, which preferably encodes the amino acid sequence in SEQ ID No. 23. The specified plants can be classified as crop plants, and preferably as cultivated plants.

One embodiment of the plant according to the invention is a plant described above wherein the non-mutated gene (wild type gene) has a nucleotide sequence selected from the group comprising a nucleotide sequence contained in the nucleotide sequence shown in SEQ ID Nos. 1, 2, 9, 10, 12, and 13.

In one embodiment, the non-mutated gene (wild type gene) has a nucleotide sequence that encodes the amino acid sequence shown in SEQ ID Nos. 3, 11, or 14.

The nucleotide sequence can be introduced into the gene using conventional methods known in the prior art, e.g. through site-directed mutagenesis, PCR induced mutagenesis, transposon mutagenesis, genome editing, etc., substitutions, deletions, insertions, additions and/or any other modification, either alone or in combinations thereof, which modify the nucleotide sequence but still fulfill the same function as the starting sequence.

Moreover, the invention also comprises a plant described above, wherein the nucleotide sequence can also include a functional fragment of the nucleotide sequences in SEQ ID Nos. 1, 2, 9, 10, 12 and 13. The term "fragment" comprises genes with a nucleotide sequence that is sufficiently similar to the aforementioned nucleotide sequence. The term "sufficiently similar" means a first nucleotide sequence or amino acid sequence that has a sufficient or minimum number of identical or equivalent nucleotides or amino acid residues with respect to a second nucleotide or a second amino acid sequence. Regarding the amino acid sequence, these also have a common structural domain after modification with one of the aforementioned methods, and/or they have a common functional activity. Nucleotide sequences or amino acid sequences that are at least approx. 45%, at least approx. 50%, at least approx. 55%, at least approx. 60%, at least approx. 65%, at least approx. 70%, at least approx. 75%, at least approx. 80%, at least approx. 85%, at least approx. 90%, at least approx. 95%, at least approx. 96%, at least approx. 97%, at least approx. 98%, at least approx. 99%, or at least approx. 100% identical, are defined here as sufficiently similar. A sufficient similarity is preferably established in the functional fragments when the nucleotide sequence or amino acid sequence has the same general property as the aforementioned nucleotide or amino acid sequences of the present invention.

Accordingly, the non-mutated gene (wild type gene) comprised in the plant has a nucleotide sequence in one embodiment that is able to hybridize, under stringent conditions, a nucleotide sequence that is complementary to a nucleotide sequence in SEQ ID No. 1, 2, 9, 10, 12, or 13, or to a nucleotide sequence that encodes the amino acid sequence in SEQ ID No. 3, 11, or 14. Moreover, another embodiment comprises the non-mutated gene (wild type gene) comprising a nucleotide sequence that encodes an amino acid sequence that has deviations with respect to the amino acid sequence in SEQ ID No. 3, 11, or 14 in the form of amino acid deletions, substitutions, additions, and/or insertions in the amino acid sequence, preferably over no more than 20%, 15%, 10%, 5%, 4%, 3%, 2% or 1% of the entire amino acid sequence.

In another or additional embodiment, the nucleotide sequence of the non-mutate gene (wild type gene) encodes a protein with the same enzymatic activity as the protein that is encoded by the DNA of the previous embodiment.

In another embodiment, the non-mutated gene (wild type gene) comprised in the plant has a DNA that comprises at least 200 or 400, preferably at least 600 or 800, particularly preferably at least 1,000 consecutive nucleotides from the promoter of the nucleotide sequence in SEQ ID No. 1, from the nucleotide positions 1 to 1518, preferably from the nucleotide positions 518 to 1518, particularly preferably from the nucleotide positions 1318 to 1518, or a sequence that is hybrid at this region, wherein the nucleotide sequence is able to control expression of the gene or a heterologous nucleic acid molecule that is operatively linked to the DNA, specifically in closed flowers and/or fruit.

In one embodiment, the plant can be an inbred plant or a hybrid plant. The inbred plant can be used as a parent plant for producing hydrides. The advantage of using a recessive, nucleus-encoded male sterile heterozygous inbred plant for the trait is that it divides into fertile and sterile individuals in each reproductive step. The male sterile individual can be used for producing hybrids, whereby there is no manual removal of the anthers, and it is no longer necessary to also maintain a sterile maintainer line.

In one embodiment, the plant according to the invention is a plant of the genus *Zea, Solanum, Triticum, Triticale, Helianthus, Secale, Hordeum, Brassica, Brachypodium, Glycine, Gossypium, Sorghum, Saccharum, Setaria, Aegilops, Oryza, Daucus, Eucalyptus, Erythranthe, Genlisea, Musa, Avena, Nicotiana, Coffea, Vitis, Cucumis, Morus,*

*Crucihimalaya, Cardamine, Lepidium, Capsella, Olimarabidopsis, Arabis, Raphanus, Eruca, Citrus, Jatropha, Populus*, or *Beta*, preferably a plant of the type *Zea mays, Solanum tuberosum, Triticum aestivum, Triticum durum, Triticum spelta, Helianthus annuus, Secale cereal, Hordeum vulgare, Hordeum bulbosum, Brassica napus, Brassica oleracea, Brassica rapa, Brassica juncacea, Brassica nigra, Glycine max, Gossypium sp., Sorghum bicolor, Triticale, Saccharum officinarum, Setaria italica, Oryza sativa, Oryza minuta, Oryza australiensis, Oryza alta, Brachypodium distachyon, Hordeum marinum, Aegilops tauschii, Daucus glochidiatus, Daucus pusillus, Daucus muricatus, Daucus carota, Eucalyptus grandis, Erythranthe guttate, Genlisea aurea, Musa sp., Avena sp., Nicotiana sylvestris, Nicotiana tabacum, Nicotiana tomentosiformis, Solanum lycopersicum, Coffea canephora, Vitis vinifera, Cucumis sativus, Morus notabilis, Crucihimalaya himalaica, Crucihimalaya wallichii, Cardamine flexuosa, Lepidium virginicum, Capsella bursa-pastoris, Olimarabidopsis pumila, Arabis hirsute, Raphanus sativus, Eruca vesicaria sativa, Citrus sinensis, Jatropha curcas, Populus trichocarpa* or *Beta vulgaris*. These plants belong to crop plants, in particular cultivated plants.

A further embodiment of the present invention comprises not only the plant according to the invention that has a mutation in the CYPgst gene, but also a DNA molecule that has a nucleotide sequence as defined above, with a mutation in the form of a deletion, addition, insertion, or substitution, wherein this mutation results in no synthesis of functional CYPgst protein.

In a preferred embodiment, the mutation in the encoding nucleotide sequence of the CYPgst gene is a splicing signal or a regulatory sequence of the CYPgst gene, preferably located in the promoter of the CYPgst gene. The mutation can be a deletion between the nucleotide positions 1560 and 2095 of SEQ ID No. 1 or corresponding positions in SEQ ID Nos. 12 or 9. The deletion can have a length of at least 20, 30 or 50 consecutive base pairs, preferably at least 100, 150, 200 or 250 consecutive base pairs, and particularly preferably at least 300, 400, or 500 consecutive base pairs. In a particularly preferred embodiment, the nucleic acid molecule comprises a nucleotide sequence according to that in SEQ ID No. 8. In another preferred embodiment, the nucleic acid molecule has a point mutation in the nucleotide sequence of SEQ ID No. 1 according to Table 1, preferably between the nucleotide positions 1560 and 2095 of SEQ ID No. 1.

As explained above, DNA hybridization probes derived from the sequence of the CYPgst gene can be used for screening genomic and/or cDNA data bases of other organisms, to identify homologous genes. In order to obtain a specific hybridization, such probes should be specific, and have a length of at least 15 nucleotides, preferably at least 20 nucleotides. The probes can be used for amplifying the identified homologous genes through the known process of polymerase chain reaction (PCR). Moreover, these probes can also be used for detecting mutations in the CYPgst gene. Comprehensive instructions for the hybridization of nucleic acids can be found in Tijssen, Laboratory Techniques in Biochemistry and Molecular Biology—Hybridization with Nucleic Acid Probes, Part 1, Chapter 2, "Overview of Principles of Hybridization and the Strategy of Nucleic Acid Probe Assays," Elsevier, New York (1993); and in Current Protocols in Molecular Biology, Chapter 2, Ausubel et al., eds., Greene Publishing and Wiley Interscience, New York (1995).

Therefore, a nucleic acid molecule of at least 15, 16, 17, 18, 19, or 20, preferably at least 21, 22, 23, 24, or 25, particularly preferably at least 30, 35, 40, 45, or 50, and very particularly preferably at least 100, 200, 300, 500, or 1,000 nucleotides is the subject matter of the present invention, wherein this nucleic acid molecule is specifically hybridized on a nucleotide sequence described above, comprising the non-mutated CYP703 wild type gene, or on a DNA molecule described above, with a mutation in the form of a deletion, addition, insertion, or substitution, resulting in no functional CYP703 protein being formed. The nucleic acid molecule preferably has the embodiment described in paragraph [17].

The position of the CYPgst gene in the genome of *Beta vulgaris*, subspecies *vulgaris*, can be determined with the fine mapping described above. This in turn provides the basis for developing genetic markers with which the deletion in the CYPgst gene can be detected.

The present invention therefore also relates to markers in the form of oligonucleotides, in particular primer oligonucleotides, in addition to the plants described above. These comprise a nucleic acid molecule of at least 15 nucleotides, hybridized specifically on nucleotide sequence as defined above, or on a DNA molecule defined above, with a mutation in the form of a deletion, addition, insertion, or substitution, resulting in no functional CYPgst protein being formed. These oligonucleotides preferably have a length of no more than 50 nucleotides. More preferably, the oligonucleotides are even shorter, and have a length of 15 to 25 nucleotides. As Example 2 of the present invention shows, the oligonucleotides preferably have one of the following nucleotide sequences: (i) SEQ ID No. 4, 6 or a complement thereof, or (ii) SEQ ID No. 5, 7, or a complement thereof.

The subject matter of the present invention also comprises a CYPgst protein that can be encoded by a nucleotide sequence described above and a functional and/or immunologically active fragment thereof, and an antibody that binds specifically to the CYPgst protein on the fragment thereof described herein. The recombinant production of proteins and fragments is known to the person skilled in the art and described, by way of example, in Sambrook et al., Molecular Cloning; A Laboratory Manual, $3^{rd}$ ed., Cold Spring Harbor Laboratory Press, Cold Spring Harbor, N.Y., 2001, or Wingfield, P. T. 2008, Production of Recombinant Proteins, Current Protocols in Protein Science, 52:5.0:a5.0.1-5.0.5. Polyclonal or monoclonal antibodies of the protein in the present invention can be produced by the person skilled in the art according to known methods, such as those described in E. Harlow et al., Antibodies: A Laboratory Manual (1988). The production of monoclonal antibodies and Fab and $F(ab')_2$ fragments, which can also be used in protein detection methods, can be carried out with various conventional methods, such as those described in Goding, Monoclonal Antibodies: Principles and Practice, pp. 98-118, New York; Academic Press (1983). The antibody can then be used for the screening of expression cDNA libraries to identify identical, homologous, or heterologous genes by means of immunological screening (Sambrook et al., Molecular Cloning; A Laboratory Manual, Cold Spring Harbor Laboratory Press, Cold Spring Harbor, N.Y., 1989, or Ausubel et al., 1994, "Current Protocols in Molecular Biology," John Wiley & Sons).

In a preferred embodiment, the CYPgst protein relates to the amino acid sequences in SEQ ID Nos. 3, 11, or 14 to 23, or an amino acid sequence that is identical at least to 80%, 82%, 84%, 86%, or 88%, preferably to 90%, 91%, 92%, 93%, 94%, or 95%, particularly preferably to 96%, 97%, 98%, 99% or 99.5%, preferably over the entire length of the amino acid sequence in SEQ ID No. 3.

The invention also relates to a recombinant DNA molecule comprising the non-mutated CYPgst gene (wild type gene), and has the aforementioned properties of the nucleotide sequence comprised in the plant according to the invention. The recombinant DNA molecule preferably has a promoter and/or other transcription or translation control element, or is associated therewith. The promoters that are used are mainly cell-specific promoters, which only allow the transcription of DNA in predetermined cells. In addition to the promoters, there are many other transcription control elements, e.g. enhancers, operators, repressors, and transcription termination signals, but not limited thereto, which are functionally attached to the DNA for enabling a targeted, cell-specific transcription. Promoters and other transcription regulation elements are known in general and available to the person skilled in the art; see, e.g., WO 00/75359, p. 23, line 5 to p. 24, line 17. This recombinant DNA molecule can be used to restore fertility in plants with a nucleus-encoded, recessive, male sterile phenotype.

Because, as explained above, the CYPgst gene is expressed in closed flowers and fruit, and not in roots or leaves, the recombinant DNA molecule in a preferred embodiment comprises either a promoter, which has a nucleotide sequence described above and is operatively linked to a heterologous nucleotide sequence, or an encoding nucleotide sequence, as defined above, which comprises the wild type CYPgst gene and is operatively linked to a heterologous promoter. This promoter is preferably able to control the expression of the nucleotide sequence, specifically in closed flowers and/or fruit. The recombinant DNA molecule more preferably comprises the native promoter of the non-mutated CYPgst gene from *Beta vulgaris*, subspecies *vulgaris* (SEQ ID No. 1).

Accordingly, the present invention also comprises the use of the DNA molecule described herein, or the promoter for specific expression of heterologous nucleic acid molecules in plant flowers and/or fruit. This requires an operative linking of the heterologous nucleic acid molecule to the corresponding promoter, and the introduction of this recombinant DNA molecule in the target cell, preferably a plant cell. Methods for heterologous expression of recombinant DNA molecules shall be explained in greater detail below.

Another subject matter of the present invention comprises a recombinant DNA molecule with a nucleotide sequence according to the invention, which encodes an shRNA (small hairpin RNA), siRNA (small interfacing RNA), negative sense RNA, positive sense RNA or double-strand RNA. These convey inhibition of the translation of the CYPgst mRNA or the breakdown of the CYPgst mRNA in the cell through base pairs. Accordingly, the introduction and/or expression of the recombinant DNA molecule in a plant results in inhibition of the expression of the functional (non-mutated) CYPgst gene. In a preferred embodiment, the nucleotide sequence exhibits properties that are described in detail in paragraph [15].

A further subject matter of the invention comprises vectors, which comprise recombinant DNA molecules or nucleic acid sequences or nucleic acid molecules of the present invention. A vector according to the invention can contain the non-mutated CYPgst gene (wild type gene) with the aforementioned properties of the nucleotide sequence and preferably one of the promoters described above. Another vector can contain a recombinant DNA molecule, which comprises the non-mutated CYPgst wild type gene that is linked to a heterologous nucleic acid molecule, or can contain a recombinant DNA molecule that comprises a nucleotide sequence described above, which is operatively linked to a heterologous promoter, wherein in each case, the promoter is preferably able to specifically control the expression of the nucleotide sequence in closed flowers and/or fruit. Moreover, a vector can contain a recombinant DNA molecule that has a nucleotide sequence, which encodes for an shRNA, siRNA, negative sense RNA, positive sense RNA, or double-strand RNA, and thus results in inhibition of the expression of the CYPgst gene after expression in a plant cell.

Furthermore, a vector can contain a DNA molecule with one of the mutations described above, or it can contain the nucleic acid molecule described above, which binds specifically to the non-mutated (wild type) CYPgst nucleotide sequence or to the mutated CYPgst nucleotide sequence.

The described vector can be a plasmid, cosmid, phage or expression vector, a transformation vector, shuttle vector, or cloning vector, and it can be double or single stranded, linear or circular, or it can transform a prokaryotic or eukaryotic host, either through integration in the genome thereof or extrachromosomally. The DNA molecule or nucleic acid molecule according to the invention is operatively linked to one or more regulatory sequences in an expression vector, which permit transcription, and optionally, expression in a prokaryotic or eukaryotic host cell; see, e.g., Sambrook et al., Molecular Cloning: A Laboratory Manual, 3$^{rd}$ ed., Cold Spring Harbor Laboratory Press, Cold Spring Harbor, N.Y. 2001, and the international patent application WO 00/75359, p. 21, line 20 to page 22, line 32. These regulatory sequences are preferably promoters or terminators, in particular for a transcription initiation starting point, a ribosome binding site, an RNA processing signal, a transcription termination site, and/or a polyadenylation signal. The vectors normally also contain indicator/reporter genes or resistance genes for detecting the transfer of the desired vector, or DNA molecules/nucleic acid molecules, and for selecting the individuals that contain these, because direct detection via the expression of the gene is usually rather difficult. Examples of indicator/reporter genes are, e.g., the luciferase gene and the gene that encodes for green fluorescent protein (GFP). These also permit testing for the activity and/or regulation of a promoter for the gene. Examples of resistance genes, specifically for plant transformations, are the neomycin phosphotransferase gene, the hygromycin phosphotransferase gene, or the gene that encodes for phosphinothricin acetyltransferase. These do not exclude other indicator/reporter genes or resistance genes known to the person skilled in the art. In a preferred embodiment, the vector is a plant vector.

A further subject matter of the invention is a vector described above, wherein the DNA molecule as a transgene is able to express a functional CYPgst gene, and is preferably genetically coupled to another transgene, which prevents transfer of the DNA molecule via pollen. The fertility can be restored by introducing this vector in a mutant that is male sterile through a mutation in the CYPgst gene. Because transfer of the transgenic functional CYPgst via pollen is prevented, only hemizygous seeds are obtained with the self-pollination of the transgenic line.

The vector, or the transgene, respectively, preferably also has an expression cassette, which marks the seeds, preferably using fluorescent marking. It is possible to easily differentiate transgenic seeds from non-transgenic seeds with this method. This system for using nucleus-encoded, male sterility was developed by the company Pioneer. The system with the name SEED PRODUCTION TECHNOL- OGY (SPT) (US 2006288440 A1) was developed for corn, and is based on the fact that a sterile mutant that has a mutation in a known nucleus-encoded gene, can be restored by inserting a transgene. The transgene contains the non-mutated allele of the sterility gene, such that the transgene functions as a wild type allele. The fertility restoring transgene is genetically coupled to another transgene, which prevents transfer of the transgene via pollen (pollen killer). As a result, only hemizygous seeds are produced through the self-pollination of the transgenic line, playing a major role in the efficiency of the system.

The transgene also contains an expression cassette that marks the seeds with red fluorescence. As a result, transgenic seeds can be easily differentiated from non-transgenic seeds. Because the transgenic seeds are fertile, the plants are automatically separated into fertile and sterile plants. The mother plants necessary for hybrid production are thus obtained by sowing the non-transgenic seeds, and the transgenic seeds can be used as the paternal line for further reproduction of the maternal line (Maintainer line), and also can be reproduced through simple selfing (FIG. 5). The SPT system can theoretically be applied to all types of plants. This requires the presence of a genetically male sterile line and knowledge of the gene responsible for the genetic male sterility phenotype. As a result, the SPT system could theoretically also be used for developing a hybrid system for every type of cultivated plant, such as the sugar beet or potato.

The present invention also relates to host cells that contain the described vectors, recombinant DNA molecules and/or nucleic acid molecules. A host cell as set forth in the invention can be a prokaryotic (e.g. bacterial) or eukaryotic cell (e.g. a plant cell or yeast cell). The host cell is preferably an agrobacterium or a plant cell. The present invention more preferably relates to a transgenic plant cell comprising the nucleic acid molecule according to the invention as a transgene or the vector of the present invention. Such a transgenic plant cell is a plant cell, for example, that is transformed, preferably in a stable manner, with the nucleic acid molecule according to the invention. In a preferred embodiment of the transgenic plant cell, the nucleic acid molecule is operatively linked to one or more regulatory sequences, which permit the transcription, and optionally the expression, in the plant cell. The overall structure comprising the nucleic acid molecule and the regulatory sequences thus represents the transgene. Such regulatory sequences comprise a promoter or a terminator, by way of example. The person skilled in the art knows of numerous functional promoters and terminators that can be used in plants.

The identification of the CYPgst gene that is responsible for the trait expression of the recessive, nucleus-encoded male sterility, is also used in the invention to produce transgenic plants with this trait expression and to thus restore fertility.

In one embodiment, a kit is claimed, which comprises the recombinant DNA molecules, or nucleic acid molecule sand vectors, respectively, described above, which are necessary for producing plants with nucleus-encoded, recessive male sterility, as well as to restoring fertility in plants with this phenotype. This kit also contains recombinant DNA molecule, which either comprise the promoter with a previously defined nucleotide sequence, or a heterologous promoter, where the former is linked to a heterologous nucleic acid molecule, and the latter is linked to a previously defined nucleotide sequence encoded for the non-mutated (wild type) CYPgst gene. Moreover, the kit can contain a vector, wherein the DNA molecule as a transgene is able to express a functional CYPgst gene, and is preferably genetically coupled to another transgene that prevents transfer of the DNA molecule via pollen, and has an expression cassette that marks the seeds. The kit can contain a previously defined nucleic acid molecule for identifying the mutation in the CYPgst gene, that hybridizes on a previously described nucleotide sequence comprising the non-mutated (wild type) CYPgst gene or on the corresponding gene with a previously defined mutation, or it can contain the oligonucleotide defined above. The kit can also contain the CYPgst gene described above, or a fragment thereof, as well as the above antibodies. The kit also preferably contains reagents for nucleic acid-based or immunological detection methods.

A transgenic plant is a plant, for example, that contains plant cells that are transformed with the DNA molecule/nucleic acid molecule according to the invention, or with the vector of the present invention. In a preferred embodiment of the transgenic plant, the DNA molecule/nucleic acid molecule is operatively linked to one or more regulatory sequences that permit transcription, and optionally the expression in the plant. The overall structure comprised of the nucleic acid molecule according to the invention and the regulatory sequences thus represents the transgene. The term "transgene" thus refers to a recombinant polypeptide-encoding nucleic acid sequence.

The oligonucleotides, nucleic acids, DNA molecules and vectors described above can also be used to produce a transgenic plant. The present invention therefore also relates to the use of these in producing a transgenic plant that displays a recessive, nucleus-encoded, homozygous male sterile phenotype, characterized in that the expression of the CYPgst gene is inhibited in the production of a plant according to the invention with restored fertility or in the production of a transgenic host cell, preferably a plant cell. Furthermore, the oligonucleotides, nucleic acids, DNA molecules and vectors described above can also be used in the corresponding methods for producing these transgenic plants or plant cells. The transgenic plant is preferably a crop plant or more preferably a cultivated plant.

There are various methods in the prior art with which transgenic plants can be produced and identified or selected, in which either the transcription/translation of a protein is suppressed or the restoration feature is introduced. Methods for producing transgenic cultivated plants and the identification thereof though molecular biology methods are known to the person skilled in the art; see, e.g., for transgenic glyphosate-resistant sugar beets, international patent applications WO 99/023232 and WO2004/074492, or for the transformation of plants in general, WO2000/018939 and WO2013/138309.

Accordingly, one embodiment of the invention is a method for producing a plant displaying a recessive, nucleus-encoded, homozygous male sterile phenotype, characterized in that the expression of the CYPgst gene is inhibited, wherein this plant is preferably a crop plant, and more preferably a cultivated plant. A recombinant DNA molecule expressing a polynucleotide is introduced into the plant cell by means of transformation, e.g. using a vector, such that the expression of the polynucleotide results in inhibition of the CYPgst protein.

By way of example, the mutation described above resulting in inhibition of the CYPgst expression can be obtained through genetic recombination during a crossbreeding process between the plants, wherein one of the plants carries the mutated CYPgst allele.

In addition to the use of conventional breeding programs for generating a genetic recombination, modern biotechnology provides the person skilled in the art with numerous other tools that enable a precise genome engineering. By way of example, T-DNA tagging can be used to destroy the CYPgst gene through insertion mutagenesis. Furthermore, the CYPgst gene can be entirely or partially deleted through genetic mutation, by means of TALE nucleases (TALENs) or zinc finger nucleases (ZFNs) and CRISPR/Cas systems, which have been described in WO 2014/144155 A1 (Engineering Plant Genomes Using CRISPR/Cas systems) and in Osakabe & Osakabe, Plant Cell Physiol., 56 (2015), 389-400, such that an expression of the CYPgst gene is prevented. This can also be achieved using the method referred to as TILLING (*Targeted Induced Local Lesions in Genomes*), wherein point mutation, as described in the German patent application DE 10 2013 101 617, for example, is caused in the wild type gene, and plants are subsequently selected that display a suitable, i.e. resistance-providing, gene, e.g. a barley that exhibits resistance to the yellow mosaic virus; see DE 10 2013 101 617, pp. 4, 8, and 12 in paragraphs [0014], [0026], and [0038]. The TILLING method is also described comprehensively in the publication by Henikoff et al. (Henikoff et al., Plant Physiol., 135, 2004, 630-636). Point mutations in the CYPgst gene in *Beta vulgaris*, subspecies *vulgaris*, that might result in stop codons or spicing errors are listed in Table 1.

An inhibition of the expression is also possible with RNAi approaches or co-suppression. These comprise introducing the recombinant DNA molecule or nucleic acid molecule defined above, or the corresponding vector, into the plant, wherein the expression of the encoded shRNA, negative sense RNA, or positive sense RNA molecules results in inhibition of the expression of the CYPgst gene. Such RNAi and/or co-suppression based methods are typical methods for inhibiting gene expression and are known to the person skilled in the art. A positive sense approach, comprising a target-specific non-polyadenylate RNA molecule, can result in inhibition of the CYPgst gene expression. This method is described by way of example in the international patent application WO2001/012824.

A further embodiment of the invention comprises a method for restoring fertility in a plant according to the invention, comprising the introduction of a functional CYPgst gene into the plant. The CYPgst gene can be introduced using genetic engineering methods; by means of a recombinant DNA according to the invention, preferably containing transcription control elements, preferably a promoter for the specific expression of the gene in closed flowers and/or fruit, or by means of the vectors according to the invention. The CYPgst gene can also be introduced through crossbreeding with a plant that carries the CYPgst wild type gene or a functional CYPgst gene, preferably in the homozygous state. Optionally, a selection for the presence of the CYPgst wild type gene or the functional CYPgst gene can take place in the descendants following the crossbreeding.

The subject matter of the present invention is a plant that contains a previously defined plant cell and/or that is obtained through the method described above. This means a plant with a nucleus-encoded, recessive male sterile phenotype, as well as a plant with restored fertility, is either produced through genetic recombination using conventional breeding methods or it is a transgenic plant in which the expression of the CYPgst gene is inhibited through the various aforementioned methods, resulting in a nucleus-encoded, recessive, male sterile phenotype, or in the restoration of the fertility through the introduction of recombinant DNA molecules. This plant is preferably a cultivated plant, particularly preferably a crop plant, preferably with storage organs, which can potentially also function as reproductive organs, such as beet roots or tubers from sugar beets and potatoes, grain from triticale, oats, millet and corn, fruit, e.g. tomatoes, etc. In one embodiment, the lower plants and the thale cress *Arabidopsis thaliana* are explicitly excluded from the present invention.

In addition to the plants that exhibit a nucleus-encoded, recessive, male sterile phenotype through spontaneous mutation in the CYPgst gene, or the plants in which this phenotype is added through genetic recombination using conventional breeding methods, or the plants in which this phenotype has been added through genetic engineering using modern biotechnology, and the plants in which the fertility has been restored through corresponding methods, the invention also relates to organs, plant parts, tissues, cells, and seeds or descendants of these plants. In one embodiment, the seeds or descendants have one or more of the mutations defined above, which lead to inhibition of the CYPgst gene expression and/or the seeds or descendants exhibit a recombinant DNA molecule or nucleic acid molecule or vector described above.

A method for identifying a plant according to the invention likewise forms one embodiment. Both the plant that exhibits a nucleus-encoded, recessive, male sterile phenotype through spontaneous mutation in the CYPgst gene as well as a plant in which this phenotype was added through genetic recombination suing conventional breeding methods or a plant in which this phenotype was added through genetic engineering using modern biotechnology can be identified with this method. Furthermore, a plant in which the fertility has been restored through the corresponding method can be identified with this method. A previously defined nucleic acid molecule serving as a hybridization probe can be used to identify this plant according to the invention, having a minimum length of 15 nucleotides and which binds specifically on a previously defined nucleotide sequence comprising the non-mutated (wild type) CYPgst gene and the CYPgst gene with a previously defined mutation that results in inhibition of the gene expression. Furthermore, the oligonucleotide defined above, the CYPgst protein defined above or a fragment thereof, and the antibodies as well as components of the kit described above can be used for the identification.

The present invention also relates to the use of recombinant DNA molecules or nucleic acid molecules, vectors according to the invention, and components of the kit according to the invention for producing a recessive, nucleus-encoded, male sterile plant, for producing a plant with restored fertility, for producing a hybrid plant, in resistance breeding programs, or for seed production.

A method for producing reversible male sterility in a plant, in which the CYPgst gene can be used, is described by way of example in the international patent application WO96017945, comprising:
(a) introduction of a first recombinant DNA molecule into the genome of a pollen producing plant that can be genetically transformed, wherein the first recombinant DNA molecule comprises:
  (i) a nucleotide sequence that encodes a genetic product that inhibits the pollen formation or function, depending on the expression in the plant, in this case the CYPgst gene according to the invention, or a genetic product, e.g. through expression of an RNAi sequence;
  (ii) an operator that controls the expression of the nucleotide sequence; and (iii) a promoter that is specific for cells that are critical for pollen formation or the function thereof, wherein the promoter is functionally linked to the nucleotide sequence that encodes a genetic product;

(b) optionally, breeding the plant obtained in step (a), under conditions that permit male sterility to be obtained as the result of the nucleotide sequence expression;

(c) crossbreeding the male sterile plants from (a) or (b) with pollen from a male fertile line in order to generate a hybrid plant that is male fertile, wherein the pollen from a second recombinant DNA molecule comprises: a nucleotide sequence that encodes a DNA binding protein and represses the transcription, and a promoter that controls the expression of the nucleotide sequence, wherein the DNA binding protein is able to bind the operator of the recombinant DNA of the male sterile plant, and repress the transcription.

Another system for producing pollen-sterile plants, in which foreign DNA is introduced into the nuclear genome, and can be used according to the invention, is described in the European patent application EP 0 344 029.

The present invention also relates to the use of the plants according to the invention for breeding or producing descendants, wherein the nucleus-encoded male sterile phenotype is used for recurrent selection. Furthermore, the present invention also relates to seeds or descendants, or organs, plant parts, tissues, or cells thereof, in addition to the plant according to the invention, used in the production of products normally made of renewable raw materials, such as food and feed, preferably sugar or syrup (molasses), wherein the molasses is also used for industrial applications, e.g. in fermenting alcohol, or as a nutrient for the production of biotechnology products, in the production of raw materials or substances for the chemical industry, e.g. fine chemicals, pharmaceuticals or the ingredients thereof, diagnostic products, cosmetics, bioethanol or biogas. One example of the use of sugar beets as a biogenetic raw material in biogas facilities is described in the patent application DE 10 2012 022 178 A1, see, e.g., paragraph 10.

Lastly, the present invention also relates to products obtained from the plants, organs, plant parts, issues, cells, seeds and descendants according to the invention, such as food, feed, and raw materials contained in a plant, seeds, descendants, organs, plant parts, tissues or cells, or components thereof.

The following examples explain the invention without limiting the subject matter of the invention thereto. If not otherwise indicated, microbiological standard methods are used, see, e.g., (Sambrook et al., Molecular Cloning; A Laboratory Manual, 3$^{rd}$ ed., Cold Spring Harbor Laboratory Press, Cold Spring Harbor, N.Y., 2001), Fritsch et al., Cold Spring Harbor Laboratory Press; 1989; Mayer et al., Immunochemical Methods In Cell And Molecular Biology, eds. Academic Press, London, 1987) and Weir et al., Handbook of Experimental Immunology, Volumes I-IV, Blackwell, eds., 1986).

EXAMPLES

1. Identification of a Locus that Causes Nucleus-Encoded Male Sterility

A donor with the internal label C311 [2043_K5] was used as the starting plant for identifying a locus that causes nucleus-encoded male sterility in sugar beets, which displays a recessive, nucleus-encoded, male sterile phenotype (working name gst). The presence and zygotic degree of the fundamental trait expression gst locus from this donor cannot, however, be checked in advance (i.e. before flowering) in the test material. Instead, a large number of putative sterile plants must be brought to the flowering stage in the field, or in a selfing block (S-block). Flowering plants are then manually examined for fertility or sterility, respectively (FIG. 1). Fertile individuals can subsequently be removed, and seed from sterile individuals can be harvested.

For a genetic and physical limitation of the gst locus that causes nucleus-encoded male sterility, a divided sugar beet mapping population for the trait is created. The target region on chromosome 1 was already known from initial pre-information of a genome-wide mapping. Male sterile individuals of the gst donor C311 [2043_K5] were crossbred with an annual line and the resulting F1 individuals are reproduced through self-fertilization. Descendants of the S1 generation were subsequently phenotyped for the mapping, and marked with KASP-DNA marker (KASP™ genotyping chemical from LGC Limited). 2 KASP-DNA markers, sxn2151s01 and sle3305s02, were developed, by means of which the genotype carrying the gst-locus could be distinguished from the reference genotype KWS2320 by identifying an SNP. The sxn2151s01 marker sequence in SEQ ID No. 24 and the sle3305s02 marker sequence in SEQ ID No. 26 indicate the presence of the gst locus; the sxn2151s01 marker sequence in SEQ ID No. 25 and the sle3305s02 marker sequence in SEQ ID No. 27 indicate the reference sequence, wherein the marker sequences each differ at nucleotide position 21 and there is a "G" at this location in the genotype carrying the gst-locus, and an "A" at this location in the reference group genotype KWS2320. As a result of this fine mapping, the region on chromosome 1 of the sugar beet genome that is flanked by the KASP-DNA markers sxn2151s01 at 33.42 cM and sle3305s02 a 35.15 cM (based on the genetic map ZR INT 1202) and carries the gst locus is clearly isolated. Based on the physical genome map (Physmapv2), this region has a physical size of 215.4 kbp and lies between positions 3185718 bp and 3401120 bp. Based on the identified position and the publically obtainable genome notation RefBeet 1.2 (http://bvseq.molgene.mpg.de/), 21 protein-encoding genes were identified that were located in this genome segment.

Homologous genes in model plants (e.g. *Arabidopsis thaliana* and *Oryza sativa*) were examined for all 21 gene models using bioinformatics approaches. A comprehensive analysis and assessment was carried out on the basis of the identified homologous genes in model plants. A gene encoded in the gst locus identified as a member of the family of cytochrome P450 monooxygenases (CYPs) on the basis of this comprehensive analysis of the sequences and the predicted structures. Despite considerable sequence diversity in the cytochrome P450 monooxygenases, all of the CYPs have common structural traits that are highly preserved in the region of the active center (see, e.g., Fischer et al., Bioinformatics 23 (2007), 2015-2017), and which were also found for the putative gst gene. The gene is called CYPgst for this reason.

With a more specific characterization of this gene, an *Arabidopsis thaliana* CYP gene was identified, i.e. CYP703A2, that exhibited a high sequence identity to this gene from the gst locus. An *Arabidopsis thaliana* mutant, in which this gene is deactivated through insertion of a T-DNA, displays a partial, or semi-male sterile phenotype (Morant et al., Plant Cell 19 (2007), 1473-1487). This can be explained on a mechanical basis through a function of the CYP703A2 in the synthesis of sporopollenin, the main component of the external layer of vital pollen. The absence of an external layer interrupts the maturation of the pollen, or leaves it vulnerable to environmental effects. There are, however, two substantial differences between the gst phenotype in the sugar beet phenotype and the phenotype of the described *Arabidopsis* mutant:

(i) in contrast to *Arabidopsis*, the knockout of the gene in sugar beets results in full male sterility, and (ii) while sterile pollen is fundamentally generated in *Arabidopsis* mutants, however, no pollen is formed in gst sugar beets according to the current state of analysis.

Therefore, the possibility should not be dismissed that these are different members of the CYP family and/or that the function of the two proteins is different in *Arabidopsis* and sugar beets. In addition, there is the fact that *Arabidopsis* is a wild herb from the family of cruciferous plants, with a compact, small genome, while the sugar beet is a cultivated plant, i.e. a plant that is grown, cultivated and bred by humans, used as a crop plant. As a result, experiments on *Arabidopsis*, and the results thereof, cannot be simply applied to cultivated plants. Furthermore, there are also important, agricultural processes with crop plants that never take place in *Arabidopsis*. These include, e.g., formation of beet roots, tubers and grain that function as storage organs and as vegetative reproductive organs, and interactions with symbiotic mycorrhizal fungi or pathogens that are not associated with *Arabidopsis*.

2. Characterization of the CYPgst Gene

After identifying the potential gene resulting in the gst phenotype, a comparative sequencing of a fragment of genomic DNA, comprising approx. 5 kbp, takes place. The fertile sugar beet reference genotype KWS2320, the sterile gst donor C311, and three individuals of the aforementioned fine mapped population that have been classified according to phenotypes and marker data as sterile, and three individuals thereof that have been classified according to phenotypes and marker data as homozygous fertile, were sequenced. The sequenced genome region comprises the gene model for BvCYPgst (GST, g6845.t1) shown in FIG. 2, and also approx. 1.5 kbp of the putative promoter region. The comparative sequencing discloses, aside from a series of Small Nucleotide Polymorphisms (SNPs) between sterile and fertile individuals, a 533 bp deletion in sterile genotypes that comprises the 5'UTR and the first exon of the gene model (FIG. 2 and FIG. 3).

The analysis of all of the identified polymorphisms showed that some of the deletions had an effect on the encoded protein, while all of the other mutations were either in untranslated regions, or generated synonymous codons. These deletions, in contrast, prevented a concrete transcription of the mRNA and the translation of functional protein is therefore impossible. Subsequent transcription analyses confirmed these findings (FIG. 5). BvCYP703A2 (GST, g6845.t1) is very specifically expressed in closed flowers and fruit in fertile genotypes. No expression thereof could be detected in roots and leaves. In contrast, expression of the GST gene cannot be detected in closed flowers in sterile genotypes, such that it can be concluded that the gene in sterile genotypes is fully deactivated.

Lastly, DNA markers were developed that can discriminate between sterile and fertile genotypes. KASP markers were developed for this that display the fertile allele (insertion) as a dominant trait (sle5983d14, sle5983d17).

| rnaName | Primer_forward | Primer_reverse |
|---|---|---|
| sle5983d14 | SEQ ID NO: 4:<br>ACCAAAATTTTATACCAATGGCTCAAG | SEQ ID NO: 5:<br>GGCCGGGAGGGAGTTTGTATGTT |
| sle5983d17 | SEQ ID NO: 6:<br>AGAAATCATACGTGAGATCTTAGTTCG | SEQ ID NO: 7:<br>GGTATGTGGACGAGACGCAAATACAT |

As a result, a conclusion can be drawn indirectly, regarding the present homozygous deletion, when both dominant markers (sle5983d14, sle4983d17) display a zero allele, and a third, ubiquitous marker confirming sufficient quality of the DNA extraction. Potential point mutations in the BvCYPgst gene resulting in a premature transcription interruption of the CYPgst gene, or can cause a disruption in the splicing, which can be tested using conventional methods for detecting DNA point mutations (SNP analysis), are compiled in the following Table 1.

TABLE 1

Potential point mutations in the CYPgst gene from *Beta vulgaris* subspecies *vulgaris*, that can lead to a premature transcription interruption in the CYPgst gene, or can cause a disruption in the splicing.

| Position gemäß SEQ ID Nr. 1 | Nukleotid | Mutation | Auswirkung der Mutation |
|---|---|---|---|
| 1771 | G | T | STOP Codon |
| 1778 | T | A or G | STOP Codon |
| 1788 | T | A or G | STOP Codon |
| 1790 | T | A or G | STOP Codon |
| 1797 | T | A | STOP Codon |
| 1813 | A | T | STOP Codon |
| 1820 | T | A or G | STOP Codon |
| 1824 | C | A or G | STOP Codon |
| 1825 | C | T | STOP Codon |
| 1829 | G | A | STOP Codon |
| 1830 | G | A | STOP Codon |
| 1834 | A | T | STOP Codon |
| 1842 | C | A or G | STOP Codon |
| 1844 | T | A or G | STOP Codon |
| 1848 | C | A or G | STOP Codon |
| 1857 | C | A or G | STOP Codon |
| 1858 | A | T | STOP Codon |
| 1883 | G | A | STOP Codon |
| 1884 | G | A | STOP Codon |
| 1889 | T | A or G | STOP Codon |
| 1894 | G | T | STOP Codon |
| 1906 | C | T | STOP Codon |
| 1940 | C | A or G | STOP Codon |
| 1947 | T | A | STOP Codon |
| 1948 | G | T | STOP Codon |
| 1951 | A | T | STOP Codon |
| 1956 | T | A or G | STOP Codon |
| 1964 | T | A or G | STOP Codon |
| 1971 | C | A or G | STOP Codon |

TABLE 1-continued

Potential point mutations in the CYPgst gene from Beta vulgaris subspecies vulgaris, that can lead to a premature transcription interruption in the CYPgst gene, or can cause a disruption in the splicing.

| Position gemäß SEQ ID Nr. 1 | Nukleotid | Mutation | Auswirkung der Mutation |
|---|---|---|---|
| 2014 | G | T | STOP Codon |
| 2026 | G | T | STOP Codon |
| 2033 | T | A or G | STOP Codon |
| 2038 | C | T | STOP Codon |
| 2041 | C | T | STOP Codon |
| 2075 | T | A or G | STOP Codon |
| 2090 | T | A | STOP Codon |
| 2097 | C | A or G | STOP Codon |
| 2117 | T | A | STOP Codon |
| 2128 | G | T | STOP Codon |
| 2138 | G | A | STOP Codon |
| 2139 | G | A | STOP Codon |
| 2140 | A | T | STOP Codon |
| 2143 | A | T | STOP Codon |
| 2149 | A | T | STOP Codon |
| 2160 | C | A | STOP Codon |
| 2164 | G | T | STOP Codon |
| 2171 | T | A | STOP Codon |
| 2182 | A | T | STOP Codon |
| 2185 | C | T | STOP Codon |
| 2191 | G | T | STOP Codon |
| 2218 | G | T | STOP Codon |
| 2224 | C | T | STOP Codon |
| 2231 | T | A | STOP Codon |
| 2236 | C | T | STOP Codon |
| 2246 | T | A or G | STOP Codon |
| 2260 | A | T | STOP Codon |
| 2266 | A | T | STOP Codon |
| 2279 | T | A | STOP Codon |
| 2284 | G | T | STOP Codon |
| 2291 | T | A or G | STOP Codon |
| 2320 | A | T | STOP Codon |
| 2327 | T | A | STOP Codon |
| 2335 | A | T | STOP Codon |
| 2338 | C | T | STOP Codon |
| 2343 | C | A or G | STOP Codon |
| 2368 | C | T | STOP Codon |
| 2380 | G | T | STOP Codon |
| 2401 | G | T | STOP Codon |
| 2405 | T | A | STOP Codon |
| 2411 | G | A | STOP Codon |
| 2412 | G | A | STOP Codon |
| 2414 | T | A or G | STOP Codon |
| 2423 | T | A | STOP Codon |
| 2430 | C | A or G | STOP Codon |
| 2432 | T | A | STOP Codon |
| 2442 | T | A or G | STOP Codon |
| 2444 | T | A | STOP Codon |
| 2453 | G | A | STOP Codon |
| 2454 | G | A | STOP Codon |
| 2459 | G | A | STOP Codon |
| 2460 | G | A | STOP Codon |
| 2472 | T | A or G | STOP Codon |
| 2473 | G | T | STOP Codon |
| 2478 | T | A | STOP Codon |
| 2479 | G | T | STOP Codon |
| 2482 | A | T | STOP Codon |
| 2485 | A | T | STOP Codon |
| 2494 | G | T | STOP Codon |
| 2500 | G | T | STOP Codon |
| 2503 | A | T | STOP Codon |
| 2527 | A | T | STOP Codon |
| 2536 | G | T | STOP Codon |
| 2539 | G | T | STOP Codon |
| 2548 | A | T | STOP Codon |
| 2551 | G | T | STOP Codon |
| 2554 | A | T | STOP Codon |
| 2557 | A | T | STOP Codon |
| 2563 | A | T | STOP Codon |
| 2566 | G | T | STOP Codon |
| 2569 | G | T | STOP Codon |
| 2575 | G | T | STOP Codon |
| 2584 | G | T | STOP Codon |
| 2590 | G | T | STOP Codon |
| 2612 | T | A | STOP Codon |
| 2615 | T | A | STOP Codon |
| 2621 | T | A | STOP Codon |
| 2629 | G | T | STOP Codon |
| 2635 | G | T | STOP Codon |
| 2641 | G | T | STOP Codon |
| 2665 | A | T | STOP Codon |
| 2677 | C | T | STOP Codon |
| 2679 | G | A | Spleiß-Mutation |
| 2680 | G | A | Spleiß-Mutation |
| 2681 | T | A | Spleiß-Mutation |
| 3505 | A | C or G or T | Spleiß-Mutation |
| 3506 | G | A or C ot T | Spleiß-Mutation |
| 3535 | C | A or G | STOP Codon |
| 3549 | G | T | STOP Codon |
| 3553 | G | A | STOP Codon |
| 3554 | G | A | STOP Codon |
| 3564 | G | T | STOP Codon |
| 3573 | A | T | STOP Codon |
| 3594 | A | T | STOP Codon |
| 3600 | C | T | STOP Codon |
| 3603 | C | T | STOP Codon |
| 3606 | G | T | STOP Codon |
| 3624 | G | T | STOP Codon |
| 3633 | C | T | STOP Codon |
| 3645 | G | T | STOP Codon |
| 3649 | C | A or G | STOP Codon |
| 3671 | C | A or G | STOP Codon |
| 3680 | T | A | STOP Codon |
| 3690 | G | T | STOP Codon |
| 3699 | C | T | STOP Codon |
| 3724 | T | A or G | STOP Codon |
| 3735 | G | T | STOP Codon |
| 3739 | C | A or G | STOP Codon |
| 3767 | T | A or G | STOP Codon |
| 3811 | T | A or G | STOP Codon |
| 3813 | G | T | STOP Codon |
| 3825 | A | T | STOP Codon |
| 3832 | G | A | STOP Codon |
| 3833 | G | A | STOP Codon |
| 3843 | G | T | STOP Codon |
| 3854 | C | A or G | STOP Codon |
| 3858 | G | T | STOP Codon |
| 3861 | A | T | STOP Codon |
| 3868 | G | A | STOP Codon |
| 3869 | G | A | STOP Codon |
| 3874 | T | A | STOP Codon |
| 3879 | G | T | STOP Codon |
| 3885 | A | T | STOP Codon |
| 3891 | G | T | STOP Codon |
| 3903 | G | T | STOP Codon |
| 3915 | A | T | STOP Codon |
| 3922 | T | A or G | STOP Codon |
| 3939 | A | T | STOP Codon |
| 3942 | A | T | STOP Codon |
| 3945 | A | T | STOP Codon |
| 3950 | T | A | STOP Codon |
| 3982 | T | A | STOP Codon |
| 3987 | G | T | STOP Codon |
| 3991 | T | A | STOP Codon |
| 4018 | G | A | STOP Codon |
| 4019 | G | A | STOP Codon |
| 4021 | T | A or G | STOP Codon |
| 4032 | G | T | STOP Codon |
| 4038 | A | T | STOP Codon |
| 4044 | G | T | STOP Codon |
| 4047 | G | T | STOP Codon |
| 4059 | A | T | STOP Codon |

TABLE 1-continued

Potential point mutations in the CYPgst gene from *Beta vulgaris* subspecies *vulgaris*, that can lead to a premature transcription interruption in the CYPgst gene, or can cause a disruption in the splicing.

| Position gemäß SEQ ID Nr. 1 | Nukleotid | Mutation | Auswirkung der Mutation |
|---|---|---|---|
| 4062 | G | T | STOP Codon |
| 4070 | T | A or G | STOP Codon |
| 4086 | A | T | STOP Codon |
| 4092 | C | T | STOP Codon |
| 4099 | T | A or G | STOP Codon |
| 4108 | T | A | STOP Codon |
| 4113 | A | T | STOP Codon |
| 4132 | T | A or G | STOP Codon |
| 4136 | T | A or G | STOP Codon |

3. Use of the CYPgst Gene or Locus in Hybrid Breeding

As explained above, the male sterile phenotype that gives rise to the gst locus is used in resistance breeding programs for simple crossbreeding in the framework of recurrent selection. Prior to the cloning of the gene in the framework of the present invention, and the associated development of genomic markers, four times as many plants must be grown and harvested than needed, due to the expected 3:1 phenotype division. These plants must be evaluated for sterility shortly after flowering, and fertile individuals must be removed, in order to prevent self-pollination. If numerous thousands of plants are grown per year, this manual selection is very labor intensive, and prone to error. Genomic markers according to the invention are now provided, see Example 2 and FIG. 2, with which it was possible, for example, to test 30,000 plants, and select 75,000 male sterile plants, that were subsequently planted.

There is a continuous effort to simplify breeding programs and seed production for sugar beets, and to reduce costs thereby. As such, commercial sugar beets are currently produced as triple-hybrids, in order to produce seeds of sufficient quality. The production of hybrids in the breeding program, thus in the non-commercial field, is likewise expensive and labor intensive, and is currently achieved by erecting dividing walls. It is now possible, using the gst phenotype according to the invention, and the associated DNA markers—after insertion of the gst locus, or after mutation/inhibition of the CYPgst gene in the breeding program—to select male sterile plants before the planting using DNA markers, and to thus simplify the production process. The parallel development of multi-germ tester genotypes (MUS testers), is likewise superfluous. In the long run, it is likewise conceivable to replace current CMS technologies with an alternative system with which the seed parent components can be made male sterile, e.g. by means of the SPT system specified above and shown in FIG. 5. Accordingly, it can also be reasonably assumed that CYPgst systems according to the invention can be used in other cultivated plants, in particular crop plants, as is the case in the commercial production of double-hybrids, such as corn. ms-genes play a major role in corn (*Zea mays*) in the development of alternative systems for producing hybrid seeds. Sequence analyses show that a putative corn homolog exists for BvCYPgst (GRMZM5g830329). There is a likewise large number of ms mutants in corn, of which only a portion have been cloned so far. The ms mutants can now be isolated by means of the present invention, the ms mutation of which can be attributed to a mutation, or inhibition of the corn homolog of BvCYPgst, and can be used in a targeted manner for seed production. The present invention can likewise be used in the development of a hybrid potato, e.g. in order to introduce targeted mutations in the potato homolog of the BvCYPgst gene, and to use the male sterility obtained in this manner in the potato to develop a diploid hybrid potato as set forth in the SPT system.

Lastly, the specific expression of the BvCYPgst gene in flowers and the tapetum enables a biotechnological use of the promoter, e.g. for expression of a positive sense/negative sense RNA or a ribozyme for inhibiting the BvCYPgst gene or for expression of a functional CYPgst protein, or a putative homolog, analog, or ortholog of the BvCYPgst gene to complement the mutation and restore the male fertile phenotype. It is assumed that the provision of the gene locus and the nucleic and amino acid sequences of the BvCYPgst gene, in addition to the genetic markers and the embodiments that are derived therefrom, is associated with a substantial simplification and savings in costs on the part of the breeding program, because, among other things, an early selection of sterile individuals is enabled. This likewise results in a logistical simplification and breeding expansion of the relevant programs.

The invention claimed is:

1. A *Beta vulgaris* plant that displays a recessive, nucleus-encoded male sterile phenotype, wherein the phenotype correlates to a mutation comprising the endogenic cytochrome P450 oxidase gene, or to the absence, or low content or activity, of a functional cytochrome P450 oxidase protein encoded by the cytochrome P450 oxidase wild type gene in comparison with a corresponding male fertile wild type *Beta vulgaris* plant, wherein the cytochrome P450 oxidase gene is a gene selected from the group consisting of:
   (a) a nucleotide sequence comprising SEQ ID No. 1 or 2;
   (b) a nucleotide sequence encoding the amino acid sequence of SEQ ID No. 3; and
   (c) a nucleotide sequence which codes for an amino acid sequence which has an identity of at least 95% with SEQ ID No. 3,
   wherein the mutation is selected from the group consisting of:
      a deletion of one or more nucleotides between nucleotide positions 1560 and 2095 of SEQ ID No. 1; and
      a point mutation of one or more nucleotides between nucleotide positions 1560 and 2095 of SEQ ID No. 1,
      wherein the cytochrome P450 oxidase gene is located in a segment on chromosome 1 between marker loci sxn2151s01 and sle3305s02, and
      wherein the sxn2151s01 marker sequence of SEQ ID No. 24 and the sle3305s02 marker sequence of SEQ ID No. 26 indicate the presence of a gst locus resulting in male sterility.

2. The plant according to claim 1, which is heterozygous for the mutation and male fertile, or is homozygous for the mutation and is male sterile, wherein the formation of functional pollen is suppressed in the sterile plant.

3. The plant according to claim 1, wherein the mutation prevents transcription and/or translation of a functional protein, and wherein the deletion in *Beta vulgaris* can be detected by the absence of one or both marker loci sle5983d14 and sle5983d17, wherein the marker locus sle5983d14 is the amplification product of the primer pair set forth in SEQ NOs: 4 and 5 and sle5983d17 is the amplification product of the primer pair set forth in SEQ ID NOs: 6 and 7.

4. A nucleic acid molecule or recombinant DNA molecule comprising, a nucleotide sequence selected from the group consisting of:
   (a) a nucleotide sequence containing the nucleotide sequence of SEQ ID No. 2;
   (b) a nucleotide sequence that encodes the amino acid sequence of SEQ ID No. 3; and
   (c) a nucleotide sequence that encodes an amino acid sequence that comprises at least one amino acid deletion, substitution, addition and/or insertion in the amino acid sequence of SEQ ID NO. 3, and is identical to at least 90% of the entire amino acid sequence,
   wherein the nucleic acid filthier comprises a deletion, wherein the deletion results in no synthesis of functional *Beta vulgaris* cytochrome P450 oxidase protein in the *Beta vulgaris* flowers and/or fruit, and wherein the deletion comprises a deletion of one or more nucleotides between nucleotide positions 1560 and 2095 of SEQ ID No. 1; and wherein the deletion in *Beta vulgaris* can be detected by the absence of one or both marker loci sle5983d14 and sle5983d17, wherein the marker locus sle5983d14 is the amplification product of the primer pair set forth in SEQ NOs: 4 and 5 and sle5983d17 is the amplification product of the primer pair set forth in SEQ ID NOs: 6 and 7.

5. A vector comprising a nucleic acid molecule or recombinant DNA molecule according to claim 4.

6. A host cell containing a recombinant DNA molecule or nucleic acid molecule according to claim 4.

7. A kit comprising a DNA molecule or nucleic acid molecule, according to claim 4.

8. A method for restoring the fertility of a plant according to claim 1, comprising the insertion of a functional cytochrome P450 oxidase gene in the *Beta vulgaris* plant.

9. An organ, plant part, tissue or cell of the plant according to claim 1.

10. A method comprising utilizing the nucleic acid molecule according to claim 1 in the production of a recessive, nucleus-encoded, male sterile plant, in the production of a plant with restored fertility, in the production of a hybrid plant, in resistance programs, or for seed production.

11. The vector according to claim 5, wherein the vector is a plant vector.

12. The plant according to claim 1, comprising a nucleotide sequence according to SEQ ID No. 8.

13. The nucleic acid molecule or recombinant DNA molecule according to claim 4, comprising a nucleotide sequence according to SEQ ID No. 8.

* * * * *